United States Patent [19]

Baker et al.

[11] Patent Number: 5,612,337

[45] Date of Patent: Mar. 18, 1997

[54] SUBSTITUTED MORPHOLINE DERIVATIVES AND THEIR USE AS THERAPEUTIC AGENTS

[75] Inventors: Raymond Baker, Green Tye; Timothy Harrison, Great Dunmow; Angus M. MacLeod, Bishops Stortford; Andrew P. Owens, Rushden; Eileen M. Seward, Bishops Stortford; Christopher J. Swain, Duxford; Martin R. Teall, Bishops Stortford, all of United Kingdom

[73] Assignee: Merck Sharp & Dohme Limited, Hoddesdon, England

[21] Appl. No.: 663,201

[22] PCT Filed: Dec. 23, 1994

[86] PCT No.: PCT/GB94/02819

§ 371 Date: Jun. 13, 1996

§ 102(e) Date: Jun. 13, 1996

[87] PCT Pub. No.: WO95/18124

PCT Pub. Date: Jul. 6, 1995

[30] Foreign Application Priority Data

| Dec. 29, 1993 | [GB] | United Kingdom | 9326480 |
| Apr. 12, 1994 | [GB] | United Kingdom | 9407189 |
| Apr. 22, 1994 | [GB] | United Kingdom | 9408065 |
| Aug. 15, 1994 | [GB] | United Kingdom | 9416428 |

[51] Int. Cl.[6] ............ A61K 31/535; C07D 413/06; C07D 413/14

[52] U.S. Cl. ............ 514/236.2; 514/232.2; 544/58.5; 544/82; 544/121; 544/130; 544/132; 544/139

[58] Field of Search ............ 544/132, 139; 514/236.2

[56] References Cited

U.S. PATENT DOCUMENTS 5,512,570 4/1996 Dorn et al. .

FOREIGN PATENT DOCUMENTS

| 0528495 | 2/1993 | European Pat. Off. . |
| 0577394 | 1/1994 | European Pat. Off. . |
| WO95/16679 | 6/1995 | WIPO . |

*Primary Examiner*—Robert W. Ramsuer
*Attorney, Agent, or Firm*—J. Eric Thies; David L. Rose

[57] ABSTRACT

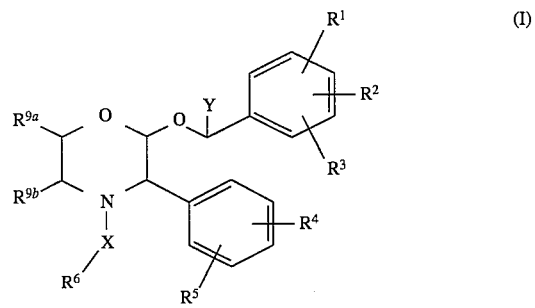

The present invention relates to compounds of formula (I), wherein $R^1$ is hydrogen, halogen, $C_{1-6}$ alkyl, $C_{1-6}$ alkoxy, $CF_3$, $NO_2$, $CN$, $SR^a$, $SOR^a$, $SO_2R^a$, $CO_2R^a$, $CONR^aR^b$, $C_{2-6}$ alkenyl, $C_{2-6}$ alkynyl or $C_{1-4}$ alkyl substituted by $C_{1-4}$ alkoxy, where $R^a$ and $R^b$ are hydrogen or $C_{1-4}$ alkyl; $R^2$ is hydrogen, halogen, $C_{1-6}$ alkyl, $C_{1-6}$ alkoxy substituted by $C_{1-4}$ alkoxy or $CF_3$; $R^3$ is hydrogen, halogen or $CF_3$; $R^4$ is selected from the definitions of $R^1$; $R^5$ is selected from the definitions of $R^2$; $R^6$ is a 5-membered or 6-membered heterocyclic ring containing 2 or 3 nitrogen atoms optionally substituted by $=O$, $=S$ or a $C_{1-4}$ alkyl group, and optionally substituted by an aminoalkyl group; $R^{9a}$ and $R^{9b}$ are hydrogen or $C_{1-4}$ alkyl, or $R^{9a}$ and $R^{9b}$ are joined to form a $C_{5-7}$ ring; X is $C_{1-4}$ alkylene optionally substituted by oxo; and Y is a $C_{1-4}$ alkyl group optionally substituted by hydroxyl; with the proviso that if Y is $C_{1-4}$ alkyl, $R^6$ is substituted at least by an aminoalkyl group; and pharmaceutically acceptable salts and prodrugs thereof. The compounds are of particular use in the treatment of pain, inflammation, migraine and emesis.

24 Claims, No Drawings

SUBSTITUTED MORPHOLINE DERIVATIVES AND THEIR USE AS THERAPEUTIC AGENTS

This application is a 371 of PCT/G894/02819 filed Dec. 23, 1994.

This invention relates to a class of aromatic compounds which are useful as tachykinin antagonists. More particularly, the compounds of the invention contain an amine-substituted azo-heterocyclic moiety.

The tachykinins are a group of naturally occurring peptides found widely distributed throughout mammalian tissues, both within the central nervous system and in peripheral nervous and circulatory systems.

At present, there are three known mammalian tachykinins referred to as substance P, neurokinin A (NKA, substance K, neuromedin L) and neurokinin B (NKB, neuromedin K) (for review see J. E. Maggio, Peptides (1985) 6(suppl. 3), 237–242). The current nomenclature designates the three tachykinin receptors mediating the biological actions of substance P, NKA and NKB as the $NK_1$, $NK_2$ and $NK_3$ receptors, respectively.

Evidence for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases, proliferative vitreoretinopathy, irritable bowel syndrome and disorders of bladder function including cystitis and bladder detruser hyper-reflexia is reviewed in "Tachykinin Receptors and Tachykinin Receptor Antagonists", C. A. Maggi, R. Patacchini, P. Rovero and A. Giachetti, *J. Auton. Pharmacol.* (1993) 13, 23–93.

For instance, substance P is believed inter alia to be involved in the neurotransmission of pain sensations [Otsuka et al, "Role of Substance P as a Sensory Transmitter in Spinal Cord and Sympathetic Ganglia" in 1982 *Substance P in the Nervous System*, Ciba Foundation Symposium 91, 13–34 (published by Pitman) and Otsuka and Yanagisawa, "Does Substance P Act as a Pain Transmitter?" *TIPS* (1987) 8, 506–510], specifically in the transmission of pain in migraine (B. E. B. Sandberg et al, *J. Med Chem,* (1982) 25, 1009) and in arthritis [Levine et al *Science* (1984) 226, 547–549]. Tachykinins have also been implicated in gastrointestinal (GI) disorders and diseases of the GI tract such as inflammatory bowel disease [Mantyh et al *Neuroscience* (1988) 25(3), 817–37 and D. Regoli in *"Trends in Cluster Headache"* Ed. Sicuteri et al Elsevier Scientific Publishers, Amsterdam (1987) page 85] and emesis [F. D. Tattersall et al, *Eur. J. Pharmacol.,* (1993) 250, R5–R6]. It is also hypothesised that there is a neurogenic mechanism for arthritis in which substance P may play a role [Kidd et al "A Neurogenic Mechanism for Symmetrical Arthritis" in *The Lancet,* 11 Nov. 1989 and Grönblad et al, "Neuropeptides in Synovium of Patients with Rheumatoid Arthritis and Osteoarthritis" in *J. Rheumatol.* (1988) 15(12), 1807–10]. Therefore, substance P is believed to be involved in the inflammatory response in diseases such as rheumatoid arthritis and osteoarthritis, and fibrositis [O'Byrne et al, *Arthritis and Rheumatism* (1990) 33, 1023–8]. Other disease areas where tachykinin antagonists are believed to be useful are allergic conditions [Hamelet et al, *Can. J. Pharmacol.*

*Physiol.* (1988) 66, 1361–7], immunoregulation [Lotz et al, *Science* (1988) 241, 1218–21 and Kimball et al, *J. Immunol.* (1988) 141(10), 3564–9] vasodilation, bronchospasm, reflex or neuronal control of the viscera [Mantyh et al, *PNAS* (1988) 85, 3235–9] and, possibly by arresting or slowing β-amyloid-mediated neurodegenerative changes [Yankner et al, *Science* (1990) 250, 279–82] in senile dementia of the Alzheimer type, Alzheimer's disease and Down's Syndrome.

Tachykinin antagonists may also be useful in the treatment of small cell carcinomas, in particular small cell lung cancer (SCLC) [Langdon et al, *Cancer Research* (1992) 52, 4554–7].

Substance P may also play a role in demyelinating diseases such as multiple sclerosis and amyotrophic lateral sclerosis [J. Luber-Narod et al, poster *C.I.N.P. XVIIIth Congress,* 28th Jun.–2nd Jul. 1992], and in disorders of bladder function such as bladder detrusor hyper-reflexia (*Lancet,* 16th May 1992, 1239).

It has furthermore been suggested that tachykinins have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophilic fascioliasis, reflex sympathetic dystrophy such as shoulder/hand syndrome, addiction disorders such as alcoholism, stress related somatic disorders, neuropathy, neuralgia, disorders related to immune enhancement or suppression such as systemic lupus erythmatosus (European patent specification no. 0 436 334), ophthalmic disease such as conjuctivitis, vernal conjunctivitis, and the like, and cutaneous diseases such as contact dermatitis, atopic dermatitis, urticaria, and other eczematoid dermatitis (European patent specification no. 0 394 989).

European patent specification no. 0 577 394 (published 5th Jan. 1994) discloses morpholine and thiomorpholine tachykinin receptor antagonists of the general formula

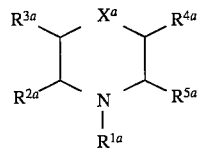

wherein $R^{1a}$ is a large variety of substituents;

$R^{2a}$ and $R^{3a}$ are inter aria hydrogen;

$R^{4a}$ is inter alia

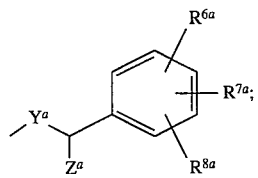

$R^{5a}$ is inter alia optionally substituted phenyl;

$R^{6a}$, $R^{7a}$ and $R^{8a}$ are a variety of substituents;

$X^a$ is O, S, SO or $SO_2$;

$Y^a$ is inter alia O; and $Z^a$ is hydrogen or $C_{1-4}$ alkyl.

European patent specification no. 0 528 495 (published 24th Feb. 1993) discloses azacyclic derivatives useful as tachykinin antagonists, which compounds have the general formula:

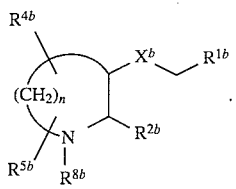

wherein n is 1, 2 or 3;

$X^b$ is O or S;

$R^{1b}$ is optionally substituted phenyl;

$R^{2b}$ is aryl, heteroaryl, benzhydryl or benzyl;

$R^{4b}$ and $R^{5b}$ are independently H, halo, $CH_2OR^{9b}$, $C_{1-6}$alkyl, oxo, $CO_2R^{10b}$ or $CONR^{10b}R^{11b}$.

$R^{8b}$ is H, $COR^{9b}$, $CO_2R^{10b}$ or optionally substituted $C_{1-6}$alkyl;

$R^{9b}$ is H, $C_{1-6}$alkyl or phenyl; and $R^{10b}$ and $R^{11b}$ are independently H or $C_{1-6}$alkyl.

We have now found a further class of non-peptides which are potent antagonists of tachykinins, especially of substance P.

It is desirable that compounds may be administered orally and by injection. Compounds have now been discovered which act as potent non-peptide tachykinin antagonists and which, by virtue of their advantageous aqueous solubility, are particularly easily formulated for administration by both the oral and injection routes, for example in aqueous media.

Furthermore, the compounds of the present invention possess a particularly advantageous profile of activity having potent antagonist activity at the $NK_1$ receptor and a long duration of action. The compounds of the present invention, and in particular their pharmaceutically acceptable acid addition salts, are also particularly suited to a wide variety of pharmaceutical formulations by virtue of their stability.

The present invention provides compounds of the formula (I):

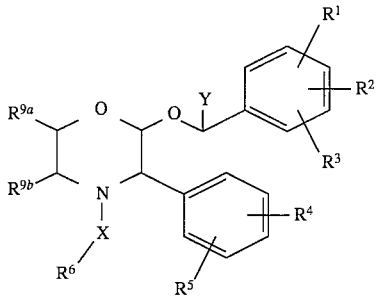

wherein $R^1$ is hydrogen, halogen, $C_{1-6}$alkyl, $C_{1-6}$alkoxy, $CF_3$, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, where $R^a$ and $R^b$ each independently represent hydrogen or $C_{1-4}$alkyl;

$R^2$ is hydrogen, halogen, $C_{1-6}$alkyl, $C_{1-6}$alkoxy substituted by $C_{1-4}$alkoxy or $CF_3$;

$R^3$ is hydrogen, halogen or $CF_3$;

$R^4$ is hydrogen, halogen, $C_{1-6}$alkyl, $C_{1-6}$alkoxy, $CF_3$, $NO_2$, CN, $SR^a$, $SOR^a$, $SO_2R^a$, $CO_2R^a$, $CONR^aR^b$, $C_{2-6}$alkenyl $C_{2-6}$alkynyl or $C_{1-4}$alkyl substituted by $C_{1-4}$alkoxy, where $R^a$ and $R^b$ each independently represent hydrogen or $C_{1-4}$alkyl;

$R^5$ is hydrogen, halogen, $C_{1-6}$alkyl, $C_{1-6}$alkoxy substituted by $C_{1-4}$alkoxy or $CF_3$;

$R^6$ is a 5-membered or 6-membered heterocyclic ring containing 2 or 3 nitrogen atoms optionally substituted by =O, =S or a $C_{1-4}$alkyl group, and optionally substituted by a group of the formula $ZNR^7R^8$ where Z is $C_{1-6}$alkylene or $C_{3-6}$cycloalkylene;

$R^7$ is hydrogen, $C_{1-4}$alkyl, $C_{3-7}$cycloalkyl or $C_{3-7}$cycloalkylC_{1-4}$alkyl, or $C_{2-4}$alkyl substituted by $C_{1-4}$alkoxy or hydroxyl;

$R^8$ is hydrogen, $C_{1-4}$alkyl, $C_{3-7}$cycloalkyl or $C_{3-7}$cycloalkylC_{1-4}$alkyl, or $C_{2-4}$alkyl substituted by one or two substituents selected from $C_{1-4}$alkoxy, hydroxyl or a 4, 5 or 6 membered heteroaliphatic ring containing one or two heteroatoms selected from N, O and S;

or $R^7$, $R^8$ and the nitrogen atom to which they are attached form a heteroaliphatic ring of 4 to 7 ring atoms, optionally substituted by one or two groups selected from hydroxy or $C_{1-4}$alkyl optionally substituted by a $C_{1-4}$alkoxy or hydroxyl group, and optionally containing a double bond, which ring may optionally contain an oxygen or sulphur ring atom, a group S(O) or $S(O)_2$ or a second nitrogen atom which will be part of a NH or $NR^c$ moiety where $R^c$ is $C_{1-4}$alkyl optionally substituted by hydroxy or $C_{1-4}$alkoxy;

or $R^7$, $R^8$ and the nitrogen atom to which they are attached form a non-aromatic azabicyclic ring system of 6 to 12 ring atoms;

or Z, $R^7$ and the nitrogen atom to which they are attached form a heteroaliphatic ring of 4 to 7 ring atoms which may optionally contain an oxygen ring atom;

$R^{9a}$ and $R^{9b}$ are each independently hydrogen or $C_{1-4}$alkyl, or $R^{9a}$ and $R^{9b}$ are joined so, together with the carbon atoms to which they are attached, there is formed a $C_{5-7}$ ring;

X is an alkylene chain of 1 to 4 carbon atoms optionally substituted by oxo; and Y is a $C_{1-4}$alkyl group optionally substituted by a hydroxyl group;

with the proviso that if Y is $C_{1-4}$alkyl, $R^6$ is substituted at least by a group of formula $ZNR^7R^8$ as defined above;

and pharmaceutically acceptable salts and prodrugs thereof.

Certain particularly apt compounds of the present invention include those wherein $R^1$ is hydrogen, $C_{1-4}$alkyl, $C_{1-4}$alkoxy, halo or $CF_3$.

Most aptly $R^2$ is hydrogen, $C_{1-4}$alkyl, $C_{1-4}$alkoxy, halogen or $CF_3$.

Most aptly $R^3$ is hydrogen, fluorine, chlorine or $CF_3$.

Favourably $R^1$ is fluorine, chlorine or $CF_3$.

Favourably $R^2$ is hydrogen, fluorine, chlorine or $CF_3$.

Favourably $R^3$ is hydrogen, fluorine, chlorine or $CF_3$.

Preferably $R^1$ and $R^2$ are in the 3 and 5 positions of the phenyl ring.

More preferably $R^1$ is 3-fluoro or 3-$CF_3$.

More preferably $R^2$ is 5-fluoro or 5-$CF_3$.

More preferably $R^3$ is hydrogen.

Most preferably $R^1$ is 3-F or 3-$CF_3$, $R^2$ is 5-$CF_3$ and $R^3$ is hydrogen.

Most aptly $R^4$ is hydrogen.

Most aptly $R^5$ is hydrogen, fluorine, chlorine or $CF_3$.

Preferably $R^4$ is hydrogen and $R^5$ is hydrogen or 4-fluoro.

Most aptly $R^{9a}$ and $R^{9b}$ are each independently hydrogen or methyl.

Preferably $R^{9a}$ is hydrogen. Preferably $R^{9b}$ is hydrogen. Most preferably $R^{9a}$ and $R^{9b}$ are both hydrogen.

From the foregoing it will be appreciated that a particularly apt sub-group of compounds of this invention are those of the formula (Ia) and pharmaceutically acceptable salts and prodrugs thereof:

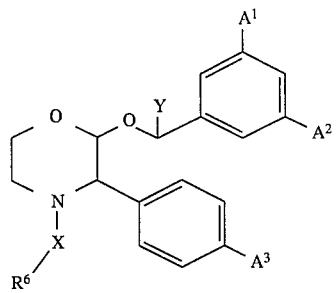

(Ia)

wherein
$A^1$ is fluorine or $CF_3$;
$A^2$ is fluorine or $CF_3$;
$A^3$ is fluorine or hydrogen;
and X, Y and $R^6$ are as defined in relation to formula (I).

According to a second or further aspect of the present invention, a preferred class of compound of formula (I) or (Ia) is that wherein Y represents a $C_{1-4}$alkyl group substituted by a hydroxy group; or a pharmaceutically acceptable salt or prodrug thereof.

According to a further or alternative aspect of the present invention, another preferred class of compound of formula (I) or (Ia) is that wherein Y represents a $C_{1-4}$alkyl group, with the proviso that $R^6$ is substituted at least by a group of the formula $ZNR^7R^8$ as defined above; or a pharmaceutically acceptable salt or prodrug thereof.

According to another aspect of the present invention, a further preferred class of compound of formula (I) or (Ia) is that wherein Y represents a $C_{1-4}$alkyl group; and $R^6$ represesents a 5-membered or 6-membered heterocyclic ring containing 2 or 3 nitrogen atoms optionally substituted by =O or =S and substituted by a group of the formula $ZNR^7R^8$ where Z is $C_{1-6}$alkylene or $C_{3-6}$cycloalkylene;

$R^7$ is hydrogen, $C_{1-4}$alkyl, $C_{3-7}$cycloalkyl or $C_{3-7}$cycloalkyl$C_{1-4}$alkyl, or $C_{2-4}$alkyl substituted by $C_{1-4}$alkoxy or hydroxyl;

$R^8$ is hydrogen, $C_{1-4}$alkyl, $C_{3-7}$cycloalkyl or $C_{3-7}$cycloalkyl$C_{1-4}$alkyl, or $C_{2-4}$alkyl substituted by one or two substituents selected from $C_{1-4}$alkoxy, hydroxyl or a 4, 5 or 6 membered heteroaliphatic ring containing one or two heteroatoms selected from N, O and S;

or $R^7$, $R^8$ and the nitrogen atom to which they are attached form a heteroaliphatic ring of 4 to 7 ring atoms, optionally substituted by a hydroxy group, and optionally containing a double bond, which ring may optionally contain an oxygen or sulphur ring atom, a group S(O) or S(O)$_2$ or a second nitrogen atom which will be part of a NH or $NR^c$ moiety where $R^c$ is $C_{1-4}$alkyl optionally substituted by hydroxy or $C_{1-4}$alkoxy;

or Z, $R^7$ and the nitrogen atom to which they are attached form a heteroaliphatic ring of 4 to 7 ring atoms which may optionally contain an oxygen ring atom;

or a pharmaceutically acceptable salt or prodrug thereof.

According to yet another aspect of the present invention, a preferred class of compounds of formula (I) or (Ia) is that wherein Y represents a $C_{1-4}$alkyl group; and $R^6$ is a 5-membered or 6-membered heterocyclic ring containing 2 or 3 nitrogen atoms optionally substituted by =O or =S and substituted by a group of the formula $ZNR^7R^8$ where Z is $C_{1-6}$alkylene or $C_{3-6}$cycloalkylene;

$R^7$ is hydrogen or $C_{1-4}$alkyl, or $C_{2-4}$alkyl substituted by $C_{1-4}$alkoxy or hydroxyl, $R^8$ is hydrogen or $C_{1-4}$alkyl or $C_{2-4}$alkyl substituted by $C_{1-4}$alkoxy, hydroxyl or a 5 or 6 membered heteroaliphatic ring containing one or two heteroatoms selected from N, O and S;

or $R^7$, $R^8$ and the nitrogen atom to which they are attached form a heteroaliphatic ring of 4 to 7 ring atoms, optionally substituted by a hydroxy group, which ring may optionally contain an oxygen or sulphur ring atom, a group S(O) or S(O)$_2$ or a second nitrogen atom which will be part of a NH or $NR^c$ moiety where $R^c$ is $C_{1-4}$alkyl optionally substituted by hydroxy or $C_{1-4}$alkoxy;

or Z, $R^7$ and the nitrogen atom to which they are attached form a heteroaliphatic ring of 4 to 7 ring atoms which may optionally contain an oxygen ring atom;

or a pharmaceutically acceptable salt or prodrug thereof.

According to a further aspect of the present invention, another preferred class of compound of formula (I) or (Ia) is that wherein Y represents a $C_{1-4}$alkyl group substituted by a hydroxyl group; and $R^6$ is a 5-membered or 6-membered heterocyclic ring containing 2 or 3 nitrogen atoms optionally substituted by =O or =S and optionally substituted by a group of the formula $ZNR^7R^8$ where Z is $C_{1-6}$alkylene or $C_{3-6}$cycloalkylene;

$R^7$ is hydrogen or $C_{1-4}$alkyl, or $C_{2-4}$alkyl substituted by $C_{1-4}$alkoxy or hydroxyl, $R^8$ is hydrogen or $C_{1-4}$alkyl or $C_{2-4}$alkyl substituted by $C_{1-4}$alkoxy or hydroxyl;

or $R^7$, $R^8$ and the nitrogen atom to which they are attached form a heteroaliphatic ring of 4 to 7 ring atoms which may optionally contain an oxygen ring atom or a second nitrogen atom which will be part of a NH or $NR^c$ moiety where $R^c$ is $C_{1-4}$alkyl optionally substituted by hydroxy or $C_{1-4}$alkoxy;

or Z, $R^7$ and the nitrogen atom to which they are attached form a heteroaliphatic ring of 4 to 7 ring atoms which may optionally contain an oxygen ring atom;

or a pharmaceutically acceptable salt or prodrug thereof.

According to another aspect of the present invention, a further preferred class of compound of formula (I) or (Ia) is that wherein $R^6$ is a 5-membered or 6-membered heterocyclic ring containing 2 or 3 nitrogen atoms optionally substituted by =O or =S and optionally substituted by a group of the formula $ZNR^7R^8$ where Z is $C_{1-6}$alkylene or $C_{3-6}$cycloalkyl;

$R^7$ is hydrogen or $C_{1-4}$alkyl, or $C_{2-4}$alkyl substituted by $C_{1-4}$alkoxy or hydroxyl, $R^8$ is hydrogen or $C_{1-4}$alkyl or $C_{2-4}$alkyl substituted by $C_{1-4}$alkoxy or hydroxyl;

or $R^7$, $R^8$ and the nitrogen atom to which they are attached form a heteroaliphatic ring of 4 to 7 ring atoms which may optionally contain an oxygen ring atom or a second nitrogen atom which will be part of a NH or $NR^c$ moiety where $R^c$ is $C_{1-4}$alkyl optionally substituted by hydroxy or $C_{1-4}$alkoxy;

or Z, $R^7$ and the nitrogen atom to which that are attached form a heteroaliphatic ring to 4 to 7 ring atoms which may optionally contain an oxygen ring atom;

or a pharmaceutically acceptable salt or prodrug thereof.

A preferred group Y for compounds of the formulae (I) or (Ia) is the CH$_2$OH group.

Another preferred group Y for compounds of the formulae (I) or (Ia) is the CH$_3$ group.

Particularly apt values for X for compounds of the formulae (I) or (Ia) include CH$_2$, CH(CH$_3$) and CH$_2$CH$_2$ of which the CH$_2$ group is preferred.

Favourably R$^6$ is a 5-membered ring.

In particular, R$^6$ may, bearing in mind the proviso in the definition of formula (I), represent a heterocyclic ring selected from:

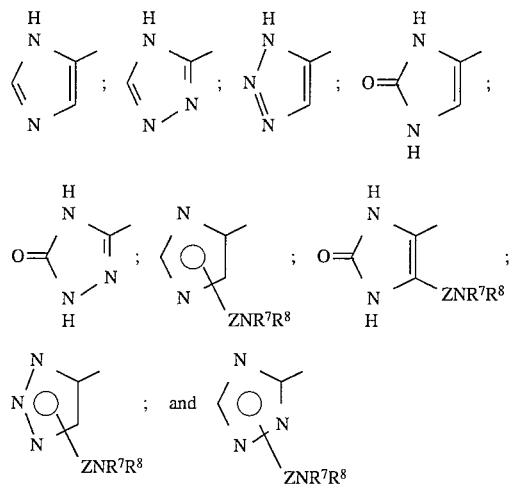

Particularly preferred heterocyclic rings represented by R$^6$ are selected from:

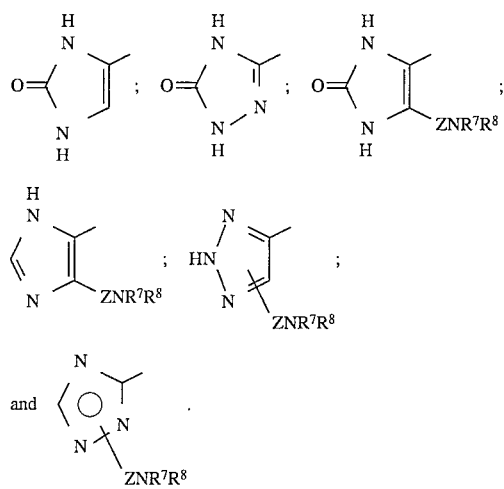

Most especially, R$^6$ may represent a heterocyclic ring selected from:

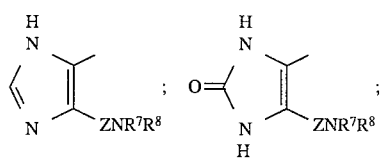

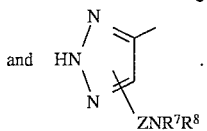

A particularly preferred heterocyclic ring represented by R$^6$ is:

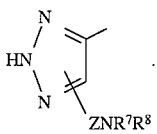

One favoured group of compounds of this invention are of the formula (Ib) and pharmaceutically acceptable salts and prodrugs thereof:

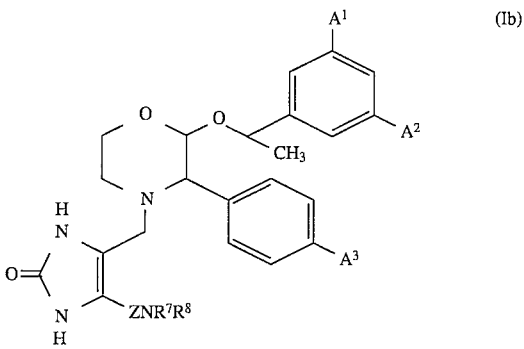

(Ib)

wherein A$^1$, A$^2$ and A$^3$ are defined in relation to formula (Ia) and wherein Z, R$^7$ and R$^8$ are as defined in relation to formula (I).

A further favoured group of compounds of the present invention are of the formula (Ic) and pharmaceutically acceptable salts and prodrugs thereof:

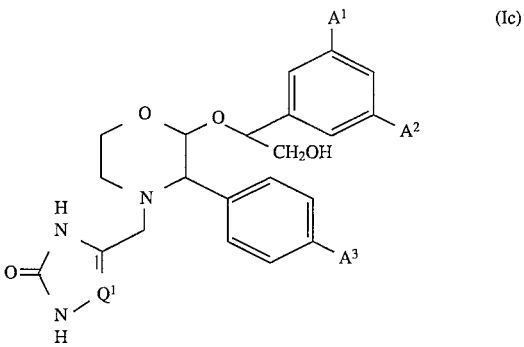

(Ic)

wherein A$^1$, A$^2$ and A$^3$ are as defined in relation to formula (Ia) and Q$^1$ is CH or N or C-ZNR$^7$R$^8$ wherein Z, R$^7$ and R$^8$ are as defined in relation to formula (I).

Another favoured group of compounds of the present invention are of the formula (Id) and pharmaceutically acceptable salts and prodrugs thereof:

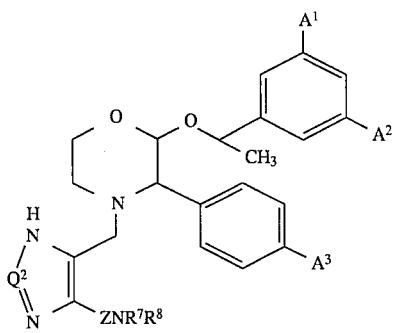

wherein $A^1$, $A^2$ and $A^3$ are defined in relation to formula (Ia), $Q^2$ is CH or N and Z, $R^7$ and $R^8$ are as defined in relation to formula (I).

With respect to compounds of the formulae (I), (Ia), (Ib), (Ic) and (Id), Z may be a linear, branched or cyclic group. Favourably Z contains 1 to 4 carbon atoms and most favourably 1 or 2 carbon atoms. A particularly favourable group Z is $CH_2$.

With respect to compounds of the formulae (I), (Ia), (Ib), (Ic) and (Id), $R^7$ may aptly be a $C_{1-4}$alkyl group or a $C_{2-4}$aikyl group substituted by a hydroxyl or $C_{1-2}$alkoxy group, $R^8$ may aptly be a $C_{1-4}$alkyl group or a $C_{1-4}$alkyl group substituted by a hydroxyl or $C_{1-2}$alkoxy group, or $R^7$ and $R^8$ may be linked so that, together with the nitrogen atom to which they are attached, they form an azetidinyl, pyrrolidinyl, piperidyl, morpholino, thiomorpholino, piperazino or piperazino group substituted on the nitrogen atom by a $C_{1-4}$alkyl group or a $C_{2-4}$alkyl group substituted by a hydroxy or $C_{1-2}$alkoxy group.

Where the group $NR^7R^8$ represents a heteroaliphatic ring of 4 to 7 ring atoms and said ring contains a double bond, a particularly preferred group is 3-pyrroline.

Where the group $NR^7R^8$ represents a non-aromatic azabicyclic ring system, such a system may contain between 6 and 12, and preferably between 7 and 10, ring atoms. Suitable rings include 5-azabicyclo[2.1.1]hexyl, 5-azabicyclo[2.2.1]heptyl, 6-azabicyclo[3.2.1]octyl, 2l-azabicyclo[2.2.2]octyl, 6-azabicyclo[3.2.2]nonyl, 6-azabicio[3.3.1]nonyl, 6-azabicyclo[3.2.2]decyl, 7-azabicyclo[4.3.1]decyl, 7-azabicyclo[4.4.1]undecyl and 8-azabicyclo[5.4.1]dodecyl, especially 5-azabicyclo[2.2.1]heptyl and 6-azabicio[3.2.1]octyl.

Where $R^8$ represents a $C_{2-4}$alkyl group substituted by a 5 or 6 membered heteroaliphatic ring containing one or two heteroatoms selected from N, O and S, suitable rings include pyrrolidino, piperidino, piperazino, morpholino, or thiomorpholino. Particularly preferred are nitrogen containing heteroaliphatic rings, especially pyrrolidino and morpholino rings.

Particularly suitable moieties $ZNR^7R^8$ include those wherein Z is $CH_2$ or $CH_2CH_2$ and $NR^7R^8$ is amino, methylamino, dimethylamino, diethylamino, azetidinyl, pyrrolidino and morpholino.

Further preferred moleties represented by $ZNR^7R^8$ are those wherein Z is $CH_2$ or $CH_2CH_2$, $R^7$ represents hydrogen, $C_{1-4}$alkyl or $C_{3-6}$cycloalkyl and $R^8$ is $C_{2-4}$alkyl substituted by one or two substituents selected from hydroxy, $C_{1-2}$alkoxy, azetidinyl, pyrrolidino, piperidino, morpholino or thiomorpholino.

In particular, Z is preferably $CH_2$ and $NR^7R^8$ is preferably dimethylamino, azetidinyl or pyrrolidino, especially dimethylamino.

With regard to compounds of the formulae (Ia), (Ib), (Ic) and (Id), $A^1$ is preferably fluorine or $CF_3$; $A^2$ is preferably $CF_3$; and $A^3$ is preferably fluorine.

As used herein, the term "alkyl" or "alkoxy" as a group or part of a group means that the group is straight or branched. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy.

The cycloalkyl groups referred to herein may represent, for example, cyclopropyl, cyclobutyl, cyclopentyl or cyclohexyl. A suitable cycloalkylalkyl group may be, for example, cyclopropylmethyl.

As used herein, the terms "alkenyl" and "alkynyl" as a group or part of a group means that the group is straight or branched. Examples of suitable alkenyl groups include vinyl and allyl. A suitable alkynyl group is propargyl.

When used herein the term halogen means fluorine, chlorine, bromine and iodine. The most apt halogens are fluorine and chlorine of which fluorine is preferred.

Specific compounds within the scope of this invention include:

2-(R)-(1-(R)-(3,5-bis(trifluoromethyl)phenyl) ethoxy)-4-(2,3-dihydro-5-(N,N-dimethylamino)methyl-2-oxo-1,3-imidazol-4-yl)methyl-3-(S)-(4-fluorophenyl) morpholine;

4-(2,3-dihydro-5-(N,N-dimethylamino)methyl-2-oxo-1,3-imidazol-4-yl)methyl-3-(S)-(4-fluorophenyl)-2-(R)-(1-(R)-(3-fluoro-5-(trifluoromethyl)phenyl) ethoxy)-morpholine;

3-(S)-(4-fluorophenyl)-2-(R)-(1-(R)-(3-fluoro-5-(trifluoromethyl)phenyl) ethoxy)-4-(2,3-dihydro-2-oxo-5-pyrrolidinomethyl-1,3-imidazol-4-yl)methylmorpholine;

2-(R)-(1-(R)-(3,5-bis(trifluoromethyl)phenyl) ethoxy)-3-(S)-(4-fluorophenyl)-4-(2,3-dihydro-2-oxo-5-pyrrolidinomethyl-1,3-imidazol-4-yl)methylmorpholine;

2-(R)-(1-(R)-(3,5-bis(trifluoromethyl)phenyl) ethoxy)-3-(S)-(4-fluorophenyl)-4-(2,3-dihydro-5-(4-hydroxypiperidino)methyl-2-oxo-1,3-imidazol-4-yl)methylmorpholine;

3-(S)-(4-fluorophenyl)-2-(R)-(1-(R)-(3-fluoro-5-(trifluoromethyl)phenyl) ethoxy)-4-(2,3-dihydro-5-morpholinomethyl-2-oxo -1,3-imidazol-4-yl)methylmorpholine;

2-(R)-(1-(R)-(3,5-bis(trifluoromethyl)phenyl) ethoxy)-3-(S)-(4-fluorophenyl)-4-(2,3-dihydro-5-morpholinomethyl-2-oxo-1,3-imidazol -4-yl)methylmorpholine;

4-(5-azetidinylmethyl-2,3-dihydro-2-oxo-1,3-imidazol-4-yl)methyl-2-(R)-(1-(R)-(3,5-bis(trifluoromethyl)phenyl)ethoxy)-3-(4-fluorophenyl) morpholine;

2-(R)-(1-(R)-(3,5-bis(trifluoromethyl)phenyl) ethoxy)-3-(S)-(4-fluorophenyl)-4-(2,3-dihydro-5-(N-methylpiperazinyl)methyl-2-oxo-1,3-imidazol-4-yl)methylmorpholine;

2-(R)-(1-(R)-(3,5-bis(trifluoromethyl)phenyl) ethoxy)-3-(S)-(4-fluorophenyl)-4-(2,3-dihydro-5-(N-(2-morpholinoethyl)aminomethyl)-2-oxo-1,3-imidazol-4-yl)-methylmorpholine;

2-(R)-(1-(R)-(3,5-bis(trifluoromethyl)phenyl) ethoxy)-3-(S)-(4-fluorophenyl)-4-(2,3-dihydro-2-oxo-5-(N-(2-pyrrolidinoethyl) aminomethyl)-1,3-imidazol-4-yl)methylmorpholine;

2-(R)-(1-(R)-(3,5-bis(trifluoromethyl)phenyl) ethoxy)-4-(5-(dimethylamino) methyl-1,2,3-triazol-4-yl)methyl-3-(S)-(4-fluorophenyl)morpholine;

2-(R)-(1-(R)-(3,5-bis(trifluoromethyl)phenyl) ethoxy)-3-(S)-(4-fluorophenyl)-4-(N-(N'-methylaminoethyl)-1,2,4-triazol-3-yl) methylmorpholine;

and pharmaceutically acceptable salts or prodrugs thereof.

Further preferred compounds within the scope of the present invention include:

- 2-(R)-(1-(R)-(3,5-bis(trifluoromethyl)phenyl) ethoxy)-3-(S)-(4-fluorophenyl)-4-(5-(N-methylaminomethyl)-1,2,3-triazol-4-yl) methylmorpholine;
- 4-(5-aminomethyl)-1,2,3-triazol-4-yl) methyl-2-(R)-(1-(R)-(3,5-bis (trifluoromethyl)phenyl)ethoxy)-3-(S)-(4-fluorophenyl) morpholine;
- 2-(R)-(1-(R)-(3,5-bis(trifluoromethyl)phenyl) ethoxy)-3-(S)-(4-fluorophenyl)-4-(5-pyrrolidinomethyl)-1,2,3-triazol-4-yl) methylmorpholine;
- 4-(5-(azetidinylmethyl)-1,2,3-triazol-4-yl)methyl-3-(S)-(4-fluorophenyl)-2-(R)-(1-(R)-(3-fluoro-5-(trifluoromethyl)phenyl)ethoxy) morpholine;
- 3-(S)-(4-fluorophenyl)-2-(R)-(1-(R)-(3-fluoro-5-(trifluoromethyl)phenyl) ethoxy)-4-(5-(pyrrolidinomethyl)-1,2,3-triazol-4-yl)methylmorpholine;
- 3-(S)-(4-fluorophenyl)-2-(R)-(1-(R)-(3-fluoro-5-(trifluoromethyl)phenyl) ethoxy)-4-(5-(morpholinomethyl)-1,2,3-triazol-4-yl)methylmorpholine;
- 4-(5-(N,N-dimethylaminomethyl)-1,2,3-triazol-4-yl)methyl-3-(S)-(4-fluorophenyl)-2-(R)-(1-(R)-(3-(trifluoromethyl)phenyl)ethoxy) morpholine;
- 2-(R)-(1-(R)-(3,5-bis(trifluoromethyl)phenyl) ethoxy)-3-(S)-(4-fluorophenyl)-4-(5-(N'-methylpiperazinomethyl)-1,2,3-triazol-4-yl) methylmorpholine;
- 2-(R)-(1-(R)-(3,5-bis(trifluoromethyl)phenyl) ethoxy)-3-(S)-(4-(1-(2-pyrrolidinoethyl)-1,2,3-triazol-4-yl)methylmorpholine;
- 2-(R)-(1-(R)-(3,5-bis(trifluoromethyl)phenyl) ethoxy)-3-(S)-phenyl-4-(2-(2-pyrrolidinoethyl) -1,2,3-triazol-4-yl)methylmorpholine;
- 2-(R)-(1-(R)-(3,5-bis(trifluoromethyl)phenyl) ethoxy)-3-(S)-(4-fluorophenyl)-4-(5-(morpholinomethyl)-1,2,3-triazol-4-yl) methylmorpholine;
- 4-(5-azetidinylmethyl)-1,2,3-triazol-4-yl) methyl-2-(R)-(1-(R)-(3,5-bis(trifluoromethyl)phenyl) ethoxy)-3-(S)-4-fluorophenyl)morpholine;
- 2-(R)-(1-(R)-(3,5-bis(trifluoromethyl)phenyl) ethoxy)-3-(S)-(4-fluorophenyl)-4-(5-(pyrrolinomethyl)-1,2,3-triazol-4-yl)methylmorpholine;
- 2-(R)-(1-(R)-(3,5-bis(trifluoromethyl)phenyl) ethoxy)-4-(5-(bis(methoxyethyl)aminomethyl)-1,2,3-triazol-4-yl)-methyl-3-(S)-(4-fluorophenyl)morpholine;
- 2-(R)-(1-(R)-(3,5-bis(trifluoromethyl)phenyl) ethoxy)-4-(2-chloro-5-morpholinomethyl-1,3-imidazol-4-yl)methyl-3-(S)-(4-fluorophenyl) morpholine;
- 2-(R)-(1-(R)-(3,5-bis(trifluoromethyl)phenyl) ethoxy)-4-(5-(N,N-dimethylaminomethyl)-1,3-imidazol-4-yl)methyl-3-(S)-(4-fluorophenyl) morpholine;
- 2-(R)-(1-(R)-(3,5-bis(trifluoromethyl)phenyl) ethoxy)-4-(5-(N,N-dimethylaminomethyl)-1,2,4-triazol-3-yl)methyl-3-(S)-(4-fluorophenyl) morpholine;
- 2-(R)-(1-(R)-(3,5-bis(trifluoromethyl)phenyl) ethoxy)-4-(5-N-(2,2-dimethoxyethyl)-N -methylaminomethyl)-1,2,3-triazol-4-yl)methyl-3-(S) -phenylmorpholine;
- 2-(R)-(1-(R)-(3,5-bis(trifluoromethyl)phenyl) ethoxy)-4-(5-(2-methoxyethyl) aminomethyl-1,2,3-triazol-4-yl)-methyl-3-(S) -phenylmorpholine;
- 2-(R)-(1-(R)-(3,5-bis(trifluoromethyl)phenyl) ethoxy)-4-(5-(N-(2-methoxyethyl)-N-methyl) aminomethyl-1,2,3-triazol-4-yl)methyl-3-(S) -phenylmorpholine;
- 2-(R)-(1-(R)-(3,5-bis(trifluoromethyl)phenyl) ethoxy)-4-(5-(N-isopropyl-N-(2-methoxyethyl) aminomethyl-1,2,3-triazol-4-yl)methyl-3-(S) -phenylmorpholine;
- 2-(R)-(1-(R)-(3,5-bis(trifluoromethyl)phenyl) ethoxy)-4-(5-(N-cyclopropyl-N-(2-methoxyethyl) aminomethyl-1,2,3-triazol-4-yl)methyl-3-(S) -phenylmorpholine;
- 2-(R)-(1-(R)-(3,5-bis(trifluoromethyl)phenyl) ethoxy)-4-(5-N,N-dibutylaminomethyl-1,2,3-triazol-4-yl)methyl-3-(S)-phenylmorpholine;
- 2-(R)-(1-(R)-(3,5-bis(trifluoromethyl)phenyl) ethoxy)-4-(5-N,N-diisopropylaminomethyl-1,2,3-triazol-4-yl)methyl-3-(S)-phenylmorpholine;

and pharmaceutically acceptable salts or prodrugs thereof.

Yet further preferred compounds within the scope of the present invention include:

- 2-(R)-(1-(S)-(3,5-bis(trifluoromethyl)phenyl)-2-hydroxyethoxy)-3-(S)-(4-fluorophenyl)-4-(2,3-dihydro-3-oxo-1,2,4-triazol-5-yl) methylmorpholine;
- 2-(R)-(1-(S)-(3,5-bis(trifluoromethyl)phenyl)-2-hydroxyethoxy)-3-(S)-(4-fluorophenyl)-4-(1,2,4-triazol-3-yl)-methylmorpholine;
- 4-(2,3-dihydro-3-oxo-1,2,4-triazol-5-yl)methyl-3-(S)-(4-fluorophenyl)-2-(R)-(1-(S)-(3-fluoro-5-(trifluoromethyl)phenyl)-2-hydroxyethoxy)morpholine;
- 4-(2,3-dihydro-2-oxo-1,3-imidazol-4-yl)methyl-2-(R)-(1-(S)-(3,5-bis(trifluoromethyl) phenyl)-2-hydroxyethoxy)-3-(S)-(4-fluorophenyl) morpholine;
- 4-(2,3-dihydro-2-oxo-5-pyrrolidinomethyl -1,3-imidazol-4-yl)methyl-2-(R)-(1-(S)-(3,5-bis(trifluoromethyl)phenyl)-2-hydroxyethoxy)-3-(S) -(4-fluorophenyl)morpholine;
- 4-(2,3-dihydro-3-oxo-1,2,4-triazol-5-yl)-3-(S)-phenyl-2-(R)-(1-(S)-(3-(trifluoromethyl)phenyl)-2-hydroxyethoxy)morpholine;
- 4-(2,3-dihydro-3-oxo-1,2,4-triazol-5-yl)methyl-2-(R)-(1-(S)-(3-fluoro-5-(trifluoromethyl)phenyl)-2-hydroxyethoxy)-3-(S) -phenylmorpholine;
- 2-(R)-(1-(S)-(3,5-bis(trifluoromethyl)phenyl)-2-hydroxyethoxy)-4-(2,3-dihydro-3-oxo-1,2,4-triazol-5-yl)-3-(S) -phenylmethylmorpholine;
- 3-(S)-phenyl-4-(1,2,4-triazol-3-yl)-2-(R)-(1-(S)-3-(trifluoromethyl)phenyl)-2-hydroxyethoxy)morpholine;

and pharmaceutically acceptable salts or prodrugs thereof.

Further preferred compounds within the scope of the present invention are described in the Examples described herein.

In a further aspect of the present invention, the compounds of formula (I) will preferably be prepared in the form of a pharmaceutically acceptable salt, especially an acid addition salt.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulphonic acid, maleic acid, succinic acid, acetic acid, citric acid, tartaric acid, carbonic acid, phosphoric acid or sulphuric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

Thus, for example, certain preferred prodrugs may not be antagonists of tachykinin, particularly substance P, activity to any significant extent (or not at all). Such compounds, however, are still advantageous in treating the various conditions described herein, especially where an injectable formulation is preferred.

The advantages of a prodrug may lie in its physical properties, such as enhanced water solubility for parenteral administration compared with the parent drug, or it may enhance absorption from the digestive tract, or it may enhance drug stability for long-term storage. Ideally a prodrug will improve the overall efficacy of a parent drug, for example, through the reduction of toxicity and unwanted effects of drugs by controlling their absorption, blood levels, metabolism, distribution and cellular uptake.

A particularly preferred class of prodrugs of the compounds of the present invention is that wherein the hydroxyl moiety of the group Y in formula (I) (when Y if $C_{1-4}$alkyl substituted by hydroxyl) is derivatized.

It will be appreciated that a further class of prodrugs of the compounds of the present invention is that wherein the heterocyclic group represented by $R^6$ in formula (I) is derivatized, or alternatively, wherein both the hydroxyl moiety of the group Y (when Y is $C_{1-4}$alkyl substituted by hydroxyl) and the heterocyclic group represented by $R^6$ in formula (I) are derivatized.

Suitable prodrug derivatives include:

(a) —$(CHR^{10})_n$—PO(OH)O—.$M^+$;

(b) —$(CHR^{10})_n$—PO(O—)$_2$.2$M^+$;

(c) —$(CHR^{10})_n$—PO(O—)$_2$.$D^{2+}$;

(d) —$(CHR^{10})_n$—SO$_3$—.$M^+$;

(e) —COCH$_2$CH$_2$CO$_2$—.$M^+$;

(f) —COH;

(g) —CO(CH$_2$)$_n$N(R$^{10}$)$_2$; and (h) —$(CH(R^{10})O)_n$—COR$^{11}$, wherein n is zero or 1;

$M^+$ is a pharmaceutically acceptable monovalent counterion;

$D^{2+}$ is a pharmaceutically acceptable divalent counterion;

$R^{10}$ is hydrogen or $C_{1-3}$alkyl; and $R^{11}$ is a group selected from —O(CH$_2$)$_2$NH$_3^+$.$M^-$;

—O(CH$_2$)$_2$NH$_2$(R$^{12}$)$^+$.$M^-$; —OCH$_2$CO$_2^-$.$M^+$;

—OCH(CO$_2^-$.$M^+$)CH$_2$CO$_2^-$.$M^+$;

—OCH$_2$CH(NH$_3^{3\oplus}$)CO$_2^-$;

—OC(CO$_2^-$.$M^+$)(CH$_2$CO$_2^-$.$M^+$)$_2$; and

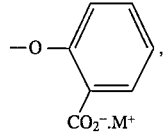

in which $M^-$ is a pharmaceutically acceptable monovalent counterion, and $R^{12}$ is hydrogen, $C_{1-4}$alkyl or $C_{2-4}$alkyl substituted by a hydroxyl or $C_{1-4}$alkoxy group.

Particularly preferred prodrug derivatives are:

(a) —$(CHR^{10})_n$—PO(OH)O$^-$.$M^+$;

(b) —$(CHR^{10})_n$—PO(O—)$_2$.2$M^+$;

(c) —$(CHR^{10})_n$—PO(O—)$_2$.$D^{2+}$;

especially where n is zero.

The term "parent molecule", "parent compound" or "parent drug" refers to the biologically active entity that is released via enzymatic action of a metabolic or catabolic process, or via a chemical process following administration of the prodrug. The parent compound may also be the starting material for the preparation of its corresponding prodrug.

While all of the usual routes of administration are useful with the above prodrugs, the preferred routes of administration are oral and intravenous. After gastrointestinal absorption or intravenous administration, the prodrugs are hydrolyzed or otherwise cleaved in vivo to the corresponding parent compounds of formula (I), or a pharmaceutically acceptable salt thereof. Since the parent compounds may less than optimally soluble in aqueous solutions, the above prodrugs provide a distinct advantage by virtue of their relatively enhanced aqueous solubility.

Examples of negative monovalent counterions defined herein as "$M^-$" include acetate, adipate, benzoate, benzenesulfonate, bisulfate, butyrate, camphorate, camphorsulfonate, citrate, ethanesulfonate, fumarate, hemisulfate, 2-hydroxyethylsulfonate, heptanoate, hexanoate, hydrochloride, hydrobromide, hydroiodide, lactate, malate, maleate, methanesulfonate, 2-naphthalenesulfonate, oxalate, pamoate, persulfate, picrate, pivalate, propionate, salicylate, stearate, succinate, sulfate, tartrate, tosylate (p-toluenesulfonate), and undecanoate.

Base salts (which are pharmaceutically acceptable monovalent cations defined herein as "$M^+$" or pharmaceutically acceptable divalent cations defined herein as "$D^{2+}$", if appropriate) include ammonium salts, alkali metal salts such as sodium, lithium and potassium salts, alkaline earth metal salts such as aluminium, calcium and magnesium salts, salts with organic bases such as dicyclohexylamine salts, N-methyl-D-glucamine, and salts with amino acids such as arginine, lysine, ornithine, and so forth. If $M^+$ is a monovalent cation, it is recognised that if the definition 2$M^+$ is present, each of $M^+$ may be the same or different. In addition, it is similarly recognised that if the definition 2$M^+$ is present, a divalent cation $D^{2+}$ may instead be present. Also, the basic nitrogen-containing groups may be quaternized with such agents as: lower alkyl halides, such as methyl, ethyl, propyl, and butyl chlorides, bromides and iodides; dialkyl sulfates like dimethyl, diethyl and dibutyl; diamyl sulfates; long chain halides such as decyl, lauryl, myristyl and stearyl chlorides, bromides and iodides; aralkyl halides like benzyl bromide and others. The non-toxic physiologically acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

A particularly preferred sub-class of prodrugs of the compounds of the present invention is that defined by the formula (Ie) and pharmaceutically acceptable salts thereof:

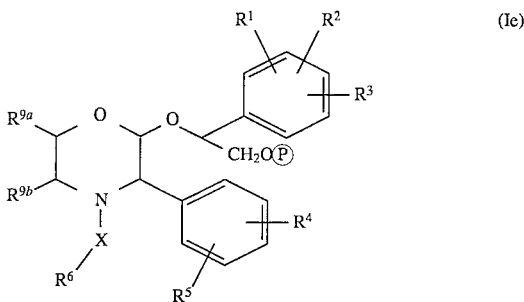

(Ie)

wherein $R^1$, $R^2$, $R^3$, $R^4$, $R^5$, $R^6$, $R^{9a}$, $R^{9b}$ and X are as defined in relation to formula (I) and P in a circle is $PO(OH)O—.M^+$, $PO(O—)_2.2M^+$, or $PO(O—)_2.D^{2+}$.

Another preferred sub-class of prodrugs of the compounds of the present invention is that defined by the formula (If) and pharmaceutically acceptable salts thereof:

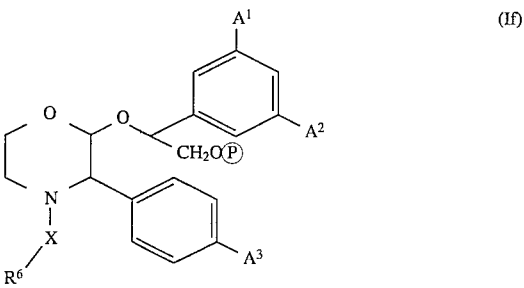

(If)

wherein $A^1$, $A^2$ and $A^3$ are as defined in relation to formula (Ia), X and $R^6$ are as defined in relation to formula (I), and P in a circle is $PO(OH)O—.M^+$, $PO(O—)_2.2M^+$, or $PO(O—)_2.D^{2+}$.

An especially preferred sub-group of prodrugs of the compounds of the present invention is that defined by formula (Ig) and pharmaceutically acceptable salts thereof:

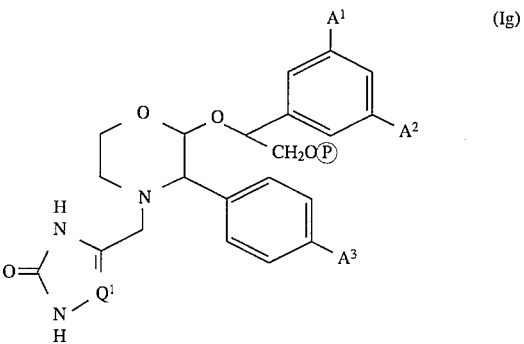

(Ig)

wherein $A^1$, $A^2$ and $A^3$ are as defined in relation to formula (Ia), $Q^1$ is as defined in relation to formula (Ic) and P in a circle is $PO(OH)O—.M^+$, $PO(O—)_2.2M^+$, or $PO(O—)_2.D^{2+}$.

A yet further preferred sub-group of prodrugs of the compounds of the present invention is that defined by formula (Ih) and pharmaceutically acceptable salts thereof:

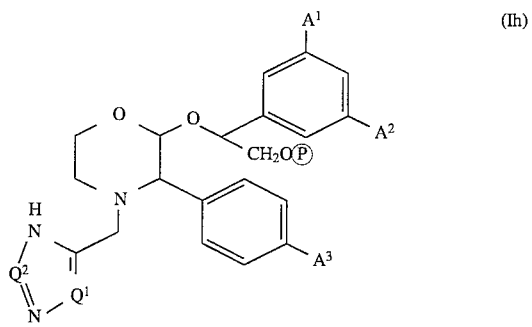

(Ih)

wherein $A^1$, $A^2$ and $A^3$ are as defined in relation to formula (Ia), $Q^1$ and $Q^2$ are as defined in relation to formulae (Ic) and (Id), respectively, and P in a circle is $PO(OH)O—.M^+$, $PO(O—)_2.2M^+$, or $PO(O—)_2.D^{2+}$.

Specific prodrug derivatives within the scope of this invention include:

2-(R)-(1-(S)-(3,5-bis(trifluoromethyl)phenyl)-2-phosphoryloxyethoxy)-3-(S)-(4-fluorophenyl)-4-(2,3-dihydro-3-oxo-1,2,4-triazol-5-yl) methylmorpholine;

2-(R)-(1-(S)-(3,5-bis(trifluoromethyl)phenyl)-2-phosphoryloxyethoxy)-3-(S)-(4-fluorophenyl)-4-(1,2,4-triazol-3-yl)methylmorpholine;

4-(2,3-dihydro-3-oxo-1,2,4-triazol-5-yl)methyl-2-(R)-(1-(S)-3-fluoro-5-(trifluoromethyl)phenyl)-2-phosphoryloxyethoxy)-3-(S) -phenylmorpholine;

2-(R)-(1-(S)-(3,5-bis(trifluoromethyl)phenyl)-2-phosphoryloxyethoxy)-4-(2,3-dihydro-3-oxo-1,2,4-triazol-5-yl)methyl-3-(S)-phenylmorpholine;

and pharmaceutically acceptable salts thereof.

With regard to compounds of the formulae (If), (Ig) and (Ih), $A^1$ is preferably fluorine or $CF_3$; $A^2$ is preferably $CF_3$; and $A^3$ is preferably fluorine.

The present invention includes within its scope solvates of the compounds of formula (I) and salts thereof, for example, hydrates.

The compounds according to the invention have at least three asymmetric centres, and may accordingly exist both as enantiomers and as diastereoisomers. It is to be understood that all such isomers and mixtures thereof are encompassed within the scope of the present invention.

The preferred compounds of the formula (I), (Ia), (Ib), (Ic), (Id), (Ie), (If), (Ig) and (Ih) will have the 2- and 3- substituent cis and the preferred stereochemistry at the 2-position is that possessed by the compound of Example 1 (i.e. 2-(R)-), the preferred stereochemistry of the 3-position is that possessed by the compound of Example 1 (i.e. 3-(S)), and the preferred stereochemistry of the carbon to which the group Y is either (R) when Y is $C_{1-4}$alkyl (e.g. methyl) or (S) when Y is $C_{1-4}$alkyl substituted by hydroxy (e.g. $CH_2OH$). Thus for example as shown in formula (Ii)

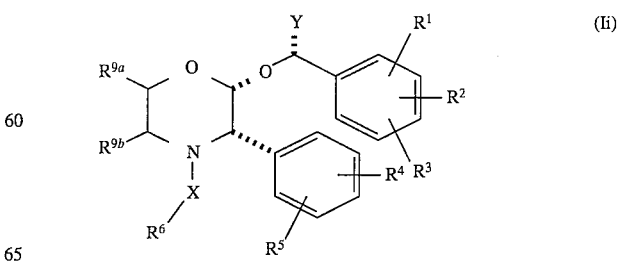

(Ii)

The present invention further provides pharmaceutical compositions comprising one or more compounds of formula (I) in association with a pharmaceutically acceptable carrier.

Preferably the compositions according to the invention are in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Preferred compositions for administration by injection include those comprising a compound of formula (I), as the active ingredient, in association with a surface-active agent (or wetting agent or surfactant) or in the form of an emulsion (as a water-in-oil or oil-in-water emulsion).

Suitable surface-active agents include anionic agents such as sodium bis-(2-ethylhexyl)sulfosuccinate (docusate sodium), cationic agents, such as alkyltrimethylammonium bromides, (e.g. cetyltrimethylammonium bromide (cetrimide)), and in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and preferably between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example gylcerol or glucose, to adjust the tonicity of the emulsion. Suitable emulsions will typically contain up to 20% oil, for example, between 5 and 20%. The fat emulsion will preferably comprise fat droplets between 0.1 and 1.0 µm, particularly 0.1 and 0.51 µm, and have a pH in the range of 5.5 to 8.0.

Particularly preferred emulsion compositions are those prepared by mixing a compound of formula (I) with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The present invention futher provides a process for the preparation of a pharmaceutical composition comprising a compound of formula (I), which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity. These may include disorders of the central nervous system such as anxiety, depression, psychosis and schizophrenia; epilepsy; neurodegenerative disorders such as dementia, including senile dementia of the Alzheimer type, Alzheimer's disease and Down's syndrome; demyelinating diseases such as MS and ALS and other neuropathological disorders such as peripheral neuropathy, for example diabetic and chemotherapy-induced neuropathy, and postherpetic and other neuralgias; small cell carcinomas such as small cell lung cancer; respiratory diseases, particularly those associated with excess mucus secretion such as chronic obstructive airways disease, bronchopneumonia, chronic bronchitis, cystic fibrosis and asthma, and bronchospasm; inflammatory diseases such as inflammatory bowel disease, psoriasis, fibrositis, osteoarthritis, rheumatoid arthritis, pruritis and sunburn; allergies such as eczema and rhinitis; hypersensitivity disorders such as poison ivy; ophthalmic diseases such as conjunctivitis, vernal conjunctivitis, and the like; ophthalmic conditions associated with cell proliferation such as proliferative vitreoretinopathy; cutaneous diseases such as contact clermatitis, atopic dermatitis, urticaria, and other eczematoid dermatitis; addiction disorders such as alcoholism; stress related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosus; gastrointestinal (GI) disorders and diseases of the GI tract such as disorders associated with the neuronal control of viscera, ulcerative coliris, Crohn's disease, irritable bowel syndrome and emesis, including acute, delayed or anticipatory emesis such as emesis induced by chemotherapy, radiation, toxins, viral or bacterial infections, pregnancy, vestibular disorders, motion, surgery, migraine, and variations in intercranial pressure, in particular, for example, drug or radiation induced emesis or postoperative nausea and vomiting; disorders of blaclder function such as cystiris, bladder detrusor hyper-reflexia and incontinence; fibrosing and collagen diseases such as scleroderma ancl eosinophilic fascioliasis; disorders of blood flow caused by vasodilation and vasospastic diseases such as angina, migraine and Reynaud's disease; and pain or nociception, for example, that attributable to or associated with any of the foregoing conditions, especially the transmission of pain in migraine.

The compounds of formula (I) are also of value in the treatment of a combination of the above conditions, in particular in the treatment of combined post-operative pain and post-operative nausea and vomiting.

The compounds of formula (I) are particularly useful in the treatment of emesis, including acute, delayed or anticipatory emesis, such as emesis induced by chemotherapy, radiation, toxins, pregnancy, vestibular disorders, motion, surgery, migraine, and variations in intercranial pressure. Most especially, the compounds of formula (I) are of use in the treatment of emesis induced by antineoplastic (cytotoxic) agents including those routinely used in cancer chemotherapy.

Examples of such chemotherapeutic agents include alkylating agents, for example, nitrogen mustards, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of poclophyllotoxin; and cytotoxic antibiotics.

Particular examples of chemotherapeutic agents are described, for instance, by D. J. Stewart in *Nausea and Vomiting: Recent Research and Clinical Advances,* Eds. J. Kucharczyk et al, CRC Press Inc., Boca Raton, Fla., USA (1991) pages 177–203, especially page 188. Commonly used chemotherapeutic agents include cisplatin, dacarbazine (DTIC), dactinomycin, mechlorethamine (nitrogen mustard), streptozocin, cyclophosphamide, carmustine (BCNU), Iomustine (CCNU), doxorubicin (adriamycin), daunorubicin, procarlaazine, mitomycin, cytarabine, etoposide, methotrexate, 5-fluorouracil, vinblastine, vincristine, bleomycin and chlorambucil [R. J. Gralla et al in *Cancer Treatment Reports* (1984) 68(1), 163–172].

The compounds of formula (I) are also of use in the treatment of emesis induced by radiation including radiation therapy such as in the treatment of cancer, or radiation sickness; and in the treatment of post-operative nausea and vomiting.

It will be appreciated that the compounds of formula (I) may be presented together with another therapeutic agent as a combined preparation for simultaneous, separate or sequential use for the relief of emesis. Such combined preparations may be, for example, in the form of a twin pack.

A further aspect of the present invention comprises the compounds of formula (I) in combination with a 5-HT$_3$ antagonist, such as ondansetron, granisetron or tropisetron, or other anti-emetic medicaments, for example, a dopamine antagonist such as metoclopramide. Additionally, a compound of formula (I) may be administered in combination with an anti-inflammatory corticosteroid, such as dexamethasone. Furthermore, a compound of formula (I) may be administered in combination with a chemotherapeutic agent such as an alkylating agent, antimetabolite, mitotic inhibitor or cytotoxic antibiotic, as described above. In general, the currently available dosage forms of the known therapeutic agents for use in such combinations will be suitable.

When tested in the ferret model of cisplatin-induced emesis described by F. D. Tattersall et al, in *Eur. J. Pharmacol.,* (1993) 250, R5–R6, the compounds of the present invention were found to attenuate the retching and vomiting induced by cisplatin.

The compounds of formula (I) are also particularly useful in the treatment of pain or nociception and/or inflammation and disorders associated therewith such as, for example, neuropathy, such as diabetic and chemotherapy-induced neuropathy, postherpetic and other neuralgias, asthma, osteroarthritis, rheumatoid arthritis and especially migraine.

The present invention further provides a compound of formula (I) for use in therapy.

According to a further or alternative aspect, the present invention provides a compound of formula (I) for use in the manufacture of a medicament for the treatment of physiological disorders associated with an excess of tachykinins, especially substance P.

The present invention also provides a method for the the treatment or prevention of physiological disorders associated with an excess of tachykinins, especially substance P, which method comprises administration to a patient in need thereof of a tachykinin reducing amount of a compound of formula (I) or a composition comprising a compound of formula (I).

For the treatment of certain conditions it may be desirable to employ a compound according to the present invention in conjunction with another pharmacologically active agent. For example, for the treatment of respiratory diseases such as asthma, a compound of formula (I) may be used in conjunction with a bronchodilator, such as a $\beta_2$-adrenergic receptor antagonist or tachykinin antagonist which acts at NK-2 receptors. The compound of formula (I) and the bronchodilator may be administered to a patient simultaneously, sequentially or in combination.

The present invention accordingly provides a method for the treatment of a respiratory disease, such as asthma, which method comprises administration to a patient in need thereof of an effective amount of a compound of formula (I) and an effective amount of a bronchodilator.

The present invention also provides a composition comprising a compound of formula (I), a bronchodilator, and a pharmaceutically acceptable carrier.

The excellent pharmacological profile of the compounds of the present invention offers the opportunity for their use in therapy at low doses thereby minimising the risk of unwanted side effects.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

In the treatment of emesis using an injectable formulation, a suitable dosage level is about 0.001 to 10 mg/kg per day, preferably about 0.005 to 5 mg/kg per day, and especially 0.01 to 2 mg/kg per day. The compounds may be administered on a regimen of 1 to 4 times per day, preferably once or twice per day.

It will be appreciated that the amount of a compound of formula (I) required for use in any treatment will vary not only with the particular compounds or composition selected but also with the route of administration, the nature of the condition being treated, and the age and condition of the patient, and will ultimately be at the discretion of the attendant physician.

According to a general process (A), the compounds according to the invention may be prepared from compounds of formula (II)

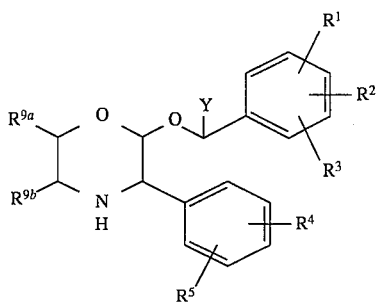

wherein $R^1$, $R^2$, $R^3$, $R^4$, $R^5$ and Y are as defined in relation to formula (I) by reaction with a compound of formula (III):

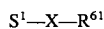

where X is as defined in relation to formula (I), $R^{6a}$ is a group of the formula $R^6$ as defined in relation to formula (Ia) or a precursor therefor and $X^1$ is a leaving group such as bromine or chlorine; and, if $R^{6a}$ is a precursor group, converting it to a group $R^6$ (in which process any reactive group may be protected and thereafter deprotected if desired).

This reaction may be performed in conventional manner, for example in an organic solvent such as dimethylformamide in the presence of an acid acceptor such as potassium carbonate.

According to another process (B), compounds of formula (I) wherein $R^6$ represents 1,2,3-triazol-4-yl substituted by $CH_2NR^7R^8$ and X is —$CH_2$—, may be prepared by reaction of a compound of formula (IV)

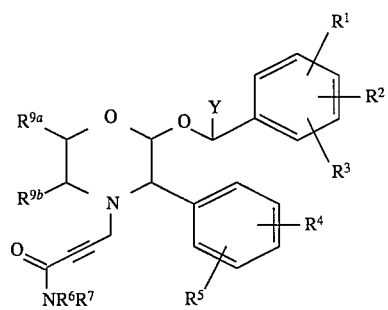

with an azide, for example, sodium azide in a suitable solvent such as dimethylsulphoxide at a temperature of between 40° C. and 100° C., followed by reduction of the carbonyl group adjacent to —$NR^7R^8$ using a suitable reducing agent such as lithium aluminium hydride at at a temperature between −10° C. and room temperature, conveniently at room temperature.

Alternatively, according to a process (C), compounds of formula (I) wherein $R^6$ represents 1,2,3-triazol-4-yl substituted by $CH_2NR^7R^8$, and X is —$CH_2$—, may be prepared by reaction of a compound of formula (V)

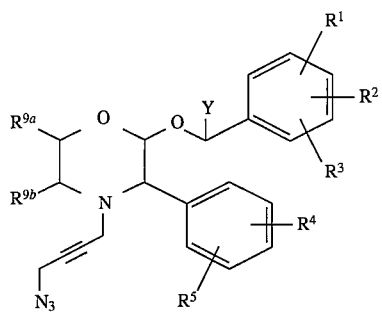

with an amine of formula $NHR^7R^8$, in a suitable solvent such as an ether, for example, dioxan, at elevated temperature, for example, between 50° C. and 100° C., in a sealed tube, or the like. This reaction is based upon that described in *Chemische Berichte* (1989) 122, p. 1963.

According to another process, (D), compounds of formula (I) wherein $R^6$ represents substituted or unsubstituted 1,3,5-triazine may be prepared by reaction of intermediates of formula (VI):

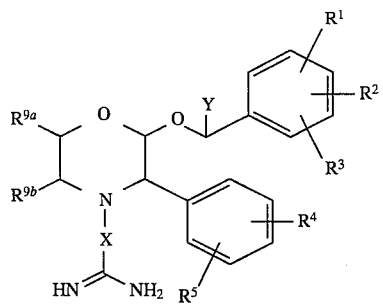

with substituted or unsubstituted 1,3,5-triazine.

The reaction is conveniently effected in a suitable organic solvent, such as acetonitrile, at elevated temperature, such as 80°–90° C., preferably about 82° C.

According to a further process, (E), compounds of formula (I) wherein $R^6$ represents substituted or unsubstituted 1,2,4-triazine may be prepared by reaction of an intermediate of formula (VII) with a dicarbonyl compound of formula (VIII):

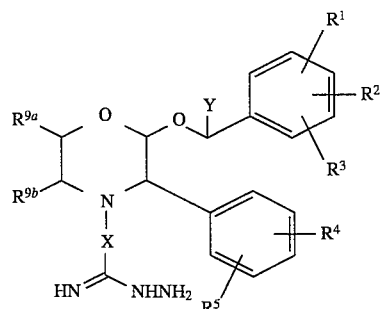

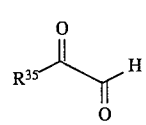

wherein $R^{35}$ represents H or a suitable substituent such as $ZNR^7R^8$.

The reaction is conveniently effected in a suitable organic solvent, such as an ether, e.g. tetrahydrofuran, conveniently at ambient temperature.

According to a further process (F), compounds of formula (I) wherein $R^6$ represents a substituted 1,2,4-triazolyl group may be prepared by reaction of an intermediate of formula (II) with a compound of formula (IX)

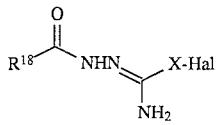
(IX)

wherein X is as defined in relation to formula (I), Hal is a halogen atom, for example, bromine, chlorine or iodine and $R^{18}$ is H, $CONH_2$ or $OCH_3$ (which is converted to an oxo substituent under the reaction conditions), in the presence of a base, followed where necessary by conversion to a compound of formula (I), for example, by reduction of the $CONH_2$ group to $CH_2NH_2$.

Suitable bases of use in the reaction include alkali metal carbonates such as, for example, potassium carbonate. The reaction is conveniently effected in an anhydrous organic solvent such as, for example, anhydrous dimethylformamide, preferably at elevated temperature, such as about 140° C.

A suitable reducing agent for the group $CONH_2$ is lithium aluminium hydride, used at between −10° C. and room temperature.

According to another process, (G), compounds of formula (I) wherein $R^6$ represents thioxotriazolyl may be prepared from intermediates of formula (X)

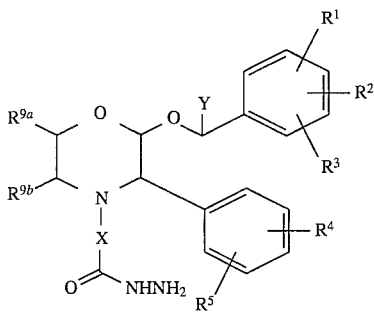
(X)

by reaction with a compound of formula HNCS, in the presence of a base.

Suitable bases of use in the reaction include organic bases such as, for example, 1,8-diazabicyclo[5.4.0]undec-7-ene (DBU). The reaction is conveniently effected in a suitable organic solvent, such as alcohol, e.g. butanol.

Further details of suitable procedures will be found in the accompanying Examples.

Compounds of formula (I) may also be prepared from other compounds of formula (I) using suitable interconversion procedures. For example, compounds of formula (I) wherein X represents $C_{1-4}$alkyl may be prepared from compounds of formula (I) wherein X represents $C_{1-4}$alkyl substituted by oxo by reduction, for example, using borane or lithium aluminium hydride. Suitable interconversion procedures will be readily apparent to those skilled in the art.

Intermediates of formula (IV) may be prepared from intermediates of formula (II) by reaction with an acetylene compound of formula $HC{\equiv}C-CH_2$-Hal in the presence of a base such as potassium carbonate in a suitable solvent such as dimethylformamide, conveniently at room temperature, followed by reaction of the resultant acetylene intermediate with an amide of formula $Hal-CO-NR^7R^8$ in the presence of suitable catalysts including bis(triphenylphosphine) palladium(II) chloride, copper(I) iodide and triphenylphosphine in a suitable solvent such as triethylamine, preferably at reflux.

Intermediates of formula (V) may be prepared from a compound of formula (XI)

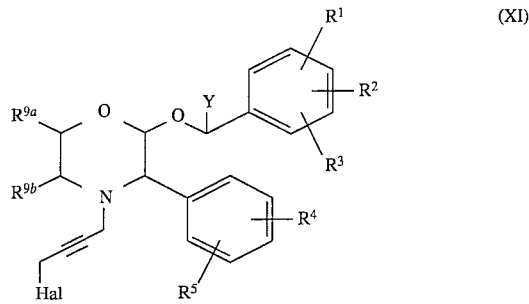
(XI)

wherein Hal is a halogen atom, for example, chlorine, bromine or iodine, especially chlorine, by reaction with an azide, for example, sodium azide in a suitable solvent such as dimethylsulphoxide at or below room temperature.

Compounds of formula (XI) may be prepared by a dropwise addition of an intermediate of formula (II) to a dihaloacetytene of formula $Hal-CH_2-C{\equiv}C-CH_2-Hal$ where each Hal is independently chlorine, bromine or iodine, especially chlorine. The reaction is conveniently effected in a suitable solvent such as dimethylformamide in the presence of a base such as potassium carbonate.

Intermediates of formula (VI) may be prepared from intermediates of formula (II) by reaction with a compound of formula $Hal-X-C(NH)NH_2$, where Hal and X are as previously defined.

Intermecliates of formula (VII) may be prepared from intermediates of formula (II) by reaction with a compound of formula Hal—X—C(NH)NHNH—Boc, wherein Hal and X are as previously defined and Boc stands for t-butoxycarbonyl, followed by deprotection under acidic conditions.

Compounds of formula (VIII) are commercially available or may be prepared from commercially available compounds by known methods.

Compounds of formula (IX) may be prepared as described in *J. Med. Chem.*, (1984) 27, 849.

Intermediates of formula (X) may be prepared from the corresponding ester by treatment with hydrazine. The reaction is conveniently effected in a suitable organic solvent, such as an alcohol, for example, ethanol, at elevated temerpature.

For compounds wherein $R^6$ is a heterocycle substituted by a $ZNR^7R^8$ group where Z is $CH_2$, certain favoured compounds of formula (I) may be prepared from a corresponding compound with a hydrogen atom in place of the $ZNR^7R^8$. Thus, for example a compound of the formula (I) wherein $R^6$ is an imidazolinone group carrying a $CH_2NR^7R^8$ moiety may be prepared from a corresponding compound lacking the $CH_2NR^7R^8$ moiety by reaction with formaldehyde and an amine $NHR^7R^8$ under conventional Mannich reaction conditions, for example in methanol with heating. If desired a pre-formed reagent such as $R^7R^8N^+{=}CH_2.I^-$ may be employed and a tertiary amine such as triethylamine used as acid acceptor.

Alternatively a compound of formula (I) wherein $R^6$ is an imidazolinone group lacking a $CH_2NR^7R^8$ may be reacted with paraformaldehyde and an amine for example a secondary amine such as pyrrolidine to give a compound wherein the imidazolinone ring is substituted by $CH_2NR^7R^8$ where $R^7$, $R^8$ and the nitrogen atom to which they are attached form a heteroaliphatic ring of 4 to 7 ring atoms which may optionally contain an oxygen ring atom or a second nitrogen atom which will be part of a NH or $NR^c$ moiety, where $R^c$ is as previously defined.

This reaction may be performed in a conventional manner, for instance, in a suitable solvent such as an alcohol, for example, methanol at an elevated temperature up to the boiling point of the solvent.

A further alternative method for the preparation of certain compounds of formula (I) involves the reaction of an intermediate of formula (II) as defined above with one of the compounds of formula (XII):

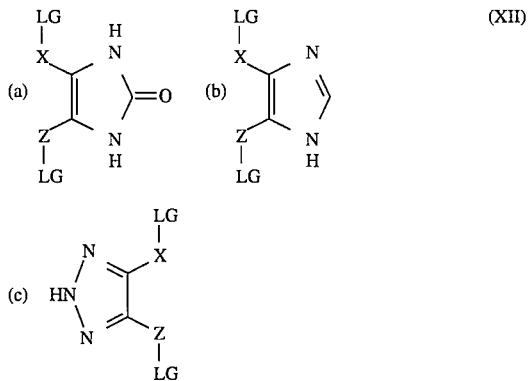

wherein each LG, which may be the same or different, is a leaving group, such as an alkyl- or arylsulphonyloxy group (e.g. mesylate or tosylate) or, in particular, a halogen atom, (e.g. bromine, chlorine or iodine) and X and Z are as defined in formula (I), followed by reaction of the resultant compound with an amine $NHR^7R^8$ to complete the $ZNR^7R^8$ moiety.

This reaction is conveniently effected in an organic solvent such as dimethylformamide in the presence of an acid acceptor such as potassium carbonate.

It will be appreciated that, where necessary, reactive groups may be protected, thus for example, the NH groups of an imidazolinone of formula (XIIa) may be protected by any suitable amine protecting group such as an acetyl group.

The preferred phosphate prodrugs of the compounds of the present invention may be prepared in a stepwise manner from a compound of formula (I) wherein Y is, for example, —$CH_2OH$—.

Thus, the hydroxy compound is first treated with dibenzyloxydiethylaminophosphine in a suitable solvent such as tetrahydrofuran, preferably in the presence of an acid catalyst such as tetrazole. The resultant compound ($Y=CH_2OP(OCH_2Ph)_2$) is then oxidised using, for example, 4-methylmorpholine-N-oxide to give the dibenzyl-protected phosphate. Deprotection by catalytic hydrogenation or transfer hydrogenation (palladium catalyst on carbon and ammonium formate), in a suitable solvent such as methanol at reflux, yields the desired phosphate prodrug which may be converted to any desired salt form by conventional methodology.

In an alternative two-step method, the hydroxy compound of formula (I) may be reacted with a suitable base such as sodium hydride in tetrahydrofuran, and tetrabenzylpyrophosphate added to yield the dibenzyl-protected phosphate which may be deprotected as described above.

The compounds of the formula (II) may be prepared as shown in the following Scheme in which $Ar^1$ represents the $R^1$, $R^2$, $R^3$ substituted phenyl group; $Ar^2$ represents the $R^4$, $R^5$ substituted phenyl group and Ph represents phenyl:

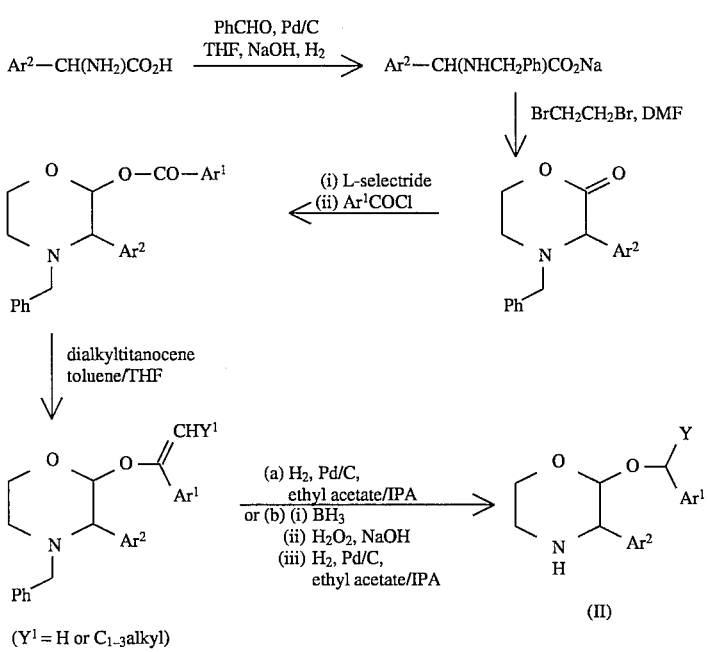

L-Selectride is lithium tri-sec-butylborohydride.

The following references describe methods which may be applied by the skilled worker to the chemical synthesis set forth above once the skilled worker has read the disclosure herein:

(i) D. A. Evans et al., *J. Am. Chem. Soc.*, (1990) 112, 4011.
(ii) I. Yanagisawa et al., *J. Med. Chem.*, (1984) 27, 849.
(iii) R. Duschinsky et al., *J. Am. Chem. Soc.*, (1948) 70, 657.
(iv) F. N. Tebbe et al., *J. Am. Chem. Soc.*, (1978) 100, 3611.
(v) N. A. Petasis et al., *J. Am. Chem. Soc.*, (1990) 112, 6532.
(vi) K. Takai et al., *J. Org. Chem.*, (1987) 52, 4412.

The Examples disclosed herein produce predominently the preferred isomers. The unfavoured isomers are also produced as minor components. If desired they may be isolated and employed to prepare the various stereoisomers in conventional manner, for example chromatography using an appropriate column. However, the skilled worker will appreciate that although the Examples have been optimized to the production of the preferred isomers, variation in solvent, reagents, chromatography etc can be readily employed to yield the other isomers.

It will be appreciated that compounds of the formula (I) wherein $R^6$ contains an =O or =S substituent can exist in tautomeric forms. All such tautomeric forms and mixtures thereof are included within this invention. Most aptly the =O or =S substituent in $R^6$ is the =O substituent.

Where they are not commercially available, the intermediates of formula (III) above may be prepared by the procedures described in the accompanying Examples or by alternative procedures which will be readily apparent to one skilled in the art.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The exemplified compounds of this invention were tested by the methods set out at pages 36 to 39 of International Patent Specification No. WO 93/01165. The compounds or, in the case of prodrugs, the parent compounds, were found to be active with $IC_{50}$ at the $NK_1$ receptor of less than 10 nM on said test method.

DESCRIPTION 1

(S)-(4-Fluorophenyl)glycine

Via Chiral Synthesis:

Step A: 3-(4-Fluorophenyl)acetyl-4-(S)-benzyl-2-oxazolidinone

An oven-dried, 1 L 3-necked flask, equipped with a septum, nitrogen inlet, thermometer, and a magnetic stirring bar, was flushed with nitrogen and charged with a solution of 5.09 g (33.0 mmol) of 4-fluorophenylacetic acid in 100 ml of anhydrous ether. The solution was cooled to −10° C. and treated with 5.60 ml (40.0 mmol) of triethylamine followed by 4.30 ml (35.0 mmol) of trimethylacetyl chloride. A white precipitate formed immediately. The resulting mixture was stirred at −10° C. for 40 minutes, then cooled to −78° C.

An oven-dried, 250 ml round bottom flask, equipped with a septum and a magnetic stirring bar, was flushed with nitrogen and charged with a solution of 5.31 g (30.0 mmol) of 4-(S)-benzyl-2-oxazolidinone in 40 ml of dry THF. The solution was stirred in a dry ice/acetone bath for 10 minutes, then 18.8 ml of 1.6M n-butyllithium solution in hexanes was slowly added. After 10 minutes, the lithiated oxazolidinone solution was added, via cannula, to the above mixture in the 3-necked flask. The cooling bath was removed from the resulting mixture and the temperature was allowed to rise to 0° C. The reaction was quenched with 100 ml of saturated aqueous ammonium chloride solution, transferred to a 1 l flask, and the ether and THF were removed in vacuo. The concentrated mixture was partitioned between 300 ml of methylene chloride and 50 ml of water and the layers were separated. The organic layer was washed with 100 ml of 2N aqueous hydrochloric acid solution, 300 ml of saturated aqueous sodium bicarbonate solution, dried over magnesium sulfate and concentrated in vacuo. Flash chromatography on 400 g of silica gel using 3:2 v/v hexanes/ether as the eluant afforded 8.95 g of an oil that slowly solidified on standing. Recrystallisation from 10:1 hexanes/ether afforded 7.89 g (83%) of the title compound as a white solid: mp 64°–66° C. MS (FAB): m/z 314 ($M^+$+H, 100%), 177 (M-ArCH$_2$CO+H, 85%). $^1$H NMR (400 MHz, CDCl$_3$) δ 2.76 (1H, dd, J=13.2, 9.2), 3.26 (dd, J=13.2, 3.2), 4.16–4.34 (4H, m), 4.65 (1H, m), 7.02–7.33 (9H, m). Anal. Calcd for $C_{18}H_{16}FNO_3$; C, 69.00; H, 5.15; N, 4.47; F, 6.06; Found: C, 68.86; H, 5.14; N, 4.48; F, 6.08.

Step B: 3-((S)-Azido-(4-fluorophenyl))acetyl-4-(S)-benzyl-2-oxazolidinone

An oven-dried, 1 l 3-necked flask, equipped with a septum, nitrogen inlet, thermometer, and a magnetic stirring bar, was flushed with nitrogen and charged with a solution of 58.0 ml of 1M potassium bis(trimethyisilyl)amide solution in toluene and 85 ml of THF and was cooled to −78° C. An oven-dried 250 ml round-bottomed flask, equipped with a septum and a magnetic stirring bar, was flushed with nitrogen and charged with a solution of 7.20 g (23.0 mmol) of 3-(4-fluorophenyl)acetyl-4-(S)-benzyl-2-oxazolidinone (from Step A) in 40 ml of THF. The acyl oxazolidinone solution was stirred in a dry ice/acetone bath for 10 minutes, then transferred, via cannula, to the potassium bis(trimethylsilyl)amide solution at such a rate that the internal temperature of the mixture was maintained below −70° C. The acyl oxazolidinone flask was rinsed with 15 ml of THF and the rinse was added, via cannula, to the reaction mixture and the resulting mixture was stirred at −78° C. for 30 minutes. An oven-dried, 250 ml round-bottomed flask, equipped with a septum and a magnetic stirring bar, was flushed with nitrogen and charged with a solution of 10.89 g (35.0 mmol) of 2,4,6-triisopropylphenylsulfonyl azide in 40 ml of THF. The azide solution was stirred in a dry ice/acetone bath for 10 minutes, then transferred, via cannula, to the reaction mixture at such a rate that the internal temperature of the mixture was maintained below −70° C. After 2 minutes, the reaction was quenched with 6.0 ml of glacial acetic acid, the cooling bath was removed and the mixture was stirred at room temperature for 18 hours. The quenched reaction mixture was partitioned between 300 ml of ethyl acetate and 300 ml of 50% saturated aqueous sodium bicarbonate solution. The organic layer was separated, dried over magnesium sulfate, and concentrated in vacuo. Flash chromatography on 500 g of silica gel using 2:1 v/v, then 1:1 v/v hexanes/methylene chloride as the eluant afforded 5.45 g (67%) of the title compound as an oil. IR Spectrum (neat, cm$^{-1}$): 2104, 1781, 1702. $^1$H NMR (400 MHz, CDCl$_3$) δ 2.86 (1H, dd, J=13.2, 9.6), 3.40 (1H, dd, J=13.2, 3.2), 4.09–4.19 (2H, m), 4.62–4.68 (1H, m), 6.14 (1H, s), 7.07–7.47 (9H, m). Anal. Calcd. for $C_{18}H_{15}FN_4O_3$; C 61.01; H, 4.27; N, 15.81; F, 5.36; Found: C, 60.99; H, 4.19; N, 15.80; F, 5.34.

Step C: (S)-Azido-(4-fluorophenyl)acetic acid

A solution of 5.40 g (15.2 mmol) of 3-((S)-azido -(4-fluorophenyl))acetyl-4-(S)-benzyl-2-oxazolidinone (from Step B) in 200 ml of 3:1 v/v THF/water was stirred in an ice bath for 10 minutes. 1.28 g (30.4 mmol) of lithium hydroxide monohydrate was added in one portion and the resulting mixture was stirred cold for 30 minutes. The reaction mixture was partitioned between 100 ml of methylene chloride and 100 ml of 25% saturated aqueous sodium bicarbonate solution and the layers were separated. The aqueous layer was washed with 2×100 ml of methylene chloride and acidified to pH 2 with 2N aqueous hydrochloric acid solution. The resulting mixture was extracted with 2×100 ml of ethyl acetate; the extracts were combined, washed with 50 ml of saturated aqueous sodium chloride solution, dried over magnesium sulfate, and concentrated in vacuo to afford 2.30 g (77%) of the title compound as an oil that was used in the following step without further purification. IR Spectrum (neat, $cm^{-1}$): 2111, 1724. $^1H$ NMR (400 MHz, $CDCl_3$) δ 5.06 (1H, s), 7.08–7.45 (4H, m), 8.75 (1H, br s).

Step D: (S)-(4-Fluorophenyl)glycine

A mixture of 2.30 g (11.8 mmol) of (S)-azido-(4-fluorophenyl)acetic acid (from Step C), 250 mg 10% palladium on carbon catalyst and 160 ml 3:1 v/v water/acetic acid was stirred under an atmosphere of hydrogen for 18 hours. The reaction mixture was filtered through Celite and the flask and filter cake were rinsed well with ~1 l of 3:1 v/v water/acetic acid. The filtrate was concentrated in vacuo to about 50 ml of volume. 300 ml of toluene was added and the mixture concentrated to afford a solid. The solid was suspended in 1:1 v/v methanol/ether, filtered and dried to afford 1.99 g (100%) of the title compound. $^1H$ NMR (400 MHz, $D_2O+NaOD$) δ 3.97 (1H, s), 6.77 (2H, app t, J=8.8), 7.01 (2H, app t, J=5.6).

Via Resolution:

Step A': (4-Fluorophenyl)acetyl chloride

A solution of 150 g (0.974 mol) of 4-(fluorophenyl) acetic acid and 1 ml of N,N-dimethylformamide in 500 ml of toluene at 40° C. was treated with 20 ml of thionyl chloride and heated to 40° C. An additional 61.2 ml of thionyl chloride was added dropwise over 1.5 hours. After the addition, the solution was heated at 50° C. for 1 hour, the solvent was removed in vacuo and the residual oil was distilled at reduced pressure (1.5 mmHg) to afford 150.4 g (89.5%) of the title compound, bp=68°–70° C.

Step B': Methyl 2-bromo-3-(4-fluorophenyl) acetate

A mixture of 150.4 g (0.872 mol) of 4-(fluorophenyl) acetyl chloride (from Step A') and 174.5 g (1.09 mol) of bromine was irradiated at 40°–50° C. with a quartz lamp for 5 hours. The reaction mixture was added dropwise to 400 ml of methanol and the solution was stirred for 16 hours. The solvent was removed in vacuo and the residual oil was distilled at reduced pressure (1.5 mmHg) to afford 198.5 g (92%) of the title compound, bp=106°–110° C.

Step C': Methyl (±)-(4-fluorophenyl)glycine

A solution of 24.7 g (0.1 mol) of methyl 2-bromo-2-(4-fluorophenyl)acetate (from Step B') and 2.28 g (0.01 mol) of benzyl triethylammonium chloride in 25 ml of methanol was treated with 6.8 g (0.105 mol) of sodium azide and the resulting mixture was stirred for 20 hours at room temperature. The reaction mixture was filtered; the filtrate was diluted with 50 ml of methanol and hydrogenated in the presence of 0.5 g of 10% Pd/C at 50 psi for 1 hour. The solution was filtered and the solvent removed in vacuo. The residue was partitioned between 10% aqueous sodium carbonate solution and ethyl acetate. The organic phase was washed with water, saturated aqueous sodium chloride solution dried over magnesium sulfate and concentrated in vacuo to afford 9.8 g of the title compound as an oil.

Step D': Methyl (S)-(4-fluorophenyl)glycinate

A solution of 58.4 g of methyl (±) 4-(fluorophenyl) glycinate (from Step C') in 110 ml of 7:1 v/v ethanol/water was mixed with a solution of 28.6 g (0.0799 mol) of O,O'-(+)-dibenzoyltartaric acid ((+)-DBT) (28.6 g, 0.0799 mol) in 110 ml of 7:1 v/v ethanol:water and the resulting solution was allowed to age at room temperature. Ethyl acetate (220 ml) was added after crystallisation was complete and the resulting mixture was cooled to –20° C. and filtered to afford 32.4 g of methyl (S)-(4-fluorophenyl)glycinate, (+)-DBT salt (ee=93.2%). The mother liquors were concentrated in vacuo and the free base was liberated by partitioning between ethyl acetate and aqueous sodium carbonate solution. A solution of free base, so obtained, in 110 ml of 7:1 v/v ethanol/water was mixed with a solution of 28.6 g (0.0799 mol) of O,O'-(–) -dibenzoyltartaric acid ((–)-DBT) (28.6 g, 0.0799 mol) in 110 ml of 7:1 v/v ethanol:water and the resulting solution was allowed to age at room temperature. Ethyl acetate (220 ml) was added after crysallisation was complete and the resulting mixture was cooled to –20° C. and filtered to afford 47.0 g of methyl (R)-(4-fluorophenyl)glycinate, (–)-DBT salt (ee=75.8%). Recycling of the mother liquors and addition of (+)-DBT gave a second crop of 7.4 g of (S)-(4-fluorophenyl) glycinate, (+)-DBT salt (ee=96.4%). The two crops of the (S)-amino ester (39.8 g) were combined in 200 ml of 7:1 v/v ethanol/water, heated for 30 minutes and cooled to room temperature. Addition of ethyl acetate, cooling, and filtration afforded 31.7 g of (S)-(4 -fluorophenyl)glycinate, (+)-DBT salt (ee>98%). Enantiomeric excess was determined by chiral HPLC (Crownpak CR(+) 5% MeOH in aq $HClO_4$ pH2 1.5 ml/min 40° C. 200 nm). A mixture of 17.5 g of (S)-(4-fluorophenyl)glycinate, (+)-DBT salt and 32 ml of 5.5N HCl (32 ml) was heated at reflux for 1.5 hours. The reaction mixture was concentrated in vacuo and the residue was dissolved in 40 ml of water. The aqueous solution was washed (3×30 ml of ethyl acetate) and the layers were separated. The pH of the aqueous layer was adjusted to 7 using ammonium hydroxide and the precipitated solid was filtered to afford 7.4 g of the title compound (ee=98.8%).

DESCRIPTION 2

4-Benzyl-3-(S)-(4-fluorophenyl)-2-morpholinone

Step A: N-Benzyl-(S)-(4-fluorophenyl)glycine

A solution of 1.87 g (11.05 mmol) of (S)-(4-fluorophenyl)-glycine (from Description 1) and 1.12 ml (11.1 mmol) of benzaldehyde in 11.1 ml of 1N aqueous sodium hydroxide solution and 11 ml of methanol at 0° C. was treated with 165 mg (4.4 mmol) of sodium borohydride. The cooling bath was removed and the resulting mixture was stirred at room temperature for 30 minutes. Second portions of benzaldehyde (1.12 ml (11.1 mmol)) and sodium borohydride (165 mg (4.4 mmol) were added to the reaction mixture and stirring was continued for 1.5 hours. The reaction mixture was partitioned between 100 ml of ether and 50 ml of water and the layers were separated. The aqueous layer was separated and filtered to remove a small amount of insoluble material. The flitrate was acidified to pH 5 with 2N aqueous hydrochloric acid solution and the solid that had precipitated was filtered, rinsed well with water, then ether, and dried to afford 1.95 g of the title compound. $^1$H NMR (400 MHz, $D_2O$+NaOD) δ 3.33 (2H, AB q, J=8.4), 3.85 (1H, s), 6.79–7.16 (4H, m).

Step B: 4-Benzyl-3-(S)-(4-fluorophenyl)-2-morpholinone

A mixture of 1.95 g (7.5 mmol) of N-benzyl (S)-(4-fluorophenyl)glycine, 3.90 ml (22.5 mmol) of N,N-diisopropylethylamine, 6.50 ml (75.0 mmol) of 1,2-dibromoethane and 40 ml of N,N-dimethylformamide was stirred at 100° C. for 20 hours (dissolution of all solids occurred on warming). The reaction mixture was cooled and concentrated in vacuo. The residue was partitioned between 250 ml of ether and 100 ml of 0.5N potassium hydrogen sulfate solution and the layers were separated. The organic layer was washed with 100 ml of saturated aqueous sodium bicarbonate solution, 3×150 ml of water, dried over magnesium sulfate, and concentrated in vacuo. Flash chromatography on 125 g of silica gel using 3:1 v/v hexanes/ether as the eluant afforded 1.58 g (74%) of the title compound as an oil. $^1$H NMR (400 MHz, $CDCl_3$) δ 2.65 (1H, dt, J=3.2, 12.8), 3.00 (1H, dt, J=12.8, 2.8), 3.16 (1H, d, J=13.6), 3.76 (1H, d, J=13.6), 4.24 (1H, s), 4.37 (1H, dt, J=13.2, 3.2), 4.54 (1H, dt, J=2.8, 13.2), 7.07–7.56 (9H, m).

DESCRIPTION 3

4-Benzyl-2-(R)-(3,5-bis(trifluoromethyl)benzoyloxy)-3-(S)-(4-fluorophenyl)morpholine A solution of 2.67 g (10.0 mmol) of 4-benzyl-3-(S)-(4-fluorophenyl)-2-morpholinone (Description 2) in 40 ml of dry THF was cooled to −78° C. The cold solution was treated with 12.5 ml of 1.0M L-Selectride® solution in THF, maintaining the internal reaction temperature below −70° C. The resulting solution was stirred cold for 45 minutes and the reaction was charged with 3.60 ml (20.0 mmol) of 3,5-bis(trifluoromethyl)benzoyl chloride. The resulting yellow mixture was stirred cold for 30 minutes and the reaction was quenched with 50 ml of saturated aqueous sodium bicarbonate solution. The quenched mixture was partitioned between 300 ml of ether and 50 ml of water and the layers were separated. The organic layer was dried over magnesium sulfate. The aqueous layer was extracted with 300 ml of ether; the extract was dried and combined with the original organic layer. The combined organics were concentrated in vacuo. Flash chromatography on 150 g of silica gel using 37:3 v/v hexanes/ether as the eluant afforded 4.06 g (80%) of the title compound as a solid. $^1$H NMR (200 MHz, $CDCl_3$) δ 2.50 (1H, dt, J=3.4, 12.0), 2.97 (1H, app d, J=12.0), 2.99 (1H, d, J=13.6), 3.72–3.79 (1H, m), 3.82 (1H, d, J=2.6), 4.00 (1H, d, J=13.6), 4.20 (dr, J=2.4, 11.6), 6.22 (1H, d, J=2.6), 7.22–7.37 (7H, m), 7.57 (2H, app d, J=6.8), 8.07 (1H, s), 8.47 (2H, s). MS (FAB) m/z 528 (M+H, 25%), 270 (100%). Anal. Calcd for $C_{26}H_{20}F_7NO_3$: C, 59.21; H, 3.82; N, 2.66; F, 25.21. Found: C, 59.06; H, 4.05; N, 2.50; F, 25.18.

DESCRIPTION 4

4-Benzyl-2-(R)-(1-(3,5-bis(trifluoromethyl)phenyl)ethenyloxy)-3-(S)-(4-fluorophenyl)morpholine Step A: Dimethyl titanocene A solution of 2.49 g (10.0 mmol) of titanocene dichloride in 50 ml of ether in the dark at 0° C. was treated with 17.5 ml of 1.4M methyllithium solution in ether maintaining the internal temperature below 5° C. The resulting yellow/orange mixture was stirred at room temperature for 30 minutes and the reaction was quenched by slowly adding 25 g of ice. The quenched reaction mixture was diluted with 50 ml of ether and 25 ml of water and the layers were separated. The organic layer was dried over magnesium sulfate and concentrated in vacuo to afford 2.03 g (98%) of the title compound as a light-sensitive solid. The dimethyl titanocene could be stored as a solution in toluene at 0° C. for at least 2 weeks without apparent chemical degradation. $^1$H NMR (200 MHz, $CDCl_3$) δ −0.15 (6H, s), 6.06 (10H, s).

Step B: 4-Benzyl-2-(R)-(1-(3,5-bis(trifluoromethyl)phenyl)ethenyloxy)-3-(S)-(4-fluorophenyl)morpholine A solution of the compound of Description 3 (2.50 g, 4.9 mmol) and 2.50 g (12.0 mmol) of dimethyl titanocene (from Step A) in 35 ml of 1:1 v/v THF/toluene was stirred in an oil bath at 80° C. for 16 hours. The reaction mixture was cooled and concentrated in vacuo. Flash chromatography on 150 g of silica gel using 3:1 v/v hexanes/methylene chloride as the eluant afforded 1.71 g (69%) of the title compound as a solid. An analytical sample was obtained via recrystallisation from isopropanol: $^1$H NMR (400 MHz, $CDCl_3$) δ 2.42 (1H, dr, J=3.6, 12.0), 2.90 (1H, app d, J=12.0), 2.91 (1H, d, J=13.6), 3.62–3.66 (1H, m), 3.72 (1H, d, J=2.6), 3.94 (1H, d, J=13.6), 4.09 (1H, dt, J=2.4, 12.0), 4.75 (1H, d, J=3.2), 4.82 (1H, d, J=3.2), 5.32 (1H, d, J=2.6), 7.09 (2H, t, J=8.8), 7.24–7.33 (5H, m), 7.58–7.62 (2H, m), 7.80 (1H, s), 7.90 (2H, s); MS (FAB) 526 (M+H, 75%), 270 (100%). Anal. Calcd for $C_{27}H_{22}F_7NO_2$: C, 61.72; H, 4.22; N, 2.67; F, 25.31. Found: C, 61.79; H, 4.10; N, 2.65; F, 25.27%.

DESCRIPTION 5

2-(R)-(1-(R)-(3,5-Bis(trifluoromethyl)phenyl)ethoxy)-3-(S):(4-fluorophenyl)morpholine The compound of Description 4 (4.0 g) was dissolved in ethyl acetate (50 ml) and isopropanol (16 ml). To this solution was added palladium on charcoal (1.5 g) and the mixture was hydrogenated at 40 psi for 36 h. The catalyst was removed by filtration through Celite and the solvents were removed in vacuo. The residue was purified by flash chromatography on silica using 100% ethyl acetate and then 1–10% methanol in ethyl acetate. This afforded isomer A 500 mg (15%) and isomer B 2.6 g (80%) as clear oils—isomer B crystallised on standing. For the title compound: $^1$H NMR (400 MHz, $CDCl_3$) δ 1.16 (3H, d, J=6.8 MHz), 1.80 (1H, br s), 3.13 (1H, dd, J=3.2, 12.4 Hz), 3.23 (1H, dt, J=3.6, 12.4 Hz), 3.63 (1H, dd, J=2.4, 11.2 Hz), 4.01 (1H, d, J=2.4 Hz), 4.13 (1H, dt, J=3.2, 12.0 Hz), 4.42 (1H, d, J=2.4 Hz), 4.19 (1H, q, J=6.8 Hz), 7.04–7.09 (2H, m), 7.27–7.40 (4H, m), 7.73 (1H, s); MS (FAB) 438 (M+H, 75%), 180 (100%).

HCl salt formation. To a solution of the free base (0.77 g) in diethyl ether (10 ml) was added 1M-HCl in methanol (1.75 ml). The solution was evaporated to dryness and on addition of diethyt ether crystals formed. The solution was filtered and the residue washed with diethyl ether to give the title compound hydrochloride salt mp 248°–250° C. Found: C, 50.46; H, 3.85; N, 3.01; Cl, 7.31. $C_{20}H_{18}F_7NO_2$. HCl requires C, 50.70; H, 4.04; N, 2.96; Cl, 7.48%.

DESCRIPTION 6

4-Benzyl-3-(S)-(4-fluorophenyl)-2-(R)-(3-fluoro-5-(trifluoromethyl)benzoyloxy)morpholine The title compound was prepared from the reaction of the compound of Description 2 with 3-fluoro-5-(trifluoromethyl)benzoyl chloride according to the procedure illustrated in Description 3. $^1$H NMR (360 MHz, CDCl$_3$) δ 2.50 (1H, dr, J=3.3, 12.0), 2.96 (1H, d, J=12.0), 2.98 (1H, d, J=13.6), 3.75 (1H, dd, J=1.7, 11.5), 3.80 (1H, d, J=2.5), 3.92 (1H, d, J=13.6), 4.19 (1H, dt, J=2.1, 12.0), 6.20 (1H, d, J=2.5), 6.99 (2H, t, J=8.7), 7.2–7.37 (5H, m), 7.51–7.55 (3H, m), 7.89 (1H, d, J=8.4), 8.09 (1H, s). MS (Cl$^+$) m/z 478 (M$^+$+1, 100%). Anal. Calcd. for C$_{25}$H$_{20}$F$_5$NO$_3$: C, 62.88; H, 4.23; N, 2.93. Found: C, 62.59; H, 4.03; N, 3.07%.

DESCRIPTION 7

4-Benzyl-3-(S)-(4-fluorophenyl)-2-(R)-(1-(3-fluoro-5-(trifluoromethyl)phenyl)ethenyloxy)morpholine The title compound was prepared in 85% yield from the compound of Description 6 according to the procedure illustrated in Description 4. $^1$H NMR (360 MHz, CDCl$_3$) δ 2.42 (1H, dt, J=3.6, 12.0), 2.90 (1H, d, J=12.0), 2.91 (1H, d, J=13.6), 3.60–3.62 (1H, m), 3.72 (1H, d, J=2.6), 3.92 (1H, d, J=13.6), 4.09 (1H, dt, J=2.4, 12.0), 4.67 (1H, d, J=2.9), 4.76 (1H, d, J=2.9), 5.28 (1H, d, J=2.6), 7.07 (2H, t, J=8.7), 7.2–7.37 (7H, m), 7.53 (1H, s), 7.57–7.61 (2H, m). MS (Cl$^+$) 476 (M+1, 100%).

DESCRIPTION 8

3-(S)-(4-Fluorophenyl)-2-(R)-(1-(R)-(3-fluoro-5-(trifluoromethyl)phenyl)ethoxy)morpholine The compound of Description 7 was hydrogenated according to the method illustrated in Description 5. This afforded a mixture of 2 epimeric products isomer A and isomer B (the major product) as clear oils. For the title compound: $^1$H NMR (360 MHz, CDCl$_3$) δ 1.42 (3H, d, J=6.6 Hz), 1.91 (1H, s), 3.11 (1H, dd, J=3.2, 12.4 Hz), 3.22 (1H, dt, J=3.6, 12.4 Hz), 3.58–3.62 (1H, m), 4.01 (1H, d, J=2.3 Hz), 4.11 (1H, dt, J=3.2, 12.0 Hz), 4.41 (1H, d, J=2.3 Hz), 4.80 (1H, q, J=6.6 Hz), 6.41 (1H, d, J=9.2 Hz), 6.86 (1H, s), 7.02 (2H, t, J=8.7 Hz), 7.08 (2H, d, J=9.2 Hz), 7.21–7.26 (2H, m). MS (Cl$^+$) m/z 387 (M+1, 100%). Anal. Calcd. for C$_{19}$H$_{18}$F$_5$NO$_2$: C, 58.91; H, 4.69; N, 3.62. Found: C, 58.88; H, 4.81; N, 3.76%.

DESCRIPTION 9

2-(R)-(1-(R)-(3,5-Bis(trifluoromethyl)phenyl)ethoxy)-3-(S)-(4-fluorophenyl)-4-(2,3-dihydro-2-oxo-1,3-imidazol-4-yl)methylmorpholine A mixture of the compound of Description 5 (1 g), N,N-diacetyl-4-bromomethyl-2-imidazolinone (0.62 g) (prepared according to the procedure of Dolan and Dushinsky JACS 1948, 70, 657) and potassium carbonate (0.63 g) in 10 ml of dimethylformamide was stirred at room temperature for 15 min. The reaction mixture was diluted with ethyl acetate (100 ml) and was washed with water and brine. The ethyl acetate layer was dried (MgSO$_4$) and evaporated in vacuo. The resulting oil was dissolved in ethanol (10 ml), 33% ethanolic methylamine (1 ml) was added and the mixture stirred at room temperature for 10 min. The mixture was concentrated in vacuo to afford a solid. Recrystallisation from ethyl acetate/methanol afforded the title compound (0.63 g). mp 192°–194° C. $^1$H NMR (360 MHz, DMSO-d$_6$) δ 1.35 (3H, d, J=6.5 Hz), 2.25 (1H, dt, J=8.7 Hz), 2.60 (1H, d, J=13.8 Hz), 2.89 (1H, d, J=11.6 Hz), 3.28–3.36 (2H, m), 3.62 (1H, d, J=10.2 Hz), 4.1 (1H, t, J=10.0 Hz), 4.31 (1H, d, J=2.7 Hz), 4.92 (1H, q, J=6.5 Hz), 5.97 (1H, s), 7.06 (2H, t, J=8.8Hz), 7.36 (2H, s), 7.65–7.85 (2H, m), 7.84 (1H, s), 9.58 (1H, s), 9.8 (1H, s).

DESCRIPTION 10

3-(S)-(4-Fluorophenyl)-2-(R)-(1-(R)-(3-fluoro-5-(trifluoromethyl)phenyl)ethoxy)-4-(2,3-dihydro-2-oxo-1,3-imidazol-4-yl)methylmorpholine The title compound was prepared from the compound of Description 8 using a procedure analogous to that of Description 9. mp 209°–210° C. [α]$_D$=+92.8 (c=1.0, methanol). $^1$H NMR (360 MHz, DMSO-d$_6$) δ 1.31 (3H, d, J=6.5 Hz), 2.24 (1H, dt, J=3.0, 11.9 Hz), 2.6 (1H, d, J=13.9 Hz), 3.61 (1H, d, J=11.2 Hz), 4.1 (1H, t, J=11.0 Hz), 4.29 (1H, d, J=2.3 Hz), 4.8 (1H, q, J=6.5 Hz), 6.00 (1H, s), 6.55 (1H, d, J=9.3 Hz), 6.94 (1H, s), 7.11 (2H, t, J=8.7 Hz), 7.39 (1H, d, J=8.4 Hz), 7.51 (2H, s), 9.59 (1H, s), 9.84 (1H, s).

DESCRIPTION 11

2-(R)-(1-(R)-(3,5-Bis(trifluoromethyl)phenyl)ethoxy)-3-(S)-(4-fluorophenyl)-4-(1,2,4-triazol-3-yl)methylmorpholine A solution of the compound of Description 5 (3.77 g) and potassium carbonate (3.59 g) in dry dimethylformamide (7 ml) was stirred at room temperature for 10 min. N-Formyl-2-chloroacetamidrazone (prepared according to I. Yanagisawa, J. Med Chem. (1984), 27, 849) was added and the reaction mixture was heated at 60° C. for 1 hour. The temperature was then increased to 140° C. for 2 h. The mixture was cooled and partitioned between ethyl acetate and water and the organic phase was washed with water, brine, dried (MgSO$_4$) and evaporated to give a brown oil. The residue was purified by chromatography on silica using 1–5% methanol in dichloromethane. This afforded the product as a white foam (2.99 g). $^1$H NMR (360 MHz, DMSO) δ 8.25 (1H, s), 7.85 (1H, s), 7.50 (2H, t), 7.37 (2H, s), 7.11 (2H, t, J=9.0 Hz), 4.93 (1H, q, J=6.6 Hz), 4.32 (1H, d, J=2.8 Hz), 4.09 (1H, dt, J=11.5 Hz), 3.63 (1H, d, J=14.1 Hz), 3.59 (1H, d, J=3.0 Hz), 3.17 (1H, d, J=14.0 Hz), 2.49 (1H, dt, J=15.7 Hz), 1.36 (3H, d, J=6.6 Hz). MS (Cl$^+$) m/z 519. Anal. Calcd. for C$_{23}$H$_{19}$F$_7$N$_4$O$_2$: C, 53.29; H, 4.08; N, 10.81; Found: C, 52.92; H, 3.94; N, 10.33.

DESCRIPTION 12

4-Benzyl-3-(S)-(4-fluorophenyl)-2-(R)-(3-(trifluoromethyl)benzoyloxy)morpholine The title compound was prepared from the reaction of the compound of Description 2 with 3-(trifluoromethyl)benzoyl chloride according to the procedure illustrated in Description 3. $^1$H NMR (360 MHz, CDCl$_3$) δ 2.48 (1H, dt, J=12.0, 3.5), 2.94 (1H, d, J=13.6), 3.73 (1H, app.d, J=11.4), 3.78 (1H, d, J=2.7), 3.91 (1H, d, J=13.6), 4.21 (1H, dt, J=11.7, 2.4), 6.20 (1H, d, J=2.8), 6.97 (2H, t, J=8.7), 7.25–7.37 (5H, m), 7.53 (2H, m), 7.61 (1H, t, J=7.8), 7.84 (1H, d, J=8.0), 8.21 (1H, d, J=7.8), 8.30 (1H, s). MS (Cl$^+$) m/z 460 (M+1, 100%).

DESCRIPTION 13

4-Benzyl-3-(S)-(4-fluorophenyl)-2-(R)-(1-(3-(trifluoromethyl)phenyl)ethenyloxy)morpholine The title compound was prepared from the compound of Description 12 according to the procedure illustrated in Description 4. $^1$H NMR (360 MHz, CDCl$_3$) δ 2.40 (1H, dt, J=11.9, 3.6 Hz), 2.87 (1H, app. d, J=11.8 Hz), 2.89 (1H, d, J=13.5 Hz), 3.62 (1H, app.d, J=11.5 Hz), 3.70 (1H, d, J=2.7 Hz), 3.91 (1H, d, J=13.5 Hz), 4.12 (1H, dt, J=11.7, 2.4 Hz), 4.62 (1H, d, J=2.7 Hz), 4.74 (1H, d, J=2.7 Hz), 5.30 (1H, d, J=2.7 Hz), 7.07 (2H, t, J=8.7 Hz), 7.21–7.32 (5H, m), 7.40 (1H, t, J=7.8 Hz), 7.53–7.63 (4H, m), 7.74 (1H, s). MS (Cl$^+$) m/z 458 (M+1, 100%).

DESCRIPTION 14

3-(S)-(4-Fluorophenyl)-2-(R)-(1-(R)-(3-(trifluoromethyl)phenyl)ethoxy)morpholine The compound of Description 13 was hydrogenated according to the method illustrated in Description 5. This afforded a mixture of 2 epimeric products isomer A and isomer B in approximately equal mass as yellow oils. The title compound (isomer B): $^1$H NMR (360 MHz, CDCl$_3$) δ 1.43 (3H, d, J=6.6), 3.11 (1H, dd, J=12.6, 2.9), 3.22 (1H, dt, J=12.4, 3.7), 3.60 (1H, dd, J=11.1, 2.8), 3.99 (1H, d, J=2.2), 4.13 (1H, dt, J=11.6, 3.2), 4.42 (1H, d, J=2.2), 4.81 (1H, q, J=6.6), 6.84 (1H, d, J=7.8), 6.96–7.03 (3H, m), 7.16–7.27 (3H, m), 7.38 (1H, d, J=7.5). MS (Cl$^+$) m/z 370 (M+1, 100%). Anal. Calcd. for C$_{19}$H$_{19}$F$_4$NO$_2$: C, 61.77; H, 5.20; N, 3.79. Found: C, 61.60; H, 5.16; N, 3.95%.

DESCRIPTION 15

4-Benzyl-3-(S)-phenyl-2-morpholinone

Step A: N-Benzyl-(S)-phenylglycine

A solution of 1.51 g (10.0 mmol) of (S)-phenylglycine in 5 ml of 2N aqueous sodium hydroxide solution was treated with 1.0 ml (10.0 mmol) of benzaldehyde and stirred at room temperature for 20 minutes. The solution was diluted with 5 ml of methanol, cooled to 0° C., and carefully treated with 200 mg (5.3 mmol) of sodium borohydride. The cooling bath was removed and the reaction mixture was stirred at room temperature for 1.5 hours. The reaction was diluted with 20 ml of water and extracted with 2×25 ml of methylene chloride. The aqueous layer was acidified with concentrated hydrochloric acid to pH 6 and the solid that precipitated was filtered, washed with 50 ml of water, 50 ml of 1:1 v/v methanol/ethyl ether and 50 ml of ether, and dried to afford 1.83 g (76%) of product, mp 230°–232° C. Anal. Calcd for C$_{15}$H$_{15}$NO$_2$: C, 74.66; H, 6.27; N, 5.81. Found: C, 74.17; H, 6.19; N, 5.86.

Step B: 4-Benzyl-3-(S)-phenyl-2-morpholinone

A mixture of 4.00 g (16.6 mmol) of N-benzyl-(S)-phenylglycine (from Step A) 5.00 g (36.0 mmol) of potassium carbonate, 10.0 ml of 1,2-dibromoethane and 25 ml of N,N-dimethylformamide was stirred at 100° C. for 20 hours. The mixture was cooled and partitioned between 200 ml of ethyl ether and 100 ml of water. The layers were separated and the organic layer was washed with 3×50 ml of water, dried over magnesium sulfate and concentrated in vacuo. The residue was purified by flash chromatography on 125 g of silica gel eluting with 9:1 v/v, then 4:1 hexanes/ethyl ether to afford 2.41 g (54%) of the product as a solid, mp 98°–100° C. $^1$H NMR (250 MHz, CDCl$_3$) δ 2.54–2.68 (1H, m), 2.96 (1H, dt, J=12.8, 2.8), 3.14 (1H, d, J=13.3), 3.75 (1H, d, J=13.3), 4.23 (1H, s), 4.29–4.37 (1H, m), 4.53 (dt, J=3.2, 11.0), 7.20–7.56 (10H, m). MS (FAB): m/z 268 (M+H; 100%). Anal. Calcd for C$_{17}$H$_{17}$NO$_2$: C, 76.38; H, 6.41; N, 5.24. Found: C, 76.06; H, 6.40; N, 5.78.

DESCRIPTION 16

4-Benzyl-2-(R)-(3,5-bis(trifluoromethyl)benzoyloxy)-3-(S)phenylmorpholine

A solution of 2.67 g (10.0 mmol) of the compound of Description 15 in 40 ml of dry THF was cooled to –78° C. The cold solution was treated with 12.5 ml of 1.0M L-Selectride® solution in THF, maintaining the internal reaction temperature below –70° C. The resulting solution was stirred cold for 45 minutes and the reaction was charged with 3.60 ml (20.0 mmol) of 3,5-bis( trifluoromethyl) benzoyl chloride. The resulting yellow mixture was stirred cold for 30 minutes and the reaction was quenched with 50 ml of saturated aqueous sodium bicarbonate solution. The quenched mixture was partitioned between 300 ml of ether and 50 ml of water and the layers were separated. The organic layer was dried over magnesium sulfate. The aqueous layer was extracted with 300 ml of ether; the extract was dried and combined with the original organic layer. The combined organics were concentrated in vacuo. Flash chromatography on 150 g of silica gel using 37:3 v/v hexanes/ether as the eluant afforded 4.06 g (80%) of the title compound as a solid. $^1$H NMR (200 MHz ppm, CDCl$_3$) δ 2.50 (1H, dt, J=3.4, 12.0), 2.97 (1H, app d, J=12.0), 2.99 (1H, d, J=13.6), 3.72–3.79 (1H, m), 3.82 (1H, d, J=2.6), 4.00 (1H, d, J=13.6), 4.20 (dt, J=2.4, 11.6), 6.22 (1H, d, J=2.6), 7.22–7.37 (7H, m), 7.57 (2H, app d, J=6.8), 8.07 (1H, s), 8.47 (2H, s). Anal. Calcd for C$_{26}$H$_{21}$F$_6$NO$_3$: C, 61.29; H. 4.16; N, 2.75; F, 22.38. Found: C, 61.18; H, 4.14; N, 2.70: F, 22.13.

DESCRIPTION 17

4-Benzyl-2-(R)-(1-(3,5-bis(trifluoromethyl)phenyl)ethenyloxy)-3-(S)-phenylmorpholine A solution of 2.50 g (4.9 mmol) of the compound of Description 16 and 2.50 g (12.0 mmol) of dimethyl titanocene (Description 4a), in 35 ml of 1:1 v/v THF/toluene was stirred in an oil bath at 80° C. for 16 hours. The reaction mixture was cooled and concentrated in vacuo. Flash chromatography on 150 g of silica gel using 3:1 v/v hexanes/methylene chloride as the eluant afforded 1.71 g (69%) of the title compound as a solid. $^1$H NMR (400 MHz, CDCl$_3$) δ 2.42 (1H, dt, J=3.6, 12.0), 2.89 (app d, J=11.6), 2.92 (1H, d, J=13.6), 3.61–3.66 (1H, m), 3.73 (1H, d, J=2.8), 4.00 (1H, d, J=13.6), 4.09 (1H, dt, J=2.4, 11.6), 4.75 (1H, d, J=2.8), 4.79 (1H, d, J=2.8), 5.36 (1H, d, J=2.4), 7.23–7.41 (7H, m), 7.63 (1H, app d, J=7.2), 7.79 (1H, s), 7.91 (2H, s). MS (FAB) m/z 508 (M+1, 25%). Anal. Calcd. for C$_{27}$H$_{23}$F$_6$NO$_2$: C, 63.90; H, 4.57; N, 2.76; F, 22.46. Found: C, 63.71; H, 4.53; N, 2.68; F, 22.66.

DESCRIPTION 18

2-(R)-(1-(S)-3,5-Bis(trifluoromethyl)phenyl) ethoxy)-3-(S)-phenylmorpholine

A mixture of the compound of Description 17 (1.5 g) and 10% palladium on carbon catalyst (750 mg) in a mixture of isopropanol/ethyl acetate (25 ml, 3:2 v/v) was stirred under an atmosphere of hydrogen for 48 h. The catalyst was removed by filtration through celite and the reaction flask and filter pad were rinsed with ethyl acetate (500 ml). The flitrate was concentrated in vacuo, flash chromatography afforded epimer A (106 mg) and epimer B (899 mg) as clear oils. The title compound, epimer B had the following analysis: $^1$H NMR (CDCl$_3$, 400 MHz) δ 1.46 (3H, d, J=6.8 Hz), 1.92 (1H, brs), 3.13 (1H, dd, J=3.0, 12.6 Hz), 3.24 (1H, dt, J=3.6, 12.6 Hz), 3.62 (1H, dd, J=3.6, 11.2 Hz), 4.04 (1H, d, J=2.4 Hz), 4.14 (1H, dt, J=3.0, 11.2 Hz), 4.48 (1H, d, J=2.4 Hz), 4.90 (1H, q, J=6.8 Hz), 7.21–7.32 (7H, m), 7.64 (1H, s). MS (Cl$^+$) m/z 420 (M$^+$+1, 20%), 178 (100%). Anal. Calcd. for C$_{20}$H$_{19}$F$_6$NO$_2$: C, 57.28; H, 4.57; N, 3.34; F, 27.18. Found: C, 57.41; H, 4.61; N, 3.29; F, 27.23.

DESCRIPTION 19

2-(R)-(1-(R)-(3,5-Bis(trifluoromethyl)phenyl) ethoxy)-3-(S)-phenyl-4-(1,2,4-triazol-3-yl)methyl- morpholine This compound was prepared from the compound of Description 18 following the procedure illustrated in Description 11. MS (Cl$^+$) m/z 501 (M$^+$+1, 100%).

DESCRIPTION 20

4-Benzyl-2-(R)-(1-(S)-(3,5-bis(trifluoromethyl)phe- nyl)-2-hydroxyethoxy)-3-(S)-(4-fluorophenyl)mor- pholine The compound of Description 4 (12.8 g) was dissolved in tetrahydrofuran (50 ml) and the mixture was cooled in ice. Borane (49 ml of 1.0M in tetrahydrofuran) was added dropwise and the reaction mixture was stirred at room temperature for 3 hr. The solution was cooled in ice and sodium hydroxide (120 ml, 1M) and hydrogen peroxide (36 ml, 30 wt. %) were added dropwise cautiously. The resulting mixture was stirred for 1 h, then diluted with water (200 ml) and extracted with ethyl acetate (3×50 ml). The organic extracts were washed with sodium sulfite and then brine.

The organic phase was dried (MgSO$_4$) and evaporated to give a clear oil. Tlc (50:50 ethyl acetate/hexane) indicated two main products which were separated by flash chromatography on silica using a gradient elution of 1–30% ethyl acetate in hexane. The minor product eluted first (2.3 g) and the major product eluted last (8 g). The major product was isolated as a white foam. $^1$H NMR (360 MHz, DMSO-d$_6$) δ 2.23–2.29 (1H, m), 2.73 (1H, d), 2.80 (1H, d, J=13.0 Hz), 3.48 (1H, d, J=3.5 Hz), 3.45–3.52 (2H, m), 3.56–3.65 (2H, m), 4.00–4.06 (1H, m), 4.37 (1H, d, J=3.0 Hz), 4.81 (1H, t, J=6.0 Hz), 4.92 (1H, t, J=5.5 Hz), 7.14 (2H, t, J=9.0 Hz), 7.23–7.33 (5H, m), 7.35 (2H, s, ArH), 7.57 (2H, t, ArH), 7.85 (1H, s, ArH). MS (Cl$^+$) m/z 544 (M$^+$+1, 100%).

DESCRIPTION 21

2-(R)-(1-(S)-(3,5-bis(trifluoromethyl)phenyl)-2-hy- droxyethoxy)-3-(S)-(4-fluorophenyl)morpholine The compound of Description 20 (8 g) was dissolved in ethyl acetate (100 ml) and isopropanol (50 ml) and palladium on charcoal (1.5 g) was added to the solution. This mixture was hydrogenated at 40 psi overnight. The catalyst was removed by filtration and the solvents were removed in vacuo. The residue was purified by flash silica chromatography using 1–10% methanol in dichloromethane as eluant. This afforded the product as a white powder (5.7 g, 90%). $^1$H NMR (360 MHz, CDCl$_3$) δ 2.68–2.73 (1H, m), 3.03–3.15 (1H, m), 3.43–3.65 (3H, m), 3.95 (1H, d, J=3.0 Hz), 4.12–4.22 (1H, m), 4.40 (1H, d, J=3.0 Hz), 4.89 (1H, t, J=7.0 Hz), 6.99 (t, J=9.0 Hz, ArH), 7.15 (2H, s, ArH), 7.26–7.31 (1H, m, ArH), 7.62 (1H, s, ArH). MS (Cl$^+$) m/z 454 (M$^+$+1, 100%).

DESCRIPTION 22

3-(S)-(4-Fluorophenyl)-2-(R)-(1-(S)-(3-fluoro-5- (trifluoromethyl)phenyl)-2-hydroxyethoxy)morpho- line Step A: 4-Benzyl-3-(S)-(4-fluorophenyl)-2-(R)-(1-(S)-(3- fluoro-5-(trifluoromethyl)phenyl)-2-hydroxyethoxy)-mor- pholine The compound of Description 7 (0.8 g) was dissolved in tetrahydrofuran (5 ml) at room temperature and borane (5 ml, 1.0M in tetrahydrofuran) was added. The solution was stirred under nitrogen for 30 min until all starting material had reacted. Hydrogen peroxide (5 ml, 29% aq.) and sodium hydroxide (10 ml, 4N) were added dropwise to the cooled (0° C.) solution with much effervescence. The resulting mixture was extracted with ethyl acetate, the organic phase was washed with sodium bisulfite and brine, dried (MgSO$_4$) and evaporated to afford a colourless oil (1 g). This material was not purified further but reacted as described in the following step.

Step B: 3-(S)-(4-Fluorophenyl)-2-(R)-(1-(S) -(3-fluoro-5- (trifluoromethyl)phenyl)-2-hydroxyethoxy) morpholine The compound of (a) above (1 g) was dissolved in ethyl acetate/2-propanol (20 ml, 3:1) and treated with Pd on carbon (100 mg). The mixture was hydrogenareal at 60 psi for 12 h. The catalyst was removed by filtration and the solvent was removed in vacuo. The residue was purified by medium pressure chromatography on silica (Lobar) using 5% methanol in dichloromethane as eluant. The product was recrystallised from ether. $^1$H NMR (360 MHz, DMSO-d$_6$) δ 2.77–3.04 (3H, m), 3.36–3.51 (2H, m), 3.93 (1H, br s), 4.05–4.13 (1H, m), 4.36 (1H, d, J=2.0 Hz), 4.72 (1H, t, J=5.0 Hz), 4.98 (1H, t, J=7.0 Hz), 6.66 (1H, d, J=9.2 Hz), 6.89 (1H, s), 7.10 (2H, t, J=9.0 Hz), 7.33–7.37 (2H, m), 7.41 (1H, d, J=9.0 Hz); MS (Cl$^+$) m/z 404 (M$^+$+1, 100).

DESCRIPTION 23

N-Carbomethoxy-2-chloroacetamidrazone (ClCH$_2$C(=NH)NHNHCOOCH$_3$)

Sodium methoxide (20 ml, 1M) was added to a solution of chloroacetonitrile (54.1 g)in anhydrous methanol (100 ml) at 0° C. The mixture was stirred at room temperature for 30 min and then neutralised with acetic acid (1.2 ml). Methyl hydrazinocarboxylate (64.5 g, predistilled in vacuo) was dissolved in warm dimethylformamide (35 ml) and methanol (300 ml) and was added to the reaction mixture at 0° C. The mixture was stirred for 30 min and the crystalline solid which had formed was removed by filtration and washed with ethyl acetate to give the title compound: mp 138°–140° C.

DESCRIPTION 24

2-(R)-(1-(S)-(3,5-Bis(trifluoromethyl)phenyl)-2- hydroxyethoxy)-3-(S)-phenylmorpholine Step A: 4-Benzyl-2-(R)-(1-(S)-(3,5-Bis( trifluorometh- yl)phenyl)-2-hydroxyethoxy)-3-(S) -phenylmorpholine The compound of Description 17 was reacted with diborane and subsequently with basic hydrogen peroxide according to the method illustrated in Description 20. This intermediate was not purified and was reacted crude in the following step.

Step B: 2-(R)-(1-(S)-(3,5-Bis(trifluoromethyl) phenyl-2-hydroxyethoxy)-3-(S)-phenylmorpholine The compound of (a) above was aleprotected by hydrogenolysis as described in Description 21 to afford the title compound as a white solid. $^1$H NMR (360 MHz, CDCl$_3$) δ 2.85 (1H, app d, J=11.0 Hz), 3.15 (1H, dr, J=12.0, 3.5 Hz), 3.58 (1H, dd, J=11.0, 3.0 Hz), 3.63–3.71 (2H, m), 4.02 (1H, d, J=3.0 Hz), 4.25 (dr, J=12.0, 3.0 Hz), 4.53 (1H, d, J=3.0 Hz), 4.93 (1H, t, J=5.0 Hz), 7.22 (2H, s), 7.35 (5H, br s), 7.67 (1H, s). MS (Cl$^+$) m/z 436 (M+1, 100%).

DESCRIPTION 25

4-Benzyl-2-(R)-(3-fluoro-5-(trifluoromethyl)benzoyloxy)-3-(S)-phenylmorpholine The compound of Description 15 was reacted with L-Selectride followed by 3-fluoro-5-(trifluoromethyl)benzoyl chloride according to the method illustrated in Description 3 to afford the title compound as a clear oil. $^1$H NMR (250 MHz, CDCl$_3$) δ 2.47 (1H, dt, J=8.5, 2.5 Hz), 2.93–2.97 (2H, m), 3.72–3.76 (1H, m), 3.79 (1H, d, J=3.0 Hz), 3.97 (1H, d, J=9.5 Hz), 4.17 (1H, dt, J=8.5, 2.5 Hz), 6.22 (1H, d, J=3.0 Hz), 7.19–7.35 (8H, m), 7.45–7.56 (3H, m), 7.88 (1H, brd), 8.09 (1H, s). MS (Cl$^+$) m/z 460 (M+1, 100%).

DESCRIPTION 26

4-Benzyl-2-(R)-(3-fluoro-5-(trifluoromethyl)phenyl)ethenyloxy)-3-(S)-phenylmorpholine The compound of Description 25 was reacted with dimethyl titanocene according to the procedure illustrated in Description 4. This afforded the title compound as a clear oil (66%). $^1$H NMR (250 MHz, CDCl$_3$) δ 2.29–2.39 (1H, m), 2.79–2.86 (2H, m), 3.53–3.64 (2H, m), 3.92 (1H, d, J=13.5 Hz), 4.00–4.09 (1H, m), 4.61 (1H, d, J=3.0 Hz), 4.66 (1H, d, J=3.0 Hz), 5.25 (1H, d, J=3.0 Hz), 7.14–7.35 (10H, m), 7.47 (1H, s), 7.56 (2H, brd). MS (Cl$^+$) m/z 458 (M+1, 100%).

DESCRIPTION 27

2-(R)-(1-(S)-(3-fluoro-5-(trifluoromethyl)phenyl)-2-hydroxyethoxy)-3-(S)-phenylmorpholine Step A: 4-Benzyl-2-(R)-(1-(S)-(3-fluoro-5-(trifluoromethyl)phenyl)-2-hydroxyethoxy)-3-(S)-phenylmorpholine The compound of Description 26 was reacted with diborane followed by treatment with basic hydrogen peroxide according to the procedure illustrated in Description 20 to afford a clear oil. MS (Cl$^+$) m/z 476 (M+1, 100%).

Step B: 2-(R)-(1-(S)-(3-fluoro-5-( trifluoromethyl)phenyl)-2-hydroxyethoxy)-3-(S)-phenylmorpholine The compound of (a) above was deprotected following the method illustrated in Description 21. This afforded the title compound as a white solid. Anal. Calcd. for C$_{19}$H$_{19}$F$_4$NO$_3$: C, 59.22; H, 4.97; N, 3.63. Found: C, 59.18; H, 5.12; N, 3.62%. MS (Cl$^+$) m/z 386 (M+1, 100%).

DESCRIPTION 28

4-Benzyl-3-(S)-phenyl-2-(R)-(3-( trifluoromethyl)-benzoyloxy)morpholine

Prepared from the compound of Description 15 following the method illustrated in Description 3. $^1$H NMR (250 MHz, CDCl$_3$) δ 2.47 (1H, dt), 2.89–2.99 (2H, m), 3.69–3.82 (2H, m), 3.98 (1H, d), 4.23 (1H, dt), 6.22 (1H, d), 7.22–7.40 (8H, m), 7.54–7.66 (3H, m), 7.83 (1H, d), 8.22 (1H, d), 8.31 (1H, s).

DESCRIPTION 29

4-Benzyl-3-(S)-phenyl-2-(R)-(1-(3-trifluoromethyl)phenyl)ethenyloxy)morpholine Prepared from the compound of Description 28 following the method illustrated in Description 4. $^1$H NMR (250 MHz, CDCl$_3$) δ 2.41 (1H, dr), 2.84–2.96 (2H, m), 3.58–3.66 (1H, m), 3.72 (1H, d, 3.99 (1H, d), 4.13 (1H, dt), 4.63 (1H, d), 4.72 (1H, d), 5.34 (1H, d), 7.21–7.43 (9H, m), 7.50–7.68 (4H, m), 7.75 (1H, s).

DESCRIPTION 30

3-(S)-Phenyl-2-(R)-(1-(S)-(3-(trifluoromethyl)phenyl)-2-hydroxyethoxy)morpholine Step A: 4-Benzyl-3-(S)-phenyl-2-(R)-(1-(S) -(3-(trifluoromethyl)phenyl)-2-hydroxyethoxy)morpholine Prepared from the compound of Description 29 following the method illustrated in Description 20.

Step B: 3-(S)-Phenyl-2-(R)-(1-(S)-3-( trifluoromethyl)phenyl)-2-hydroxyethoxy)morpholine This was carried through without purification to the title compound following the method illustrated in Description 21. $^1$H NMR (250 MHz, CDCl$_3$) δ 2.81–2.90 (1H, br d), 3.16 (1H, dt), 3.54–3.68 (3H, m), 4.02 (1H, d), 4.28 (1H, dt), 4.53 (1H, d), 4.85–4.92 (1H, m), 6.85 (1H, d), 6.99 (1H, s), 7.15–7.24 (1H, m), 7.34–7.45 (6H, m).

EXAMPLE 1

2-(R)-(1-(R)-(3,5-Bis(trifluoromethyl)phenyl) ethoxy)-4-(2,3-dihydro-5-(N,N-dimethylaminomethyl)-2-oxo-1,3-imidazol-4-yl)methyl-3-(S)-(4-fluorophenyl)morpholine The compound of Description 9 (0.35 g) was treated with N,N-dimethylmethyleneammonium iodide (0.48 g) and triethylamine (111 μl) in tetrahydrofuran (10 ml) and the mixture was heated at reflux for 4 h. The solvent was removed in vacuo and the residue was purified by chromatography on silica using 1–10% methanol in dichloromethane as eluant to afford the title compound (0.2 g). $^1$H NMR (250 MHz, CDCl$_3$) δ 9.72 (1H, s), 9.68 (1H, s), 7.86 (1H, s), 7.50–7.60 (2H, m), 7.36 (2H, s), 7.07 (2H, t, J=8.8 Hz), 4.96–4.89 (1H, q, J=6.5 Hz), 4.31 (1H, d, J=2.7 Hz), 4.08 (1H, t, J=10.1 Hz), 3.62 (1H, d, J=10.1 Hz), 3.34 (2H, s), 3.24 (1H, d, J=13.6 Hz), 3.00 (1H, d, J=13.4 Hz), 2.85 (1H, d, J=11.1 Hz), 2.62 (1H, d, J=13.6 Hz), 2.25 (1H, t, J=11 Hz), 2.01 (6H, s), and 1.35 (3H, d, J=6.5 Hz). MS (Cl$^+$) m/z 591 (M+1).

EXAMPLE 2

4-(2,3-Dihydro-5-(N,N-dimethylaminomethyl)-2-oxo-1,3-imidazol-4-yl)methyl-3-(S)-(4-fluorophenyl)-2-(R)-(1-(R)-(3-fluoro-5-(trifluoromethyl)phenyl)ethoxy)morpholine Prepared from the compound of Description 10 by a procedure analogous to that of Example 1. $^1$H NMR (250 MHz, CDCl$_3$) δ 1.38 (3H, d, J=6.2 Hz), 2.22 (6H, s), 2.78 (1H, d, J=14 Hz), 2.92 (1H, d, J=11.2 Hz), 3.14 (2H, app. q, J=14 Hz), 3.34 (1H, d, J=2.8 Hz), 3.46 (1H, d, J=11.2 Hz), 3.60 (1H, d, J=10 Hz), 4.22 (2H, m), 4.26 (1H, d, J=2.8 Hz), 4.74 (1H, q, J=6.2 Hz), 6.32 (1H, d, J=8.4 Hz), 6.72 (1H, s), 7.06 (3H, t, J=8.4 Hz), 7.36 (2H, br s), 8.70 (1H, br s), 9.20 (1H, br s).

EXAMPLE 3

3-(S)-(4-Fluorophenyl)-2-(R)-(1-(R)-(3-fluoro-5-(trifluoromethyl)phenyl)ethoxy)-4-(2,3-dihydro-2-oxo-5-pyrrolidinomethyl-1,3-imidazol-4-yl)methyl-morpholine A mixture of the compound of Description 10, (0.1 g), paraformaldehyde (0.012 g) and pyrrolidine (0.04 ml) in methanol (2 ml) was heated at 90° C. for 1 h. An additional aliquot of paraformaldehyde (12 mg) was added to the mixture and heating was continued for a further 30 min. The mixture was cooled and the solvent was removed in vacuo. The residue was purified by chromatography on silica using 0.5% aqueous ammonia and 5% methanol in dichloromethane. This afforded the product as a foam. The product was further purified as the hydrochloride salt: mp 157°–9° C. $^1$H NMR (250 MHz, (free base) CDCl$_3$) δ 1.40 (3H, t, J=6.2 Hz), 1.72 (4H, br s), 2.41 (4H, br s), 2.76 (1H, d, J=12.9 Hz), 2.92 (1H, d, J=11.2 Hz), 3.14–3.50 (5H, m), 3.62 (1H, d, J=11.2 Hz), 4.16 (1H, d, J=12.9 Hz), 4.26 (1H, d, J=2.8 Hz), 4.71 (1H, q, J=6.2 Hz), 6.30 (1H, d, J=8.4 Hz), 6.75 (1H, s), 7.06 (3H, t, J=8.4 Hz), 7.34 (2H, br s), 8.86 (1H, br s), 9.14 (1H, br s). MS (Cl$^+$) m/z 567 (M$^+$+H).

EXAMPLE 4

2-(R)-(1-(R)-(3,5-Bis(trifluoromethyl)phenyl)ethoxy)-3-(S)-(4-fluorophenyl)-4-(2,3-dihydro-2-oxo-5-pyrrolidinomethyl-1,3-imidazol-4-yl) methylmorpholine A solution of the compound of Description 5 (1.5 g) in anhydrous dimethylformamide (15 ml) was added dropwise during 5 min to a stirred solution of 4,5-bis(bromomethyl)-1,3-diacetyl-2-imidazolinone (1.8 g) (prepared by the method of Dolan and Dushinsky JACS (1948) 70, 657) in dimethylformamide (10 ml) containing potassium carbonate (1.4 g) with ice-cooling. The reaction mixture was stirred for 10 min and pyrrolidine (1.1 g) was added in one portion and stirring was continued for 20 min. The reaction mixture was diluted with water (250 ml) and extracted with ethyl acetate (3×50 ml). The combined organic extracts were washed with water (2×50 ml) and brine (1×50 ml) and then dried (K$_2$CO$_3$) and concentrated in vacuo. The residue was purified by chromatography on silica using a gradient elution of dichloromethane (100%) to dichloromethane/methanol/aqueous ammonia mixtures (85:15:0.5) to provide the title compound as a foam. $^1$H NMR (360 MHz, DMSO-d$_6$) δ 9.63 (2H, br s), 7.84 (1H, s), 7.53 (2H, br t), 7.36 (2H, s), 7.06 (2H, t, J=8.7 Hz), 4.94–4.90 (1H, q, J=6.5 Hz), 4.31 (1H, d, J=2.68 Hz), 4.07 (1H, t, J=11.4 Hz), 3.61 (1H, d, J=11.20 Hz), 3.34 (1H, J=2.7 Hz), 3.27 (1H, d, J=13.7 Hz), 3.17 (1H, d, J=13.4 Hz), 3.00 (1H, d, J=13.4 Hz), 2.86 (1H, d, J=11.6 Hz), 2.62 (1H, d, J=13.6 Hz), 2.40–2.20 (5H, m), 1.64–1.58 (2H, m), 1.35 (3H, d, J=6.5 Hz). MS (Cl$^+$) m/z 615 (M$^+$+H).

Examples 5 to 11 in Table 1 were prepared in a similar manner to that described in Example 4 from the appropriate morpholine, 4,5-bis(bromomethyl)-1,3-diacetyl-2-imidazolinone and the appropriate amine.

EXAMPLE 12

2-(R)-(1-(R)-(3,5-Bis(trifluoromethyl)phenyl)ethoxy-4-(5-(dimethylaminomethyl)-1,2,3-triazol-4-yl)methyl-3-(S)-(4-fluorophenyl)morpholine Method A a) 2-(R)-(1-(R)-(3,5-Bis(trifluoromethyl)phenyl) ethoxy-3-(S)-(4-fluorophenyl)-4-propargylmorpholine Propargyl bromide (1.9 ml) was added to a stirred mixture of the compound of Description 5 (5 g) and potassium carbonate (4.76 g) in dry dimethylformamide at 23° C. After 15 min the reaction mixture was diluted with water (250 ml) and extracted with ethyl acetate (3×100 ml). The combined organic phases were washed with brine (1×100 ml) then dried (K$_2$CO$_3$) and concentrated to leave an oil. This was purified by chromatography on silica using ethyl acetate in hexane (1:9 then 1:4) as eluent to afford the title compound as an oil. $^1$H NMR (250 MHz, CDCl$_3$) δ 1.50 (3H, d, J=6.6 Hz), 2.21 (1H, s), 2.84 (1H, d, J=11.1 Hz), 2.97 (1H, td, J=3.2, 11.7 Hz), 3.26 (2H, d, J=1.8 Hz), 3.62 (1H, d, J=2.2 Hz), 3.71 (1H, dd, J=2.3, 11.1 Hz), 4.33 (2H, m), 4.89 (1H, q, J=6.6 Hz), 7.03 (2H, t, J=8.6 Hz), 7.18 (2H, s), 7.38 (2H, br s), 7.63 (1H, s). MS (Cl$^+$) m/z 476 (MH, 100%).

b) 2-(R)-(1-(R)-(3,5-Bis(trifluoromethyl)phenyl) ethoxy)-4-(4-dimethylamino-4-oxo-but-2-ynyl)-3-(S)-(4-fluorophenyl)morpholine A mixture of N,N-dimethylcarbamoyl chloride (0.195 ml), cuprous iodide (2 mg), bis(triphenylphosphine)palladium (II) chloride (2 mg), triphenylphosphine (3 mg) and the compound described in (a) above (1 g) in triethylamine (4 ml) was heated at 90° C. for 5 h in an inert atmosphere. The mixture was cooled to 23° C. and methanol (1 ml) was added and the solvent was removed in vacuo. The residue was partitioned between water and ethyl acetate and the layers were separated. The aqueous phase was extracted with ethyl acetate (2×20 ml). The combined organic phases were washed with water, brine, dried (MgSO$_4$) and concentrated to leave an oil. The residue was purified by chromatography on silica using ethyl acetate in hexane (1:1) then ethyl acetate as eluant to provide the title compound as an oil. $^1$H NMR (250 MHz, CDCl$_3$) δ 1.49 (3H, d, J=6.6 Hz), 2.84–3.06 (2H, m), 3.00 (3H, s), 3.17 (3H, s), 3.44 (2H, s), 3.64 (1H, br s), 3.73 (1H, dd, J=2.0, 11.1 Hz), 4.33 (2H, m), 4.88 (1H, q, J=6.6 Hz), 7.03 (2H, t, J=8.7 Hz), 7.17 (2H, s), 7.38 (2H, br s), 7.63 (1H, s). MS (Cl$^+$) m/z 547 (MH, 100%).

c) 2-(R)-(1-(R)-(3,5-Bis(trifluoromethyl)phenyl) ethoxy)-4-(5-N,N-dimethylcarboxamido-1,2,3-triazol-4-yl)methyl-3-(S)-(4-fluorophenyl)morpholine A mixture of the compound described in (b) above (1.1 g) and sodium azide (0.65 g) in dimethylsulphoxide (7.5 ml) was heated at 70° C. for 17 h. The mixture was cooled to 23° C. and excess dimethylsulphoxide was removed by distillation in vacuo. The residue was partitioned between brine and ethyl acetate. The layers were separated and the organic layer was washed with brine (2×20 ml) then dried (MgSO$_4$) and concentrated to leave an oil. This was purified by chromatography on silica using ethyl acetate in hexane (1:2 then 1:1) and then ethyl acetate as eluent to provide the title compound as a pale yellow foam. $^1$H NMR (360 MHz, CDCl$_3$) δ 1.47 (3H, d, J=6.6 Hz), 2.64 (1H, m), 2.90 (1H, d, J=11.6 Hz), 3.09 (3H, s), 3.34 (3H, s), 3.65 (3H, m), 3.92 (1H, d, J=15.5 Hz), 4.27 (1H, td, J=2.1, 9.5 Hz), 4.35 (1H, d, J=2.6 Hz), 4.89 (1H, q, J=6.6 Hz), 7.01 (2H, t, J=8.7 Hz), 7.16 (2H, s), 7.39 (2H, br s), 7.64 (1H, s). m/z 590 (MH, 100%).

d) 2-(R)-(1-(R)-3,5-Bis(trifluoromethyl)phenyl) ethoxy)-4-(5-(dimethylaminomethyl)-1,2,3-triazol-4-yl)methyl-3-(S)-(4-fluorophenyl)morpholine Lithium aluminium hydride (0.47 ml, 1M in tetrahydrofuran) was added dropwise to a solution of the compound described in (c) above (0.11 g)in dry tetrahydrofuran (1 ml) under an inert atmosphere at 23° C. After 30 min sodium hydroxide (10 drops, 1M) was added followed by water (5 drops). Ethyl acetate (50 ml) was then added and the resulting mixture was filtered through a pad of Hyflo. The filtrate was concentrated in vacuo and the residue was purified by chromatography on silica using ethyl acetate in methanol (9:1 then 4:1) as eluant to provide the title compound as a foam. $^1$H NMR (360 MHz, CDCl$_3$) δ 1.44 (3H, d, J=6.6 Hz), 2.25 (6H, s), 2.57 (1H, td, J=3.4, 8.55 Hz), 2.90 (1H, d, J=11.7 Hz), 3.25 (1H, d, J=14.0 Hz), 3.43 (1H, d, J=13.6 Hz), 3.45 (1H, d, J=2.2 Hz), 3.53 (1H, d, J=13.6 Hz), 3.61 (1H, d, J=11.2 Hz), 3.78 (1H, d, J=14.0 Hz), 4.22 (1H, t, J=9.3 Hz), 4.32 (1H, d, J=2.2 Hz), 4.86 (1H, q, J=6.6 Hz), 7.06 (2H, t, J=8.7 Hz), 7.16 (2H, s), 7.48 (2H, br s), 7.63 (1H, s). m/z 576 (MH).

Method B 2-(R)-1-(R)-(3,5-Bis(trifluoromethyl)phenyl) ethoxy)-3-(S)-(4-fluorophenyl)-4-(4-chlorobut-2-ynyl)morpholine a) A solution of the product of Description 5 (free base, 5 g) in N,N-dimethyiformamide (20 ml) was slowly added to a heated (50° C.) solution of 1,4-dichlorbut-2-yne (2.2 ml) and potassium carbonate (4.8 g) in N,N-dimethylformamide (20 ml). The solution was heated for a further 5 h at 50° C. and then the solvent removed in vacuo. To the residue was added water (400 ml) and the product extracted into ethyl acetate (3×150 ml). The combined organic phase washed with water, saturated brine and dried (MgSO$_4$). The solvent was removed in vacuo and the residue chromatographed on silica gel (eluting with 10% ethyl acetate in petroleum ether bp 60°–80° C.) to give the title compound. $^1$H NMR (250 MHz, CDCl$_3$) δ 1.41 (3H, d, J=6.6 Hz), 2.80 (1H, app. t, J=10.8 Hz), 2.87 (1H, td, J=3.5 Hz, 11.7 Hz), 3.22 (2H, t, J=1.9 Hz), 3.52 (1H, d, J=2.8 Hz), 3.68 (1H, d, J=1.4 Hz, 11.1 Hz), 4.00 (2H, t, J=1.9 Hz), 4.22–4.32 (2H, m), 4.81 (1H, q, J=6.6 Hz), 6.96 (2H, t, J=8.7 Hz), 7.10 (2H, s), 7.31 (2H, br s), 7.56 (1H, s). m/z (Cl$^+$) 524 (M+H, 100%).

b) N-(4-Azidobut-2-ynyl)-2-(R)-(1-(R)-(3,5-bis(trifluoromethyl) phenyl)ethoxy)-3-(S)-(4-fluorophenyl)morpholine To a solution of 2-(R)-(1-(R)-(3,5-bis( trifluoromethyl)phenyl) ethoxy)-3-(S)-(4-fluorophenyl)-4-(4-chlorobut-2-ynyl)morpholine (4 g) in dimethyl sulphoxide (17 ml) was added sodium azide (0.562 g). The solution was stirred for 20 h and aqueous ammonium chloride and ethyl acetate were added. The organic phase was washed with water (2 times), saturated brine and dried (MgSO$_4$). The solvent was removed in vacuo and the residue chromatographed on silica gel (eluting with 20% ethyl acetate in petroleum ether bp 60°–80° C.) to give the title compound. $^1$H NMR (360 MHz, CDCl$_3$) δ 1.48 (3H, s, J=6.6 Hz), 2.87 (1H, app t, J=10.2 Hz), 2.98 (1H, td, J=3.6, 11.7 Hz), 3.35 (2H, t, J=1.9 Hz), 3.61 (1H, d, J=2.8 Hz), 3.72 (1H, dq, J=1.4 Hz, 10.0 Hz), 3.92 (2H, t, J=1.9 Hz), 4.30–4.40 (2H, m), 4.89(1H, q, J=6.6 Hz), 7.03 (2H, t, J=8.7 Hz), 7.17 (2H, s), 7.27 (2H, br s), 7.63 (1H, s).

c) 2-(R)-(1-(R)-3,5-Bis(trifluoromethyl)phenyl) ethoxy)-4-(5-(dimethylaminomethyl)-1,2,3-triazol-4-yl)methyl-3-(S)-(4-fluorophenyl)morpholine Dimethylamine (approximately 10 ml) was condensed at −80° C. in a pressure tube and to this was added a solution of N-(4-azidobut-2-ynyl)-2-(R)-(1-(R)-(3,5-bis(trifluoromethyl) phenyl)ethoxy)-3-(S)-(4-fluorophenyl)morpholine (3.2 g) in dioxan (15 ml). The tube was sealed and the solution was heated at 90° C. for 16 h. The solution was evaporated to dryness and the residue chromatographed on silica gel (eluting with 5% methanol in dichloromethane containing 0.25% ammonia (SG. 0.88)) and the fractions containing the desired product were evaporated in vacuo to give the title compound. To a solution of this residue in diethyl ether was added 1M-HCl in methanol. The solution was evaporated to dryness and redissolved in diethyl ether to give crystals of the title compound hydrochloride salt m.p. 194°–198° C., $[α]^{22}_D$+65.0° (C=0.5, H$_2$O). The crystals were found to be stable for at least five days at 40° C.; at 40° C./75% relative humidity; at 80° C.; and at 2000LUX.

EXAMPLE 13

2-(R)-(1-(R)-(3,5-Bis(trifluoromethyl)phenyl) ethoxy)-3-(S)-(4-fluorophenyl)-4-(N-(2-methylaminoethyl)-1,2,4-triazol-3-yl)methylmorpholine: Regioisomer B a) 2-(R)-(1-(R)-(3,5-Bis(trifluoromethyl)phenyl) ethoxy)-4-(N-carbomethoxymethyl-1,2,4-triazol-3-yl) methyl-3-(S)-(4-fluorophenyl)morpholine The compound of Description 11 (2.94 g), potassium carbonate (2.03 g) and methyl bromoacetate (0.74 ml) were heated for 45 min in dimethylformamide. The reaction was partitioned between ethyl acetate and water, washed (brine), dried (MgSO$_4$) and purified on silica using petrol-ethyl acetate mixtures. Two products, isomer A and isomer B were obtained as white foams.

Isomer A: $^1$H NMR (360 MHz, DMSO) δ 7.89 (1H, s), 7.84 (1H, s), 7.48 (3H, s), 7.33–7.30 (3H, m, J=10.1), 5.26 (1H, d, J=17.8), 5.07 (1H, d, J=17.8), 4.96 (1H, q, J=6.5), 4.39 (1H, d, J=2.8), 4.04 (1H, brt, J=10.1 Hz), 3.72 (3H, s), 3.58 (2H, d, J=14.0), 3.51 (1H, d, J=2.8), 3.20 (1H, d, J=14.0), 2.55 (1H, d, J=11.5), 2.37 (1H, brt, J=3.5), 1.40 (3H, d, J=6.6).

Isomer B: $^1$H NMR (360 MHz, DMSO) δ 8.43 (1H, s), 7.82 (1H, s), 7.44 (2H, d, J=1.4), 7.37 (2H, s), 7.31–7.25 (3H, m, J=3.2), 5.16 (2H, s), 4.91 (1H, q, J=6.5), 4.35 (1H, d, J=2.8), 4.08 (1H, br t, J=10.1), 3.69 (3H, s), 3.60 (1H, d, J=8.8), 3.55 (1H, d, J=2.7), 3.30 (1H, d, J=8.7), 3.08 (1H, d, J=13.7), 2.95 (1H, d, J=11.5), 2.47 (1H, brt, J=3.4), 1.35 (3H, d, J=6.5). MS (Cl $^+$) m/z 573 (M+1).

b) 2-(R)-(1-(R)-(3,5-Bis(trifluoromethyl)phenyl) ethoxy)-3-(S)-(4-fluorophenyl)-4-(N-(N'-methylcarboxamido)methyl-1,2,4-triazol-3-yl) methylmorpholine Monomethylamine gas was bubbled through a solution of the compound of (a) above (375 mg Isomer b) in methanol (25 ml) for 10 min and then sealed for 16 h. Reaction mixture was evaporated, redissolved in ethyl acetate and concentrated in vacuo to a white solid (374 mg). $^1$H NMR (250 MHz, CDCl$_3$) δ 8.09 (1H, s), 7.61 (1H, s), 7.45 (2H, br s), 7.33 (2H, s), 7.31 (1H, br s), 7.13 (2H, br s), 4.85 (1H, q, J=6.5 Hz), 4.76 (2H, s), 4.37 (1H, br s), 4.36 (1H, br s), 3.85 (1H, d), 3.66 (1H, br s), 3.63 (1H, br s), 3.49 (1H, d), 3.03 (1H, br s), 2.82 (3H, d), 2.80 (1H, br s), 1.46 (3H, d). MS (Cl$^+$) 573 (M$^+$+1).

c) 2-(R)-(1-(R)-(3,5-Bis(trifluoromethyl)phenyl) ethoxy)-3-(S)-(4-fluorophenyl)-4-(N-(2-methylaminoethyl)-1,2,4-triazol-3-yl) methylmorpholine A cooled solution of the compound of (b) above (302 mg) in tetrahydrofuran (5 ml) and borane-tetrahydrofuran complex (1.59 ml, 1M) was stirred for 60 min before heating (60° C.) for a further 60 min. The reaction was evaporated and redissolved in CH$_3$OH with K$_2$CO$_3$ before heating to reflux for 30 min. The reaction was poured into ethyl acetate, washed (water×2, brine), dried (MgSO$_4$). Purification on silica using CH$_3$OH-dichloromethane mixtures gave the title compound as colourless oil (54 mg). $^1$H NMR (250 MHz, CDCl$_3$) δ 7.97 (1H, s), 7.53 (1H, s), 7.39 (2H, br s), 7.29–7.23 (3H, m, J=2.6), 7.06 (2H, s), 4.77 (1H, q, J=6.6), 4.29 (1H, d, J=2.9), 4.25 (1H, brt, J=2.6), 4.13 (2H, t, J=5.7), 3.76 (1H, d, J=14.2), 3.57 (1H, t, J=3.5), 3.53 (1H, d, J=2.8), 3.31 (1H, d, J=14.1), 2.95 (1H, t, J=9.3), 2.92 (2H, t, J=5.9), 2.56 (1H, brt, J=3.5), 2.36 (3H, s), 2.16 (1H, br s), 1.37 (3H, d, J=6.6). MS (Cl$^+$) m/z 558 (M$^+$+1).

Examples 14 to 21 in Table 2 were prepared in a similar manner to that described in Example 12, Method B, via the appropriate N-(4-azidobut-2-ynyl)morpholine and the appropriate amine.

EXAMPLE 22

2-(R)-(1-(R)-(3,5-Bis(trifluoromethyl)phenyl) ethoxy)-3-(S)-phenyl-4-(1-(2-pyrrolidinoethyl)-1,2,4-triazol-3-yl)methylmorpholine a) 2-(R)-(1-(R)-(3,5-Bis(trifluoromethyl)phenyl) ethoxy)-4-(1-(2-oxo-2-pyrrolidinoethyl)-1,2,4-triazol-3-yl)methyl-3-(S)-phenylmorpholine A solution of the compound of Description 19 (2.86 g), potassium carbonate (2.37 g) and l-bromoacetylpyrrolidine (1.21 g) was heated at 60° C. in dimethylformamide (15 ml). The mixture was cooled and partitioned between water and ethyl acetate. The organic phase was washed with water, brine and dried (MgSO$_4$). The solvent was removed in vacuo and the residue was purified on silica using 1.5% methanol in dichloromethane as eluent. This afforded 2 products isomer A and isomer B.

Isomer A (Alkylation at 2 position of 1,2,4-triazole): $^1$H NMR (250 MHz, CDCl$_3$) δ 7.83 (1H, s), 7.61 (1H, s), 7.39–7.30 (5H, m), 7.16 (2H, s), 5.00 (1H, d, J=16.4 Hz), 4.88 (1H, q, J=6.6 Hz), 4.67 (1H, d, J=16.4 Hz), 4.35 (1H, d, J=2.8 Hz), 4.20 (1H, brt, J=11.6 Hz), 3.77 (1H, d, J=14.4 Hz), 3.62 (1H, dd, J=11.3 Hz), 3.51–3.44 (4H, m), 3.39 (1H, s), 3.33 (1H, d, J=14.4 Hz), 2.90 (1H, d, J=11.4 Hz), 2.74 (1H, brt, J=11.8 Hz), 2.12–2.02 (2H, m), 1.97–1.86 (2H, m), 1.45 (3H, d, J=6.6 Hz).

Isomer B (Alkylation at 1 position of 1,2,4-triazole). $^1$H NMR (250 MHz, CDCl$_3$) δ 8.19 (1H, s), 7.60 (1H, s), 7.47 (2H, br s), 7.36–7.27 (3H, m), 7.14 (2H, s), 4.89 (2H, s), 4.85 (1H, q, J=6.6 Hz), 4.36 (1H, d, J=2.8 Hz), 4.31 (1H, brt, J=11.4 Hz), 3.86 (1H, d, J=14.0 Hz), 3.60 (1H, dd, J=11.3 Hz), 3.59 (1H, d, J=2.7 Hz), 3.53–3.48 (4H, m), 3.35 (1H, d, J=14.1 Hz), 3.03 (1H, d, J=11.8 Hz), 2.60 (1H, brt, J=11.9 Hz), 2.08–2.00 (2H, m), 1.94–1.84 (2H, m), 1.44 (3H, d, J=6.6 Hz).

b) 2-(R)-(1-(R)-(3,5-Bis(trifluoromethyl)phenyl) ethoxy)-3-(S)-phenyl-4-(1-(2-pyrrolidinoethyl)-1,2,4-triazol-3-yl)methylmorpholine Lithium aluminium hydride (1.0M solution in tetrahydrofuran, 1.9 ml) was added to a solution of the compound described in (a) above (isomer B) in tetrahydrofuran (5 ml) at 0° C. The mixture was warmed to room temperature and was stirred for 1 h. The mixture was quenched (sodium hydroxide and water) and filtered through celite to remove inorganics. The flitrate was evaporated and purified on silica using 10% methanol in dichloromethane as eluent. This afforded the product as a yellow oil. $^1$H NMR (250 MHz, CDCl$_3$) δ 8.08 (1H, s), 7.60 (1H, s), 7.49 (2H, br s), 7.37–7.31 (3H, m), 7.13 (2H, s), 4.85 (1H, q, J=6.6 Hz), 4.36 (1H, d, J=2.8 Hz), 4.33–4.24 (1H, m), 4.22 (2H, t, J=6.5 Hz), 3.86 (1H, dd, J=14.1 Hz), 3.63 (1H, d, J=9.2 Hz), 3.60 (1H, d, J=2.9 Hz), 3.38 (1H, dd, J=14.0 Hz), 3.00 (1H, d, J=11.7 Hz), 2.89 (2H, t, J=6.6 Hz), 2.59 (1H, brt, J=11.9 Hz), 2.59–2.49 (4H, m), 1.79 (4H, m), 1.43 (3H, d, J=6.5 Hz).

EXAMPLE 23

2-(R)-(1-(R)-(3,5-Bis(trifluoromethyl)phenyl) ethoxy)-3-(S)-phenyl-4-(2-(2-pyrrolidinoethyl)-1,2,4-triazol-3-yl)methylmorpholine The compound described in Example 22a (isomer A) was reacted according to the procedure described in Example 22b to afford the title compound as a yellow oil. $^1$H NMR (250 MHz, CDCl$_3$) δ 7.80 (1H, s, CH), 7.61 (1H, s, ArH), 7.53–7.48 (2H, m, PhH), 7.38–7.34 (3H, m), 7.17 (2H, s), 4.88 (1H, q, J=6.5 Hz), 4.36 (1H, d, J=2.9 Hz), 4.34–4.20 (1H, m), 4.23–4.07 (3H, m), 3.83 (1H, d, J=14.0 Hz), 3.66 (1H, m), 3.42 (1H, d, J=2.8 Hz), 3.27 (1H, d, J=14.1 Hz), 2.88–2.73 (1H, m), 2.88–2.73 (2H, m), 2.88–2.73 (1H, m), 2.50 (3H, br s), 1.73 (4H, br s), 1.4 (4H, d, J=6.6 Hz).

EXAMPLE 24

2-(R)-(1-(R)-(3,5-Bis(trifluoromethyl)phenyl) ethoxy)-3-(S)-(4-fluorophenyl)-4-(5-morpholinomethyl-1,2,3-triazol-4-yl) methylmorpholine This compound was prepared by the method described in Example 12 (Method A) and purified by chromatography on silica using ethyl acetate, petroleum ether (60°–80° C.) and methanol (3:10:0, then 1:0:0 followed by 9:0:1) as eluent to afford the title compound as a white foam. $^1$H NMR (360 MHz, CDCl$_3$) δ 1.44 (3H, d, J=6.6 Hz), 2.43 (4H, m), 2.57 (1H, dd, J=11.9, 3.4 Hz), 2.90 (1H, d, J=11.6 Hz), 3.27 (1H, d, J=14.1 Hz), 3.46–3.67 (8H, m), 3.82 (1H, d, J=14.1 Hz), 4.23 (1H, m), 4.32 (1H, d, J=2.8 Hz), 4.87 (1H, m), 7.06 (2H, t, J=8.7 Hz), 7.16 (2H, s), 7.48 (2H, br s), 7.64 (1H, s). MS (ES$^+$) m/z 618 (MH$^+$, 54%).

Examples 25 to 27 in Table 2 were prepared in a similar manner to that described in Example 12, Method B, via the appropriate N-(4-azidobut-2-ynyl)morpholine and the appropriate amine.

EXAMPLE 28

2-(R)-(1-(R)-(3,5-Bis(trifluoromethyl)phenyl) ethoxy)-4-(2-chloro-5-morpholinomethyl-1,3-imidazol-4-yl)-3-(S)-(4-fluorophenyl)morpholine The product from Example 7 (0.2 g) and phosphorus oxychloride (0.5 ml) was heated at reflux for 20 hours. The mixture was cooled and partitioned between dichloromethane and aqueous potassium carbonate solution. The organic layer was washed (H$_2$O), dried (MgSO$_4$) and evaporated in vacuo. The product was purified by chromatography on silica using 100% ethyl acetate followed by 5% methanol:95% ethyl acetate to afford the title compound as an oil. MS (ES⁺) m/z 651 (MH⁺, 100%).

EXAMPLE 29

2-(R)-(1-(R)-(3,5-Bis(trifluoromethyl)phenyl) ethoxy)-4-(5-(N,N-dimethylaminomethyl)imidazol-4-yl)methyl-3-(S)-(4-fluorophenyl)morpholine 4,5-Bis(chloromethyl)imidazole hydrochloride (British Patent Specification No. GB-2,068,362-A) was reacted with the compound of Description 5 according to the procedure illustrated in Example 4 to afford the title compound as a white solid. ¹H NMR (250 MHz, CDCl₃) δ 1.44 (3H, d, J=6 Hz), 2.19 (3H, s), 2.46–2.62 (1H, m), 2.92–3.07 (2H, m), 3.25–3.44 (3H, m), 3.56–3.70 (2H, m), 4.16–4.33 (2H, m), 4.85 (1H, q, J=6 Hz), 7.01–7.17 (4H, m), 7.38–7.67 (4H, m). MS (ES) m/z 575 (M+1⁺, 100%).

EXAMPLE 30

2-(R)-(1-(R)-(3,5-Bis(trifluoromethyl)phenyl) ethoxy)-4-(5-(N,N-dimethylaminomethyl)-1,2,4-triazol-3-yl)methyl-3-(S)-(4-fluorophenyl)morpholine 3,5-Bis(chloromethyl)triazole (*J. Het. Chem.* (1986) 23, 361–368) was reacted with the compound of Description 5 according to the procedure illustrated in Example 4 to afford the title compound as a solid. ¹H NMR (250 MHz, CDCl₃) δ 1.27 (3H, d, J=6.6 Hz), 2.15 (6H, s, CH₃), 2.43 (1H, dt, J=11.7, 3.2 Hz), 2.79–2.83 (1H, m), 3.16 (1H, d, J=14.5 Hz), 3.38 (1H, d, J=2.8 Hz), 3.43–3.48 (1H, m), 3.48 (2H, s, CH₂), 3.63 (1H, d, J=14.5 Hz), 4.12 (1H, dt, J=11.7, 3.2 Hz), 4.15 (1H, d, J=2.8 Hz), 4.69 (1H, q, J=6.6 Hz), 6.85 (2H, t, J=8.75 Hz), 6.97 (2H, s), 7.27 (2H, brt), 7.45 (1H, s). MS (ES) m/z 576 (M⁺+1, 100%).

Examples 31 to 37 in Table 2 were prepared in a similar manner to that described in Example 12, Method B, via the appropriate N-(4-azidobut-2-ynyl)morpholine and the appropriate amine.

Examples 38 to 41 in Table 1 were prepared in a similar manner to that described in Example 4 from the appropriate morpholine, 4,5-bis(bromomethyl)-1,3-diacetyl-2-imidazolinone and the appropriate amine.

EXAMPLE 42

2-(R)-(1-(R)-Bis(trifluoromethyl)phenyl)ethoxy)-3-(S)-(4-fluorophenyl)-4-(2,3-dihydro-2-oxo-5-thiomorpholinomethyl-1,3-imidazol-4-yl)methylmorpholine S-oxide The compound of Example 38 (67 mg; 1 eq) was dissolved in CF₃CO₂H (0.3 ml) under N₂ then cooled to 0° C. and a solution of CF₃CO₃H (2M in CF₃CO₂H; 57 μl; 1.1 eq) was added. After stirring at 0° C. for 1 h the solvent was removed in vacuo and the residue dissolved in EtOAC and washed with saturated aqueous. NaHCO₃ solution, dried (K₂CO₃) and concentrated to leave a yellow foam. This was purified by column chromatography using MeOH/CH₂Cl₂/NH₃ (3:97:0.25) as eluant to provide the title compound as a white solid. ¹H NMR (250 MHz, CDCl₃) δ 9.48 (1H, s), 8.66 (1H, s), 7.64 (1H, s), 7.40 (2H, m), 7.14 (2H, s), 7.06 (2H, t, J=8.6 Hz), 4.87 (1H, q, J=6.5 Hz), 4.30 (1H, d, J=2.7 Hz), 4.23 (1H, t, J=10.0 Hz), 3.65 (1H, d, J=9.6 Hz), 3.45 (1H, m), 3.75 (1H, m), 3.36 (1H, d, J=2.7 Hz), 3.30 (1H, d, J=14 Hz), 3.20 (1H, d, J=14 Hz), 3.05–2.60 (9H, m), 2.36 (1H, m), 1.46 (3H, d, J=6.5 Hz).

Examples 43 to 62 in Table 2 were prepared in a similar manner to that described in Example 12, Method B, via the appropriate N-(4-azidobut-2-ynyl)morpholine and the appropriate amine.

EXAMPLE 63

2-(R)-(1-(R)-(3,5-Bis(trifluoromethyl)phenyl) ethoxy)-4-(1-(2-(N,N-disopropylamino)ethyl)-1,2,4-triazol-3-yl)methyl-3-(S)-phenylmorpholine (a) 2-(R)-(1-(R)-(3,5-Bis(trifluoromethyl)phenyl) ethoxy)-4-(1-(2-hydroxyethyl)-1,2,4-triazol-3-yl)methyl-3-(S)-phenylmorpholine The compound of Description 19 (3.90 g, 7.8 mM) was heated (60° C.) in dimethylformamide (20 ml) containing 2-bromoethanol (1.66 ml, 23.4 mM) and potassium carbonate (3.23 g, 23.4 mM) for 2 hrs. The reaction was poured into ethyl acetate and washed with water and brine, dried (MgSO₄) and evaporated. The two isomers were purified and separated on silica eluting with methanol-dichloromethane mixtures (3.06 g). MS (ES⁺) m/z 545.

(b) 2-(R)-(1-(R)-(3,5-Bis(trifluoromethyl)phenyl) ethoxy)-3-(S)-phenyl-4-(1-(2-tosyloxyethyl)-1,2,4-triazol-3-yl)methylmorpholine The alcohol from step (a), above, (1.81 g, 3.22 mM) was dissolved in dichloromethane (20 ml), tosyl chloride (1.84 g, 9.66 mM) and triethylamine (1.34 ml, 9.66 mM) were added and the reaction stirred at room temperature for 18 hrs. The solvent was removed and the residue redissolved in ethyl acetate and washed with water and brine, dried (MgSO₄) and evaporated. The product was purified on silica eluting with methanol-clichloromethane mixtures (1.87 g).

(c) 2-(R)-(1-(R)-(3,5-Bis(trifluoromethyl)phenyl) ethoxy)-4-(1-(2-(N,N-disopropylamino)ethyl)-1,2,4-triazol-3-yl)methyl-3-(S)-phenylmorpholine The tosylate from step (b), above, (0.29 g, 0.41 mM) was dissolved in dimethylformamide (5 ml), dipropylamine (0.18 ml, 1.24 mM) and triethylamine (0.18 ml, 1.24 mM) were added and the reaction heated in a sealed tube for 18 hrs. The residue was dissolved in ethyl acetate, washed with water and brine, dried (MgSO₄) and evaporated. Purification on silica eluting with methanol-dichloromethane mixtures afforded the title compound (0.095 g). ¹H NMR (360 MHz, d₆-DMSO) δ 8.31 (1H, s), 7.82 (1H, s), 7.46–7.42 (2H, m), 7.36 (2H, s), 7.32–7.22 (3H, m), 4.89–4.92 (1H, q, J=6.5 Hz), 4.34 (1H, d, J=2.8 Hz), 4.18–4.04 (3H, m), 3.60–3.56 (3H, m), 3.09 (1H, d, J=13.6 Hz), 3.94 (1H, d, J=11.5 Hz), 2.71 (2H, t, J=5.8 Hz), 2.44–2.40 (1H, m), 2.30 (4H, t, J=7.0 Hz), 1.34 (3H, d, J=6.5 Hz), 1.32–1.20 (4H, m) and 0.73 (6H, t, J=7.4 Hz). M/S⁺ 628.

Examples 64 to 74 in Table 3 were prepared in a similar manner to that described in Example 63 from the appropriate 1,2,4-triazol-3-ylmethylmorpholine and the appropriate amine.

EXAMPLE 75

2-(R)-(1-(R)-3,5-Bis(trifluoromethyl)phenyl) ethoxy)-4-(5-(N,N-dimethylaminomethyl)-1,2,4-triazol-3-yl)methyl-3-(S)-(4-fluorophenyl)morpholine (a) 2-(R)-(1-(R)-3,5-Bis(trifluoromethyl)phenyl)ethoxy)-3-(S)-(4-fluorophenyl)-4-(1-(tetrahydro-2-pyranyl)-5-(N,N-dimethylaminomethyl)-1H-1,2,4-triazol-3-yl)methylmorpholine The compound of Description 5 (1 g, 2.28 mM) was dissolved in isopropanol (20 ml), 3,5-bis(chloromethyl)-1-

(tetrahydro-2-pyranyl)-1H-1,2,4-triazole (1.14 g, 4.57 mM) (prepared by method of Bradshaw, *J. Het. Chem.* (1986), 23, 361) and potassium carbonate (0.95 g, 6.84 mM) were added and the reaction heated to 60° C. for 18 hrs. Dimethylamine (3 eq) was then added and the reagents transferred to a sealed tube and heated for a further 18 hrs. The solvents were then removed and the residue purified on silica eluting with methanol dichloromethane-ammonia mixtures to yield the title compound (0.62 g).

(b) 2-(R)-(1-(R)-3,5-Bis(trifluoromethyl)phenyl) ethoxy)-4-(5-(N,N-dimethylaminomethyl)-1,2,4-triazol-3-yl)-methyl-3-(S)-(4-fluorophenyl)morpholine The protected amine from step (a), above, (0.62 g, 0.94 mM) was dissolved in methanol (15 ml) and treated with HCl in methanol (1N, 25 ml) and stirred at room temperature for 1 hour. The solvent was then removed and the residue purified on silica eluting with methanol-dichloromethane ammonia mixtures to yield the title compound (0.48 g). $^1$H NMR (250 MHz, CDCl$_3$) δ 7.45 (1H, s), 7.30–7.22 (2H, m), 6.97 (2H, s), 6.85 (2H, t, J=8.7 Hz), 4.72–4.66 (1H, q, J=6.5 Hz), 4.15 (1H, d, J=2.8 Hz), 4.15–4.07 (1H, m), 3.63 (1H, d, J=14.4 Hz), 3.48 (4H, s), 3.44–3.41 (1H, m), 3.38 (1H, d, J=2.8 Hz), 3.16 (1H, d, J=14.5 Hz), 2.81 (1H, d, J=11.1 Hz), 2.50–2.39 (1H, m), 2.15 (6H, s) and 1.27 (3H, d, J=6.6 Hz). M/S ES$^+$ 576.

EXAMPLE 76

4-(5-(N,N-Dimethylaminomethyl)-1,2,3-triazol-4-yl)methyl-3-(S)-(4-fluorophenyl)-2-(R)-(1-(R)-(3-methylthio-5-(trifluoromethyl)phenyl)ethoxy)-morpholine The compound of Example 57 (270 mg, 0.51 mmol) was heated to 120° C. with sodium thiomethoxide (178 mg, 2.55 mmol) in anhydrous DMF (10 ml) for between 2–5 hours. The cooled solution was diluted with water (150 ml), extracted with ethyl acetate (4×40 ml), dried (MgSO$_4$) and concentrated in vacuo to a crude oil (372 mg) which was purified by flash silica gel chromatography in 5–10% methanol/dichloromethane to yield the title compound as a viscous gum/glass (170 mg, 60%). $^1$H NMR (360 MHz, CDCl$_3$) δ 1.31 (3H, d, J=6.6 Hz), 2.17 (6H, s), 2.28 (3H, s), 2.47 (1H, dt, J=12.1, 3.4 Hz), 2.82 (1H, d, J=11.6 Hz), 3.14 (1H, d, J=13.9 Hz), 3.35 (2H, m), 3.46 (1H, d, J=13.5 Hz), 3.52 (1H, dd, J=11.2, 1.9 Hz), 3.70 (1H, d, J=13.9 Hz), 4.14 (1H, dr, J=11.6 Hz), 4.26 (1H, d, J=2.7 Hz), 4.66 (1H, q, J=6.5 Hz), 6.64 (2H, s), 6.99 (2H, t, J=8.6 Hz), 7.11 (1H, s), 7.41 (2H, br s), 10.0–10.8 (1H, vbr s); MS (ES$^+$) m/z 554 (M+1, 100%).

EXAMPLE 77

3-(S)-(4-Fluorophenyl)-2-(R)-(1-(R)-(3-methylthio-5-(trifluoromethyl)phenyl)ethoxy)-4-(5-pyrrolidinomethyl-1,2,3-triazol-4-yl)methylmorpholine The title compound was prepared from the compound of Example 18 according to the method of Example 76 as a foam (620 mg, 81%). $^1$H NMR (360 MHz, CDCl$_3$) δ 1.40 (3H, d, J=6.6 Hz), 1.79 (4H, br s), 2.36 (3H, s), 2.5–2.6 (5H, m), 2.87 (1H, d, J=11.7 Hz), 3.23 (1H, d, J=13.9 Hz), 3.43 (1H, d, J=2.8 Hz), 3.57–3.64 (2H, m), 3.71 (1H, d, J=13.7 Hz), 3.78 (1H, d, J=14.0 Hz), 4.21 (1H, m), 4.33 (1H, d, J=2.8 Hz), 4.74 (1H, q, J=6.5 Hz), 6.71 (2H, s), 7.06 (2H, t, J=8.7 Hz), 7.19 (1H, s), 7.47 (2H, br s); MS (ES$^+$) m/z 580 (M+1, 100%).

EXAMPLE 78

3-(S)-(4-Fluorophenyl)-2-(R)-(1-(R)-(3-methylthio-5-trifluoromethyl)phenyl)ethoxy)-4-(5-morpholinomethyl-1,2,3-triazol-4-yl)methylmorpholine The title compound was prepared from compound of Example 19 according to the method of Example 76 as a foam (126 mg, 66%). $^1$H NMR (360 MHz, CDCl$_3$) δ 1.40 (3H, s, J=6.6 Hz), 2.37 (3H, s), 2.32–2.49 (4H, m), 2.54 (1H, dr, J=11.9, 3.4 Hz), 2.90 (1H, d, J=11.7 Hz), 3.25 (1H, d, J=13.9 Hz), 3.48 (1H, d, J=13.5 Hz), 3.57–3.68 (7H, m), 3.82 (1H, d, J=14.1 Hz), 4.23 (1H, m), 4.35 (1H, d, J=2.8 Hz), 4.75 (1H, q, J=6.5 Hz), 6.71 (2H, s), 7.06 (2H, t, J=8.7 Hz), 7.19 (1H, s), 7.49 (2H, br s); MS (ES$^+$) m/z 596 (M+1, 55%), 203 (100%).

EXAMPLE 79

4-(5-(N,N-Dimethylaminomethyl)-1,2,3-triazol-4-yl)methyl-2-(R)-(1-(R)-(3-methylthio-5-(trifluoromethyl)phenyl)ethoxy)-3-(S)-phenylmorpholine The title compound was prepared from the triazole of Example 102 according to the method of Example 76 as a foam (116 mg, 6%). $^1$H NMR (250 MHz, CDCl$_3$) δ 1.39 (3H, d, J=6.5 Hz), 2.24 (6H, s), 2.32 (3H, s), 2.59 (1H, dr, J=11.8, 3.3 Hz), 3.25 (1H, d, J=13.8 Hz), 3.38–3.44 (2H, m), 3.52 (1H, d, J=13.6 Hz), 3.62 (1H, dd, J=11.2, 1.8 Hz), 3.81 (1H, d, J=13.9 Hz), 4.23 (1H, m), 4.39 (1H, d, J=2.6 Hz), 4.75 (1H, q, J=6.5 Hz), 6.71 (2H, s), 7.17 (1H, s), 7.34–7.41 (3H, m), 7.49 (2H, br s); MS (ES$^+$) m/z 536 (M+1, 100%).

EXAMPLE 80

4-(5-(N,N-Dimethylaminomethyl)-1,2,3-triazol-4-yl)methyl-3-(S)-(4-fluorophenyl)-2-(R)-(1-(R)-(3-tert-butylthio-5-(trifluoromethyl)phenyl)ethoxy)-morpholine The title compound was prepared from the compound of Example 57 according to the method of Example 76 as a foam (117 mg, 68%). $^1$H NMR (360 MHz, CDCl$_3$) δ 1.19 (9H, s), 1.42 (3H, d, J=6.6 Hz), 2.23 (6H, s), 2.57 (1H, dt, J=12.0, 3.8 Hz), 2.92 (1H, d, J=11.6 Hz), 3.24 (1H, d, J=13.9 Hz), 3.39–3.44 (2H, m), 3.51 (1H, d, J=14.8 Hz), 3.62 (1H, m), 3.80 (1H, d, J=13.9 Hz), 4.23 (1H, m), 4.41 (1H, d, J=2.7 Hz), 4.77 (1H, q, J=6.5 Hz), 6.89 (1H, s), 7.14 (1H, s), 7.31–7.35 (3H, m), 7.46 (2H, br s), 7.51 (1H, s); MS (ES$^+$) m/z 578 (M+1, 100%).

EXAMPLE 81

4-(5-(N,N-Dimethylaminomethyl)-1,2,3-triazol-4-yl)methyl-3-(S)-(4-fluorophenyl)-2-(R)-(1-(R)-(3-methylsulphinyl-5-(trifluoromethyl)phenyl)ethoxy)-morpholine The thioether of Example 76 (155 mg, 0.28 mmol) was dissolved in trifluoroacetic acid (800 μl) cooled to 0° C. and treated with a 2.0M solution of trifluoroperacetic acid in trifluoroacetic acid (153 μl, 0.308 mmol), with stirring for 30 minutes. The reaction mixture was poured into 0.5M sodium bicarbonate solution (50 ml), extracted with dichloromethane (3×15 ml), dried (MgSO$_4$) and concentrated in vacuo. The resulting crude solid (200 mg) was purified by flash silica gel chromatography in 8% methanol:dichloromethane to yield the title compound as unresolved stereoisomers as a white foam (81 mg, 51%). $^1$H NMR (360

MHz, CDCl$_3$) δ 1.44 and 1.46 (3H total, 2×d, J=6.6 Hz), 2.24 (6H, s), 2.56 (1H, m), 2.59 and 2.62 (3H total, 2×s), 2.88 (1H, d, J=11.9 Hz), 3.23 and 3.26 (1H total, 2×d, J=13.9 Hz), 3.42–3.55 (3H, m), 3.62 (1H, br d, J=11.3 Hz), 3.75 and 3.79 (1H total, 2×d, J=14.4 Hz), 4.22 (1H, m), 4.32 and 4.35 (1H total, 2×d, J=2.7 Hz), 4.89 (1H, m), 6.85 (½H, s), 7.04–7.13 (3H, m), 7.24 (½H, s), 7.50 (2H, br s), 7.73 and 7.75 (1H total, 2×s); MS (ES$^+$) m/z 570 (M+1, 100%).

EXAMPLE 82

3-(S)-(4-Fluorophenyl)-2-(R)-(1-(R)-(3-methylsulphinyl-5-(trifluoromethyl)phenyl)ethoxy)-4-(5-pyrrolidinomethyl-1,2,3-triazol-4-yl)methylmorpholine The title compound as an unresolved mixture of stereoisomers was prepared from Example 77 according to the method of Example 81 as a foam (90 mg, 63%). $^1$H NMR (360 MHz, CDCl$_3$) δ 1.44 and 1.46 (3H total, 2×d, J=6.6), 1.86 (4H, br s), 2.50–2.60 (1H, m), 2.59 and 2.62 (3H total, 2×s), 2.70–2.90 (5H, m), 3.24 and 3.26 (1H, 2×d, J=14.0), 3.46 (1H, d, J<2), 3.62 (1H, br d, J=11.2) 3.71–3.86 (3H, m), 4.20 (1H, m), 4.32 and 4.35 (1H total, 2×d, J=2.7), 4.89 (1H, m), 6.89 (½H, s), 7.03–7.13 (3H, m), 7.25 (½H, s), 7.49 (2H, br s), 7.73 and 7.75 (1H total, 2×s); MS (ES$^+$) m/z 596 (M+1), 100%).

EXAMPLE 83

3-(S)-(4-Fluorophenyl)-2-(R)-(1-(R)-(3-methylsulphinyl-5-(trifluoromethyl)phenyl)ethoxy)-4-(5-morpholinomethyl-1,2,3-triazol-4-yl)methylmorpholine The title compound as an unresolved mixture of stereoisomers was prepared from Example 78 according to the method of Example 81 as a foam (113 mg, 92%). $^1$H NMR (360 MHz, CDCl$_3$) δ 1.3 and 1.41 (3H total, 2×d, J=6.6), 2.54 and 2.57 (3H total, 2×s), 2.54–2.65 (1H, m), 2.82–2.89 (1H, m), 3.05–3.25 (4H, vbr s), 3.35 (1H, m), 3.50 (1H, m), 3.61 (1H, m), 3.72 and 3.74 (1H, 2×d, J=14.5), 3.85–4.22 (6H, m), 4.29 and 4.33 (1H, 2×d, J=2.5), 4.81 (1H, m), 6.99–7.09 (3½H, m), 7.30 (½H, s), 7.42 (2H, br s), 7.64 and 7.66 (1H total, 2×s); MS (ES$^+$) m/z 612 (M+1, 100%).

EXAMPLE 84

3-(S)-(4-Fluorophenyl)-2-(R)-(1-(R)-(3-methylsulphonyl-5-(trifluoromethyl)phenyl)ethoxy)-4-(5-morpholinomethyl-1,2,3-triazol-4-yl)methylmorpholine The sulphoxide of Example 83 (78 mg, 0.128 mmol) was dissolved in trifluoroacetic acid (500 μl) cooled to 0° C. and treated with a 2.0M solution of trifluoroperacetic acid in trifluoroacetic acid (70 μl, 0.140 mmol) with stirring for 2½ hours. A further equivalent of trifluoroperacetic acid (70 μl, 0.140 mmol) was added after this time and the product purified after 3 hours according to the method of Example 81 to yield the title compound as a foam (27 mg, 34%). $^1$H NMR (360 MHz, CDCl$_3$) δ 1.47 (3H, d, J=6.6 Hz), 2.38–2.45 (4H, m), 2.57 (1H, dr, J=11.9, 3.5), 2.90 (1H, d, J=11.7 Hz), 2.96 (3H, s), 3.26 (1H, d, J=14.0 Hz), 3.46–3.51 (2H, m), 3.56–3.68 (6H, m), 3.79 (1H, d, J=14.1 Hz), 4.22 (1H, m). 4.35 (1H, d, J=2.8 Hz), 4.90 (1H, q, J=6.8 Hz), 7.07 (2H, t, J=8.6 Hz), 7.17 (1H, s), 7.50 (2H, br d), 7.67 (1H, s), 7.97 (1H, s); MS (ES$^+$) m/z 628 (M+1, 100%).

EXAMPLE 85

2-(R)-(1-(R)-(3,5-Bis(trifluoromethyl)phenyl)ethoxy)-3-(S)-(4-fluorophenyl)-4-(2-(5-((S)-(+)-2-methoxymethylpyrrolidinomethyl)-1,2,3-triazol-4-yl)ethyl)morpholine Step A 2-(R)-(1-(R)-(3,5-Bis(trifluoromethyl) phenyl)ethoxy)-4-(but-3-ynyl)-3-(S)-(4-fluorophenyl)morpholine A solution of Description 5 (1.24 g; 1 eq), 3-butyn-1-ol-tosylate (1.43 g; 2.5 eq), K$_2$CO$_3$ (1.32 g; 3.7 eq) and NaI (cat) in dry DMF (7 ml) was heated at 100° C. for 12 h. After cooling to room temperature the reaction mixture was partitioned between H$_2$O and EtOAc. The layers were separated and the aqueous phase extracted with EtOAc (2×). The combined organic phases were dried (MgSO$_4$) and concentrated and the residue purified by chromatography (hexanes/EtOAc 9:1→4:1) to provide the title compound as a clear cololourless oil. MS m/z 490 (MH$^+$).

Step B 2-(R)-(1-(R)-(3,5-Bis(trifluoromethyl) phenyl)ethoxy)-3-(S)-(4-fluorophenyl)-4-(4-hydroxybut-3-ynyl) morpholine The acetylene of Step A (1.2 g; 1.0 eq) was dissolved in dry THF (5 ml) then cooled to −78° C. and n-BuLi (2.5M in hexane; 1 ml; 1.05 eq) was added. The reaction mixture was stirred at −78° C. for 1 h, then HCHO gas was bubbled through the solution until it was saturated. The reaction mixture was warmed to room temperature and stirred for 1 h. Work-up (NH$_4$Cl/EtOAc) followed by purification on silica gel (hexanes/EtOAc 9:1→4:1) provided the title compound as a clear, viscous oil. MS m/z 520 (MH$^+$).

Step C 2-((R)-(1-(R)-(3,5-Bis(trifluoromethyl) phenyl)ethoxy)-4-(4-chlorobut-3-ynyl)-3-(S)-(4-fluorophenyl) morpholine The alcohol of Step B (0.42 g; 1 eq) was dissolved in dry THF (5 ml) under N$_2$ and triphosgene (84 mg; 0.35 eq) was added followed by pyridine (128 μl; 2.0 eq). The reaction mixture was stirred at room temperature for ½ h, then diluted with EtOAc and washed with H$_2$O and brine, dried (MgSO$_4$) and concentrated to leave a yellow oil. This was purified by chromatography (hexanes/EtOAc 9:1→4:1) to provide the title compound as a clear, viscous oil. MS m/z 538, 540 (MH$^+$).

Step D N-(4-Azidobut-3-ynyl)-2-(R)-(1-(R) -(3,5-bis(trifluoromethyl)phenyl)ethoxy)-3-(S)-(4-fluorophenyl)morpholine The chloride of Step C (0.23 g; 1 eq) and NaN$_3$ (31 mg; 1 eq) in DMSO (0.8 ml) was stirred at room temperature for 14 h. Work-up (NH$_4$Cl/EtOAc) provided the title compound as an oil, which was used without further purification.

Step E 2-(R)-(1-(R)-(3,5-Bis(trifluoromethyl) phenyl)ethoxy)-3-(S)-(4-fluorophenyl)-4-(2-(5-((S)-(+)-2-methoxymethylpyrrolidinomethyl)-1,2,3-triazol-4-yl) ethyl)-morpholine A solution of the azide of Step D (0.205 g; 1 eq) and (S)-(+)-2-methoxymethylpyrrolidine (114 μl; 3 eq) was heated at 80° C. under N$_2$ the solvent was removed in vacuo and the residue purified by chromatography using CH$_2$Cl$_2$/MeOH/NH$_3$ (98:2:0.1 then 97:3:0.1) as eluant to provide the title compound as a white foam. $^1$H NMR (250 MHz, CDCl$_3$) δ 7.62 (1H, s), 7.24 (2H, m), 7.14 (2H, s), 6.95 (2H, t, J=8.7 Hz), 4.87 (1H, q, J=6.5 Hz), 4.30 (2H, m), 3.95 (1H, d, J=14 Hz), 3.70 (1H, dd, J=2, 11.3 Hz), 3.53–3.34 (7H, m), 3.19 (1H, d, J=11.6 Hz), 2.86–2.56 (6H, m), 2.29 (1H, m), 2.09 (1H, m), 1.88 (1H, m), 1.70 (3H, m), 1.45 (3H, d, J=6.5 Hz). MS m/z=660.

EXAMPLE 86

2-(R)-(1-(S)-(3,5-Bis(trifluoromethyl)phenyl)-2-hydroxyethoxy)-4-(5-(N,N-dimethylaminomethyl)-1,2,3-triazol-4-yl)methyl-3-(S)-(4-fluorophenyl)morpholine Step A 2-(R)-(1-(S)-(3,5-Bis(trifluoromethyl)phenyl)-2-tert-butyldimethylsilyloxyethoxy)-3-(S)-(4-fluorophenyl)-morpholine The product from Description 21 (2 g) was dissolved in anhydrous dichloromethane (16 ml), under nitrogen, and cooled to 0° C. 2,6-Lutidine (0.5 ml) and tert-butyldimethyltrifluoromethane sulfonate (1.0 ml) were then added and the mixture stirred for 15 mins. The reaction mixture was washed ($H_2O$, brine), dried ($MgSO_4$) and evaporated in vacuo. Purification by gravity silica column using 20%–50% ethylacetate/petrol as eluant afforded the title compound as a colourless oil. $^1$H NMR (250 MHz, CDCl$_3$) δ −0.04 (3H, s), 0.00 (3H, s), 0.87 (9H, s), 3.15–3.36 (2H, m), 3.64–3.70 (2H, m), 3.90–3.96 (1H, m), 4.10 (1H, d, J=2.2 Hz), 4.22–4.53 (1H, m), 4.53 (1H, d, J=2.2 Hz), 4.91 (1H, t, J=5.9 Hz), 7.04–7.14 (2H, m), 7.29–7.36 (4H, m), 7.74 (1H, br s). MS (ES$^+$) m/z=567.

Step B 2-(R)-(1-(S)-(3,5-Bis(trifluoromethyl) phenyl)-2-tert-butyldimethylsilyloxyethoxy)-3-(S)-(4-fluorophenyl)-4-(4-chlorobut-2-ynyl)morpholine Prepared in an analogous fashion to Step (a) of Example 12, Method B, using the product from Step A, above, to afford the title compound as a clear oil. $^1$H NMR (360 MHz, CDCl$_3$) δ 0.00 (3H, s), 0.04 (3H, s), 0.91 (9H, s), 2.95–3.09 (2H, m), 3.40 (2H, br s), 3.72–3.83 (3H, m), 4.01 (1H, dd, J=10.2, J=5.5 Hz), 4.25 (2H, m), 4.50 (2H, m), 4.9 (1H, t, J=5.9 Hz), 7.15 (2H, t, J=8.7 Hz), 7.29 (2H, s), 7.52 (2H, br s), 7.76 (1H, s).

Step C 2-(R)-(1-(S)-(3,5-Bis(trifluoromethyl) phenyl)-2-tert-butyldimethylsilyloxyethoxy)-4-(5-(N,N-dimethylaminomethyl)-1,2,3-triazol-4-yl)methyl-3-(S)-(4-fluorophenyl)-morpholine Prepared in an analogous fashion to Steps (b) and (c) of Example 12, Method B, using the product of Step B, above, to afford the title compound. $^1$H NMR (250 MHz, CDCl$_3$) δ −0.02 (3H, s), 0.00 (3H, s), 0.88 (9H, s), 2.30 (6H, s), 2.60–2.70 (1H, m), 2.93–2.98 (1H, br d, J=11.6 Hz), 3.30 (1H, d, J=13.8 Hz), 3.48–3.63 (3H, m), 3.68–3.74 (2H, m), 3.84–3.97 (2H, m), 4.33–4.41 (1H, m), 4.46 (1H, d, J=2.8 Hz), 4.90 (1H, t, J=5.6 Hz), 7.16 (2H, t, J=8.7 Hz), 7.25 (2H, br s), 7.59 (2H, vbr m), 7.74(1H, br s).

Step D 2-(R)-(1-(S)-(3,5-Bis(trifluoromethyl) phenyl)-2-hydroxyethoxy)-4-(5-(N,N-dimethylaminomethyl)-1,2,3-triazol-4-yl)methyl-3-(S)-(4-fluorophenyl)morpholine The product of Step C, above, (0.2 g) was stirred in anhydrous tetrahydrofuran (2 ml) with tetrabutylammonium fluoride (1.0M) in tetrahydrofuran (0.42 ml) for 30 minutes. The mixture was partitioned between ammonium chloride solution and ethylacetate, and the organic layer washed ($H_2O$, brine), dried ($MgSO_4$) and evaporated in vacuo. Purification by gravity silica column eluting with 4–10% MeOH/0.1% NH$_4$OH/dichloromethane afforded the title compound. $^1$H NMR (250 MHz, CDCl$_3$) δ 2.26 (6H, s), 2.51 (1H, m), 3.09 (2H, m), 3.35 (2H, m), 3.51–3.63 (4H, m), 3.78 (2H, d, J=13.8 Hz), 4.30–4.36 (2H, m), 4.88 (1H, m), 7.01–7.10 (4H, m), 7.50 (1H, vbr s), 7.59 (1H, br s).

EXAMPLE 87

2-(R)-(1-(R)-(3,5-Bis(trifluoromethyl)phenyl) ethoxy)-4-(5-N-ethyl-N-isopropylaminomethyl)-1 (or 2 or 3)-methyl-1,2,3-triazol-4-yl)methyl-3-(S)-phenylmorpholine The product from Example 101 (2 g) was dissolved in N,N-dimethylformamide (4 ml) at room temperature under nitrogen. Iodomethane was added, followed by sodium hydride (60%) (14 mg) and the mixture stirred for 16 hours. The reaction mixture was partitioned between ethylacetate and water and the organic layer was washed ($H_2O \times 2$, brine), dried ($MgSO_4$) and evaporated in vacuo. Purification by gravity silica chromatography eluting with 100% ethylacetate followed by 10% methanol/0.1% NH$_4$OH/dichloromethane afforded the title compound.

$^1$H NMR (250 MHz, CDCl$_3$) δ 0.85–1.02 (9H, m), 1.44 (3H, d, J=6.6 Hz), 2.25–2.40 (2H, m), 2.57–2.68 (1H, m), 2.75–2.85 (1H, m), 2.96 (1H, br d, J=13.5 Hz), 3.15 (1H, d, J=13.5 Hz), 3.38 (1H, d, J=2.7 Hz), 3.44 (2H, s), 3.60–3.73 (2H, m), 4.07 (3H, s), 4.18 (1H, m), 4.35 (1H, d, J=2.8 Hz), 4.83 (1H, m), 7.15 (2H, br s), 7.33 (3H, m), 7.48 (2H, vbr s), 7.61 (1H, br s). MS (ES$^+$) m/z=613 (MH$^+$, 100%).

EXAMPLE 88

2-(R)-(1-(S)-(3,5-Bis(trifluoromethyl)phenyl)-2-hydroxyethoxy)-3-(S)-(4-fluorophenyl)-4-(2,3-dihydro-3-oxo-1,2,4-triazol-5-yl)methylmorpholine The compound of Description 6 (0.5 g), N-carbomethoxy-2-chloroacetamidrazone (Description 23) (182 mg) and potassium carbonate (0.3 g) were suspended in dimethylformamide (3.6 ml) and the mixture was heated to 60° C. for 2 h. The mixture was then heated to 140° C. for a further 2 h. The mixture was cooled and the inorganic material was removed by filtration through celite. The solvent was removed in vacuo by azeotroping with xylene. The residue was purified on silica by flash chromatography using 1–10% methanol in dichloromethane. This afforded the title compound as a white powder (300 mg). $^1$H NMR (360 MHz, DMSO-d$_6$) δ 2.38–2.41 (1H, m), 2.78 (1H, d, J=14.0 Hz), 2.81–2.84 (1H, m), 3.36 (1H, d, J=14.0 Hz), 3.45–3.48 (1H, m), 3.52 (1H, d, J=3.0 Hz), 3.58–3.61 (2H, m), 4.81 (1H, t, J=6.0 Hz), 4.88 (1H, br t), 7.09 (2H, t, J=9.0 Hz), 7.33 (2H, s), 7.50 (2H, br t), 7.85 (1H, s), 11.26 (1H, s), 11.30 (1H, s). MS (Cl$^+$) m/z 551 (M+1, 10%), 454 (M$^+$-CH$_2$triazolone, 20).

EXAMPLE 89

2-(R)-(1-(S)-(3,5-Bis(trifluoromethyl)phenyl)-2-hydroxyethoxy)-3-(S)-(4-fluorophenyl)-4-(1,2,4-triazol-3-yl)methylmorpholine The compound of Description 6 (270 mg), anhydrous potassium carbonate (250 mg), and N-formyl-2-chloroacetamidhydrazone (92 mg) (prepared according to I. Yanagisawa, *J. Med. Chem.* (1984), 27, 849) were heated at 60° C. in anhydrous dimethylformamide for 1 h and then at 140° C. for 2 h. The reaction mixture was cooled and diluted with water (100 ml). The product was extracted into ethyl acetate (3×50 ml) and the organic layer was washed with brine, dried ($MgSO_4$) and evaporated in vacuo. The residue was purified by chromatography on silica using 7% methanol in dichloromethane as the eluant. This afforded the title compound (200 mg, 60%) as a white solid. $^1$H NMR (360 MHz, DMSO-d$_6$) δ 2.47 (1H, t, J=9.0 Hz), 2.89 (1H, d, J=11.0 Hz), 3.18 (1H, d, J=14.0 Hz), 3.44–3.49 (1H, m), 3.55–3.61 (4H, m), 3.64 (1H, d, J=6 Hz), 4.25 (1H, t, J=11.0 Hz), 4.34 (1H, d, J=3.0 Hz), 4.81 (1H, t, J=5.0 Hz), 7.11 (2H, t, J=9.0 Hz), 7.34 (2H, s), 7.52 (2H, m), 7.85 (1H, s), 8.19 (1H, br s). MS (Cl) m/z 535 (M+1, 10%).

EXAMPLE 90

4-(2,3-Dihydro-3-oxo-1,2,4-triazol-5-yl)methyl-3-(S)-(4-fluorophenyl)-2-(R)-(1-(S)-(3-fluoro-5-(trifluoromethyl)phenyl)-2-hydroxyethoxy)morpholine The compound of Description 22 (350 mg), N-carbomethoxy -2-chloroacetamidrazone (150 mg) (Description 23) and potassium carbonate (150 mg) in dimethylformamide were heated at 60° C. for 3 h until all starting material was consumed. The mixture was then heated at 140° C. for 3 h. The mixture was cooled and filtered through celite to remove inorganics. The residue was evaporated using xylene to azeotrope residual dimethylformamide. The residue was purified by chromatography on silica using 1–10% methanol in dichloromethane as eluant. This afforded the title compound as a foam which was recrystallised from ether. $^1$H NMR (360 MHz, DMSO-d$_6$) δ 2.34–2.46 (1H, m), 2.74–2.84 (2H, m), 3.34–3.43 (3H, m), 3.50–3.60 (2H, m), 4.21–4.31 (2H, m), 4.68 (1H, t, J=5.0 Hz), 4.90 (1H, t, J=7.0 Hz), 6.54 (1H, d, J=9.0 Hz), 6.88 (1H, s), 7.14 (t, J=9.0 Hz), 7.42 (1H, d, J=9.0 Hz), 7.44 (2H, m).

EXAMPLE 91

4-(2,3-Dihydro-2-oxo-1,3-imidazol-4-yl)methyl-2-(R)-(1-(S)-(3,5-bis(trifluoromethyl)phenyl)-2-hydroxyethoxy)-3-(S)-(4-fluorophenyl)morpholine A mixture of the compound of Description 6 (2 g), 4-bromomethyl-1,3-diacetyl-2-imidazolone (1.38 g) (prepared by the method of Dolan and Dushinsky, JACS (1948) 70, 657) and potassium carbonate (1.2 g) in dimethylformamide (14 ml) was stirred at room temperature for 30 minutes until all starting morpholine had reacted. The mixture was diluted with water (150 ml) and extracted with ethyl acetate (3×50 ml). The combined extracts were washed with brine and the organic solvent was evaporated in vacuo. The residual oil was dissolved in ethanol (20 ml) and methylamine (2 ml of 8M soln. in ethanol) was added. This solution was stirred for 1 h and the solvent was then removed in vacuo. The residual oil was purified on silica using 1–10% methanol in dichloromethane as eluant. This afforded the product (2 g, 83%) as a white foam. This was further characterised by treatment with methanolic hydrogen chloride to afford a white solid which was recrystallised from water. $^1$H NMR (360 MHz, DMSO-d$_6$) δ 2.22–2.34 (1H, m), 2.62 (1H, d, J=14.0 Hz), 2.89 (1H, app d, J=11.0 Hz), 3.26 (1H, d, J=14.0 Hz), 3.38 (1H, d, J=3.0 Hz), 3.43–3.50 (1H, m), 3.57–3.62 (2H, m), 4.19–4.28 (1H, m), 4.32 (1H, d, J=3.0 Hz), 4.81 (1H, t, J=5.5 Hz), 4.93 (1H, t, J=6.0 Hz), 6.00 (1H, s), 7.09 (1H, t, J=9.0 Hz), 7.33 (2H, s), 7.54 (2H, br t), 7.86 (1H, s), 9.63 (1H, s), 9.83 (1H, s). MS (Cl) m/z 550 (M+1, 20%), 454 (80) 116 (100).

EXAMPLE 92

4-(2,3-Dihydro-2-oxo-5-pyrrolidinomethyl-1,3-imidazol-4-yl)methyl-2-(R)-(1-(S)-(3,5-bis(trifluoromethyl)phenyl)-2-hydroxyethoxy)-3-(S)-(4-fluorophenyl)morpholine A mixture of the compound of Description 6 (1.8 g), 4,5-bis(bromomethyl)-1,3-diacetyl-2-imidazolone (prepared by the method of Dolan and Dushinsky, JACS (1948) 70, 657) (2.2g) and potassium carbonate in dimethylformamide (13 ml) were stirred at room temperature for 10 min until all starting material was reacted. To the resulting brown mixture was added dropwise pyrrolidine (1.65 ml, excess) resulting in an exothermic reaction. The solvent was removed in vacuo and the residue was extracted with ethyl acetate (3×50 ml) and washed with brine. The organic phase was dried (MgSO$_4$) and the solvent removed in vacuo. The brown residue was purified by medium pressure reverse phase C$_{18}$ silica gel chromatography using 30% acetonitrile in 0.1% aqueous trifluoroacetic acid as eluant. This afforded the title product as a buff coloured solid (1 g). $^1$H NMR (360 MHz, DMSO -d$_6$) δ 1.61 (4H, br s), 2.26–2.30 (5H, m), 2.66 (1H, d, J=14.0 Hz), 2.83–2.87 (1H, brd), 3.02 (1H, d, J=13.5 Hz), 3.15 (1H, d, J=13.5 Hz), 3.23 (1H, d, J=14.0 Hz), 3.37 (1H, d, J=3.0 Hz), 3.42–3.47 (1H, m), 3.57–3.60 (2H, m), 4.17–4.24 (1H, m), 4.32 (1H, d, J=3.0 Hz), 4.79 (1H, t, J=5.5 Hz), 4.89 (1H, t, J=5.5 Hz), 7.08 (2H, t, J=9.0 Hz), 7.32 (2H, s), 7.56 (2H, mc), 7.85 (1H, s), 9.61 (1H, s), 9.65 (1H, s). MS (Cl$^+$) m/z 633 (M$^+$+1), 454 (50%).

EXAMPLE 93

2-(R)-(1-(S)-(3,5-Bis(trifluoromethyl)phenyl)-2-phosphoryloxyethoxy)-3-(S)-(4-fluorophenyl)-4-(2,3-dihydro-3-oxo-1,2,4-triazol-5-yl)methylmorpholine The compound of Example 88 (200 mg) in dry tetrahydrofuran (1 ml) was treated with dibenzyloxydiethylaminophosphine (200 mg) and tetrazole (100 mg). The reaction was stirred for 2 hours and then treated with a further 100 mg of dibenzyloxydiethyl aminophosphine followed after 1 hour by tetrazole (100 mg). The reaction was stirred for a further 1 hour before adding 4-methylmorpholine-N-oxide (1.0 g) and stirring for 16 hours. The reaction was poured into potassium carbonate solution and extracted into ethyl acetate. The organic layer was dried (MgSO$_4$), filtered, evaporated and purified by chromatography on silica gel using methanol/dichloromethane (4:96) as eluent to yield an oil. This was dissolved in methanol (2 ml) and ammonium formate (100 mg) and palladium hydroxide (20% on carbon) was added. The reaction mixture was heated to reflux for one hour and then filtered, evaporated and freeze dried from acetonitrile/water to give the ammonium salt of the title compound (93 mg); $^1$H NMR (360 MHz, D$_6$-DMSO) δ 11.29 (1H, s), 7.85 (1H, s), 7.53 (2H, s), 7.36 (2H, m), 7.06 (2H, t, J=7.2 Hz), 4.96 (1H, t, J=5.4 Hz), 4.34 (1H, d, J=3.6 Hz), 4.29 (1H, t, J=11.2 Hz), 3.92–3.85 (1H, m), 3.68–3.63 (1H, m), 3.62–3.55 (1H, m), 3.49 (1H, d, J=3.6 Hz), 3.38 (1H, d, J=14.4 Hz), 2.82–2.79 (1H, m), 2.77 (1H, d, J=14.4 Hz), 2.41–2.35 (1H, m); MS (ES$^+$) 631 (M+H.

EXAMPLE 94

2-(R) (1-(S)-(3,5-Bis(trifluoromethyl)phenyl)-2-phosphoryloxyethoxy)-3-(S)-(4-fluorophenyl)-4-(1,2,4-triazol-3-yl)methylmorpholine The ammonium salt of the title compound was prepared from the compound of Example 89 by the methodology of Example 93. $^1$H NMR (250 MHz, D$_6$-DMSO+0.1% TFA) δ 8.74 (1H, s), 7.95 (1H, s), 7.68 (2H, broad s), 7.54 (2H, s), 7.30 (2H, t, J=8.7 Hz), 5.16 (1H, dd, J=7 Hz and 5 Hz), 4.72 (1H, d, J=1 Hz), 4.66 (1H, d, J=1 Hz), 4.42 (1H, t, J=11 Hz), 3.95–4.27 (3H, m), 3.72 (1H, d, J=11 Hz) and 3.41–3.55 (1H, m).

EXAMPLE 95

4-(2,3-Dihydro-3-oxo-1,2,4-triazol-5-yl)-3-(S)-phenyl-2-(R)-(1-(S)-(3-(trifluoromethyl)pbenyl)-2-hydroxyethoxy)morpholine Prepared from the compound of Description 30 following the method illustrated in Example 88. MS (Cl$^+$) m/z 465 ((M+1)$^+$, 71%).

EXAMPLE 96

4-(2,3-Dihydro-3-oxo-1,2,4-triazol-5-yl)methyl-2-(R)-(1-(S)-(3-fluoro-5-(trifluoromethyl)phenyl)-2-hydroxyethoxy)-3-(S)-phenylmorpholine The compound of Description 27 (600 mg), N-carbomethoxy -2-chloroacetamidrazone (271 mg) and potassium carbonate (258 mg) were reacted in dimethylformamide according to the procedure illustrated in Example 88. This afforded the product as a white solid which was recrystallised from ether/hexane (220 mg, 30%). $^1$H NMR (360 MHz, DMSO-d$_6$) δ 2.38 (1H, m), 2.78 (1H, d, J=14.0 Hz), 2.84 (1H, s), 3.38–3.39 (2H, m), 3.45 (1H, d, J=14.0 Hz), 3.50 (1H, d, J=3.0 Hz), 3.56 (1H, d, J=11.0 Hz), 4.26 (1H, t, J=11.0 Hz), 4.34 (1H, d, J=3.0 Hz), 4.68 (1H, t, J=6.0 Hz), 4.85 (1H, t, J=6.0 Hz), 6.40 (1H, d, J=9.0 Hz), 6.96 (1H, s), 7.33 (3H, m), 7.36 (1H, d, J=9.0 Hz), 7.49 (2H, m). MS (Cl$^+$) m/z 483 (M+1, 20%).

EXAMPLE 97

4-(2,3-Dihydro-3-oxo-1,2,4-triazol-5-yl)methyl-2-(R)-(1-(S)-3-fluoro-5-(trifluoromethyl)phenyl)-2-phosphoryloxyethoxy)-3-(S)-phenylmorpholine The ammonium salt of the title compound was prepared from the compound of Example 96 using the methodology of Example 93. $^1$H NMR (360 MHz, DMSO-d$_6$) δ 11.29 (1H, s), 7.49–7.29 (5H, m), 7.38 (1H, d, J=10.8 Hz), 6.96 (1H, s), 6.45 (1H, d, J=10.8 Hz), 4.84 (1H, d, J=7.2 Hz), 4.34 (1H, d, J=3.6 Hz), 4.28 (1H, t, J=10.8 Hz), 3.80–3.76 (1H, m), 3.57 (1H, d, J=3.6 Hz), 3.57–3.49 (2H, m), 3.47 (1H, d, J=14.4 Hz), 2.83–2.76 (1H, m), 2.78 (1H, d, J=14.4 Hz), 2.46–2.36 (1H. m).

EXAMPLE 98

2-(R)-(1-(S)-(3,5-Bis(trifluoromethyl)phenyl)-2-hydroxyethoxy)-4-(2,3-dihydro-3-oxo-1,2,4-triazol-5-yl)methyl-3-(S)-phenylmorpholine The compound of Description 17 was reacted with N-carbomethoxy-2-chloroacetamidrazone (Description 23) and potassium carbonate according to the procedure illustrated in Example 88. This afforded the product as a white solid. $^1$H NMR (360 MHz, DMSO-d$_6$) δ 2.42 (1H, dt, J=12.0, 3.5 Hz), 2.76 (1H, d, J=14.0 Hz), 2.83 (1H, d, J=12.0 Hz), 3.39 (1H, d, J=14.0 Hz), 3.44–3.47 (1H, m), 3.50 (1H, d, J=3.0 Hz), 3.60 (2H, m), 4.22–4.28 (1H, m), 4.40 (1H, d, J=3.0 Hz), 4.77–4.83 (2H, m), 7.25–7.34 (3H, m), 7.41 (2H, s), 7.48–7.50 (2H, m), 7.82 (1H, s), 11.20 (1H, s), 11.25 (1H, s), MS (Cl) m/z 533 (M+1, 30%) 434 (20), 117 (100).

EXAMPLE 99

2(R)-(1-(S)-(3,5-Bis(trifluoromethyl)phenyl)-2-phosphoryloxyethoxy)-4-(2,3-dihydro-3-oxo-1,2,4-triazol-5-yl)methyl-3-(S)-phenylmorpholine The ammonium salt of the title compound was prepared from Example 98 by the method of Example 93. $^1$H NMR (360 MHz, d$_6$-DMSO) δ 11.26 (1H, s), 7.83 (1H, s), 7.48–7.24 (7H, m), 4.95 (1H, t, J=5.4), 4.39 (1H, d, J=3.6), 4.29 (1H, t, J=11.2), 3.92–3.89 (1H, m), 3.60–3.64 (1H, m), 3.55–3.59 (1H, m), 3.48 (1H, d, J=3.6), 3.42 (1H, d, J=14.4), 2.84–2.79 (1H, m), 2.78 (1H, d, J=14.4), 2.42 (1H, m). HPLC on Zorbax Z-Ph (250×4.6 mm i.d. 5 μM) column eluting with 40% acetonitrile in 25 mM KH$_2$PO$_4$ with 0.2% triethylamine (pH 3.0), flow rate 1 ml/min, UV detector 210 nM. Retention time 4.68 min.

EXAMPLE 100

3-(S)-Phenyl-4-(1,2,4-triazol-3-yl)-2-(R)-(1-(S)-3-(trifluoromethyl)phenyl)-2-hydroxyethoxy)morpholine Prepared as a hydrochloride salt from the compound of Description 30 following the method illustrated in Example 89. MS (ES$^+$) m/z 449 ((M+1)$^+$ 100%). Examples 101 and 102 in Table 2 were prepared in a similar manner to that described in Example 12, Method B, via the appropriate N-(4-azidobut-2-ynyl)morpholine and the appropriate amine.

TABLE 1

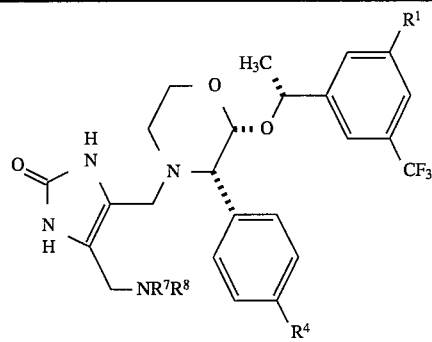

| Ex. No. | R$^1$ | R$^4$ | —NR$^7$R$^8$ | Data |
|---|---|---|---|---|
| 5 | CF$_3$ | F | —N(piperidinyl)—OH | MS (Cl$^+$) m/z 635 (M$^+$+H). Anal. Calcd. for C$_{30}$H$_{31}$F$_7$N$_4$O$_2$: C, 54.89; H, 5.24; N, 8.38. Found: C, 54.63; H, 5.32; N, 8.38%. |

TABLE 1-continued

| Ex. No. | R¹ | R⁴ | —NR⁷R⁸ | Data |
|---------|----|----|--------|------|
| 6 | F | F | —N(morpholine, O) | $^1$H NMR (250MHz, CDCl$_3$) δ 8.31 (1H, br s), 8.17(1H, br s), 7.37 (2H, br m), 7.04–7.11 (3H, m), 6.77 (1H, s), 6.33 (1H, d, J=9.0Hz), 4.75 (1H, m), 4.17–4.30 (2H, m), 3.58–3.69 (5H, m), 3.44 (1H, d, J=14.0Hz), 3.38 (1H, d, J=3.0Hz), 3.13 (2H, dd, J=19.91, 14.0Hz), 2.91 (1H, d, J=11.5Hz), 2.75 (1H, d, J=14.01Hz), 2.34 (5H, m), 1.41 (3H, d, J=6.5Hz). MS (Cl$^+$) m/z 583 |
| 7 | CF$_3$ | F | —N(morpholine, O) | $^1$H NMR (360MHz, DMSO) δ 9.71 (1H, s), 9.65 (1H, s), 7.85 (1H, s), 7.55 (2H, br s), 7.37 (2H, s), 7.07 (2H, t, J=8.85Hz), 4.91 (1H, m), 4.31 (1H, d, J=2.83Hz), 4.07 (1H, m), 3.61 (1H, br d, J=10.76Hz), 3.51 (4H, m), 3.36 (1H, d, J=2.70Hz), 3.27 (1H, d, J=10.34Hz), 3.08 (1H, d, J=13.6Hz), 2.93 (1H, d, J=13.6Hz), 2.86 (1H, d, J=11.51Hz), 2.61 (1H, d, J=13.6Hz), 2.27 (5H, m), 1.35 (3H, d, J= 6.55Hz). MS (Cl$^+$) m/z = 633. |
| 8 | CF$_3$ | F | —N(azetidine) | $^1$H NMR (250MHz, CDCl$_3$) δ 9.16 (1H, br s), 8.14 (1H, br s), 7.64 (1H, s), 7.38 (2H, br s), 7.09 (4H, m), 4.86 (1H, m), 4.22 (2H, m), 3.64 (1H, d, J=9.34Hz), 3.38 (2H, m), 3.16 (6H, m), 2.93 (1H, d, J=11.28Hz), 2.75 (1H, d, J=11.3Hz), 2.36 (1H, m), 2.05 (2H, m), 1.45 (3H, d, J=6.59Hz). MS (Cl$^+$) m/z 603. |
| 9 | CF$_3$ | F | —N(piperazine)N—CH$_3$ | $^1$H NMR (250MHz, CDCl$_3$) δ 8.03 (1H, s), 8.00 (1H, s), 7.63 (1H, s), 7.38 (2H, m), 7.06 (4H, m), 4.86 (1H, m), 4.28 (1H, d, J=2.8Hz), 4.19 (1H, d, J=11.47Hz), 3.64 (1H, d, J=9.41Hz), 3.38 (2H, m), 3.13 (2H, dd, J=13.61, 17.28Hz), 2.92 (1H, d, J=11.5Hz), 2.73 (1H, d, J=11.5Hz), 2.28–2.40 (12H, m), 1.45 (3H, d, J= 6.6Hz). MS (Cl$^+$) m/z 646 |
| 10 | CF$_3$ | F | —NH—(CH$_2$)$_2$—N(morpholine, O) | $^1$H NMR (250MHz, DMSO) δ 10.52 (1/2H, s), 9.87 (1/2H, s), 9.80 (1/2H, s), 9.66 (1/2H, s), 8.32 (1H, s), 7.86 (1H, s), 7.53 (2H, br s), 7.37 (2H, br s), 7.09 (2H, m), 4.93 (1H, m), 4.32 (1H, d, J=2.76Hz), 4.02 (2H, m), 3.62 (1H, d, J=11.78Hz), 3.52 (5H, m), 3.26 (2H, m), 2.86 (1H, m), 2.59 (1H, m), 2.31 (6H, m), 1.97 (3H, d, J=7.37Hz), 1.36 (3H, d, J=6.24Hz). MS (Cl$^+$) m/z 676 |
| 11 | CF$_3$ | F | —NH—(CH$_2$)$_2$—N(pyrrolidine) | $^1$H NMR (250MHz, CDCl$_3$) δ 7.63 (1H, s), 7.39 (2H, br s), 7.12 (2H, s), 7.04 (2H, m), 4.86 (1H, m), 4.28 (1H, d, J=2.7Hz), 4.18 (1H, m), 4.10 (1H, s), 3.67 (1H, s), 3.60 (1H, m), 3.39 (2H, m), 2.36–2.92 (10H, m), 2.07 (1H, s), 1.95 (4H, m), 1.45 (3H, d, J=6.53Hz). |
| 38 | CF$_3$ | F | —N(thiomorpholine, S) | $^1$H NMR (250MHz, CDCl$_3$) δ 9.35 (1H, s), 8.94 (1H, s), 7.78 (1H, s), 7.71 (2H, br m), 7.13 (2H, s), 7.06 (2H, t, J=8.7Hz), 4.86 (1H, q, J=6.4Hz), 4.30 (1H, d, J=2.8Hz), 4.24 (1H, m), 3.64 (1H, d, J=9.6Hz), 3.43 (1H, d, J=14Hz), 3.37 (1H, d, J=2.8Hz), 3.20 (1H, d, J=14Hz), 3.10 (1H, d, J=14Hz), 2.95 (1H, d, J= 11.3Hz), 2.75 (1H, d, J=14Hz), 2.62 (8H, s), 2.35 (1H, m), 1.49 (3H, d, J=6.4Hz). MS m/z 647 (MH$^+$). |
| 39 | F | F | —N(azetidine) | $^1$H NMR (250MHz, CDCl$_3$) δ 10.06 (1H, s), 8.85 (1H, s), 7.40 (2H, br s), 7.08 (3H, t, J=8.7Hz), 6.77 (1H, s), 6.33 (1H, d, J=8.7Hz), 4.75 (1H, q, J=6.4Hz), 4.29 (1H, d, J=2.8Hz), 4.22 (1H, m), 3.62 (1H, d, J=9.8Hz), 3.49 (1H, d, J= 14Hz), 3.38 (1H, d, J=2.8Hz), 3.16 (5H, m), 2.96 (1H, d, J=11.4Hz), 2.81 (1H, d, J=14Hz), 2.40 (1H, m), 2.05 (2H, m), 1.40 (3H, d, J=6.4Hz). MS m/z 553 (MH$^+$). |
| 40 | F | F | —N(CH$_3$)$_2$ | $^1$H NMR (250MHz, CDCl$_3$) δ 1.41 (3H, d, J=6.6Hz), 2.20 (6H, s), 2.34 (1H, m), 2.75 (1H, d, J=14.1Hz), 2.92 (1H, d, J=11.4Hz), 3.09 (2H, m), 3.37 (1H, d, J=2.8Hz), 3.44 (1H, d, J=14.1Hz), 3.62 (1H, m), 4.22–4.29 (2H, m), 4.75 (1H, m), 6.33 (1H, d, J=9.0Hz), 6.77 (1H, s), 7.08 (3H, m), 7.37 (2H, br s), 8.18 (1H, s), 8.92 (1H, s). MS (ES$^+$) m/z 540. |

TABLE 1-continued

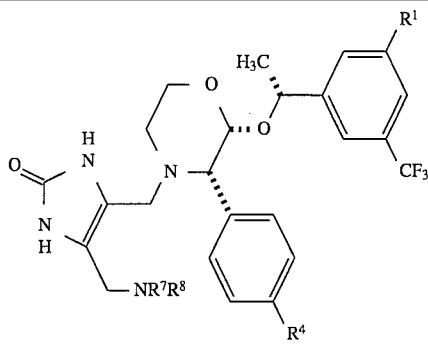

| Ex. No. | R[1] | R[4] | —NR[7]R[8] | Data |
|---|---|---|---|---|
| 41 | F | F | —N(pyrrolidinyl) | $^1$H NMR (360MHz, CDCl$_3$) δ 7.36 (2H, br s), 7.07 (3H, t, J=8.5Hz), 6.77 (1H, s), 6.33 (1H, d, J=8.5Hz), 4.76 (1H, q, J=6.4Hz), 4.28 (1H, d, J=2.7Hz), 4.22 (1H, m), 3.62 (1H, d, J=9.8Hz), 3.49 (1H, d, J=14Hz), 3.37 (1H, d, J=2.8Hz), 3.28 (2H, s), 2.91 (1H, d, J=7.9Hz), 2.75 (1H, d, J=9.7Hz), 2.45 (4H, m), 2.33 (1H, m), 1.74 (4H, m), 1.41 (3H, d, J=6.4Hz). |

TABLE 2

| Ex. No. | R[1] | R[4] | —NR[7]R[8] | Data |
|---|---|---|---|---|
| 14 | CF$_3$ | F | —NHCH$_3$ | HRMS (EI[+]) (found M[+], 561.1975. C$_{25}$H$_{26}$F$_7$N$_5$O$_2$ requires M[+], 561.1975). Analysis Calcd. for C$_{25}$H$_{26}$F$_7$N$_5$O$_2$.0.5H$_2$O: C, 52.54; H, 4.94; N. 12.25; Found: C, 52.67; H, 4.64; N, 12.08%. |
| 15 | CF$_3$ | F | —NH$_2$ | MS m/z (Cl[+]) 548 (M+H). |
| 16 | CF$_3$ | F | —N(pyrrolidinyl) | Analysis Calcd. for C$_{28}$H$_{30}$F$_7$N$_5$O$_2$: C, 55.90; H, 5.03; N, 11.64; Found: C, 55.71; H, 4.86; N. 11.53%. MS m/z (Cl[+]) 602 (M+H). |
| 17 | F | F | —N(azetidinyl) | $^1$H NMR (360MHz, CDCl$_3$) δ 1.40 (3H, d, J=6.6), 2.13 (2H, qn, J=7.1), 2.55 (2H, dt, J=12.0, 3.4), 2.88 (1H, d, J=11.7), 3.22–3.45 (5H, m), 3.57–3.66 (4H, m), 3.80 (1H, d, J=14.0), 4.20 (1H, dt, J=11.6. 2.1), 4.32 (1H, d, J=2.9), 4.76 (1H, q, 6.5), 6.39 (1H, d, J=8.9), 6.80 (1H, s), 7.05–7.12 (3H, m), 7.48 (2H, br s). MS (Cl[+]) m/z 538 (M+1, 100%). |
| 18 | F | F | —N(pyrrolidinyl) | $^1$H NMR (360MHz, CDCl$_3$) δ 1.40 (3H, d, J=6.6), 1.81 (4H, br s), 2.53–2.61 (5H, m), 2.89 (1H, d, J=11.7), 3.27 (1H, d, J=14.0), 3.45 (1H, d, J=2.8), 2.59–3.63 (1H, m), 3.63 (1H, d, J=13.7), 3.73 (1H, d, J=13.7), 3.83 (1H, d, J=14.0), 4.21 (1H, dt, J=11.6, 2.1), 4.32 (1H, d, J=2.8), 4.76 (1H, q, J=6.5), 6.37 (1H, d, J=9.1), 6.80 (1H, s), 7.05–7.10 (3H, m), 7.46 (2H, br s). MS (Cl[+]) 552 (M+1, 100%). |
| 19 | F | F | —N(morpholinyl) | $^1$H NMR (360MHz, CDCl$_3$) δ 1.40 (3H, d, J=6.6), 2.4–2.5 (4H, m), 2.56 (1H, dt, J=11.9, 3.4), 2.90 (1H, d, J=11.6), 3.30 (1H, d, J=14.1), 3.48–3.52 (2H, m), 3.58–3.71 (6H, m), 3.85 (1H, d, J=14.2), 4.23 (1H, dt, J=11.6, 2.3), 4.33 (1H, d, J=2.8), 4.77 (1H, q, J=6.5), 6.37 (1H, d, J=8.8), 6.80 (1H, s), 7.05–7.10 (3H, m), 7.46 (2H, br s), MS (Cl[+]) m/z 568 (M+1, 100%). |
| 20 | H | F | —N(CH$_3$)$_2$ | $^1$H NMR (250MHz, CDCl$_3$) δ 1.40 (3H, d, J=6.5), 2.25 (6H, s), 2.55 (1H, dt, J=11.8, 3.4), 2.91 (1H, d, J=11.6), 3.23 (1H, d, J=13.9), 3.41–3.64 (4H, m), 3.80 (1H, d, J=13.9), 4.24 (1H, t, J=11.5), 4.33 (1H, d, J=2.7), 4.77 (1H, q, J=6.5), 6.80 (1H, d, J=7.7), 6.95 (1H, s), 7.06 (2H, t, J=8.7), 7.16 (1H, t, J=7.7), 7.36 (1H, d, |

TABLE 2-continued

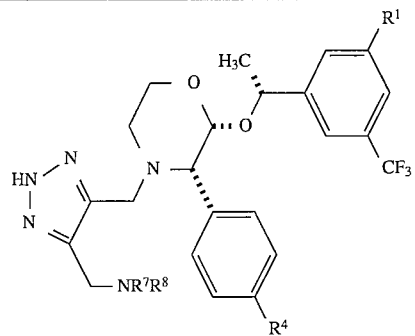

| Ex. No. | R¹ | R⁴ | —NR⁷R⁸ | Data |
|---|---|---|---|---|
| | | | | J=7.8), 7.48 (2H, br s),9.3–9.9(1H,br s). MS (Cl⁺) 508 (M+1, 100%). |
| 21 | CF₃ | F | —N⌒N—CH₃ | ¹H NMR (250MHz, CDCl₃) δ 7.63 (1H, s), 7.48 (2H, br s), 7.15 (2H, s), 7.05 (2H, t, J=8.7Hz), 4.86 (1H, q, J=6.6Hz), 4.30 (1H, d, J=2.7Hz), 4.21 (1H, br t, J=11.4Hz), 3.77 (1H, d, J=13.9Hz), 3.67 (1H, d, J=14.0Hz), 3.65 (1H, m), 3.56 (1H, d, J=14.0Hz), 3.43 (1H, d, J=2.7Hz), 3.20 (1H, d, J=13.9Hz), 2.85 (1H, d, J=11.5Hz), 2.56–2.48 (9H, m), 2.31 (3H, s), 1.42 (3H, d, J=6.6Hz). |
| 25 | CF₃ | F | —N▱ (azetidine) | ¹H NMR (360MHz, CDCl₃) δ 1.44 (3H, d, J=6.6Hz), 2.14 (2H, m), 2.55 (1H, dd, J=3.4, 11.9Hz), 2.87 (1H, d, J=11.9Hz), 3.21–3.44 (6H, m), 3.58–3.67 (3H, m), 3.75 (1H, d, J=14.0Hz), 4.2 (1H, t, J=9.3Hz), 4.31 (1H, d, J=2.8Hz), 4.85 (1H, m), .06 (2H, t, J=8.7Hz), 7.16 (1H, m), 7.47 (2H, br s), 7.63 (1H, s). |
| 26 | CF₃ | F | —N▱ (dihydropyrrole) | ¹H NMR (250MHz, CDCl₃) δ 1.44 (3H, J=6.7Hz), 2.57 (1H, dd, J=3.4, 11.9Hz), 2.90 (1H, d, J=11.6Hz), 3.23 (1H, d, J=3.9Hz), 3.45–3.66 (6H, m), 3.75–3.84 (3H, m), 4.08–4.26 (1H, m), 4.31 (1H, d, J=2.8Hz), 4.86 (1H, m), 5.78 (2H, s), 7.05 (2H, t, J=8.7Hz), 7.15 (2H, s), 7.47 (2H, brt), 7.64 (1H, s). |
| 27 | CF₃ | F | —N(CH₂CH₂OCH₃)₂ | ¹H NMR (250MHz, CDCl₃) δ 1.44 (3H, d, J=6.58Hz), 2.73 (5H, m), 2.95 (1H, d, J=11.8Hz), 3.23 (1H, d, J=13.9Hz), 3.37 (6H, s), 3.41–3.49 (5H, m), 3.63–3.86 (4H, m), 4.18 (1H, t, J=11.5Hz), 4.30 (1H, d, J=2.8Hz), 4.84 (1H, m), 7.06 (2H, t, J=8.7Hz), 7.14 (2H, s), 7.45 (2H, br t), 7.63 (1H, s). MS (ES⁺) m/z 664 (MH⁺, 100%). |
| 31 | CF₃ | H | —N(CH₃)CH₂CH(OCH₃)₂ | ¹H NMR (250MHz, CDCl₃) δ 1.43 (3H, d, J=6.5Hz), 2.17 (3H, s), 2.53 (2H, d, J=5.0Hz), 2.60–2.73 (1H, br dt), 2.95 (1H, br d), 3.30 (3H, s), 3.32 (3H, s), 3.31 (1H, d, J=14.0Hz), 3.44 (1H, d, J=2.7Hz), 3.56 (1H, d, J=2.0Hz), 3.64 (1H, br d), 3.82 (1H, d, J=14.0Hz), 4.20–4.29 (1H, br t), 4.36 (1H, d, J=2.7Hz), 4.47 (1H, t, J=5.0Hz), 4.85 (1H, q, J=6.5Hz), 7.14 (2H, s), 7.27–7.38 (3H, m), 7.45 (2H, br s), 7.61 (1H, s), MS (ES) m/z 632 (M++1, 100%) |
| 32 | CF₃ | H | —NH(CH₂)₂OCH₃ | ¹H NMR (250MHz, CDCl₃) δ 1.45 (3H, d, J=6.5Hz), 2.50 (1H, dt, J=3.4, 12.0Hz), 2.79–2.87 (3H, m), 3.16 (1H, d, J=14.0Hz), 3.35 (3H, s), 3.41 (1H, d, J=2.7Hz), 3.51–3.67 (3H, m) 3.75–3.87 (3H, m), 4.24 (1H, br t), 4.36 (1H, d, J=2.7Hz), 4.87 (1H, q, J=6.5Hz), 7.16 (2H, s), 7.33–7.39 (3H, m), 7.46 (2H, m), 7.61 (1H, s). MS (ES) m/z 588 (M⁺+1, 100%). |
| 33 | CF₃ | H | —N(CH₃)(CH₂)₂OCH₃ | ¹H NMR (250MHz, CDCl₃) δ 1.43 (3H, d, J=6.5Hz), 2.24 (3H, s), 2.58 (2H, t, J=3.5Hz), 2.65 (1H, br t), 2.94 (1H, br d), 3.29 (1H, d, J=9.5Hz), 3.36 (3H, s), 3.43 (1H, d, J=2.0Hz), 3.49 (2H, t, J=3.5Hz), 3.56 (1H, d, J=3.5Hz), 3.63 (1H, dd, J=1.3, 7.75Hz), 3.80 (1H, d, J=9.5Hz), 4.23 (1H, dt, J=1.5, 8.0Hz), 4.36 (1H, d, J=2.0Hz), 4.84 (1H, q, J=6.5Hz), 7.15 (2H, s), 7.32–7.36 (3H, m), 7.45 (2H, m), 7.61 (1H, s). MS (ES) m/z 602 (M⁺+1, 100%). |
| 34 | CF₃ | H | —N[CH(CH₃)₂](CH₂)₂OCH₃ | ¹H NMR (250MHz, CDCl₃) δ 0.99 (3H, d, J=6.5Hz), 1.02 (3H, d, J=6.5Hz), 1.43 (3H, d J=6.5Hz), 2.64–2.71 (3H, m), 2.91–2.98 (2H, m), 3.26(1H, d, J=14.0Hz), 3.39 (6H, s), 3.43 (1H, d, J=2.6Hz), 3.49–3.81 (3H, m), 4.22 (1H, dt, J=2.0, 11.5Hz), 4.35 (1H, d, J=2.6Hz), 4.86 (1H, q, J=6.5Hz), 7.14 (2H, s), 7.31–7.35 (3H, m), 7.45 (2H, m), 7.61 (1H, s). MS (ES) m/z 630 (M⁺+1, 100%). |
| 35 | CF₃ | H | —N(cyclopropyl)(CH₂)₂OCH₃ | ¹H NMR (250MHz, CDCl₃) δ 0.29–0.42 (4H, m), 1.43 (3H, d, J=6.5Hz), 1.63 (1H, br qn), 2.72 (2H, t, J=5.0Hz), 2.7–2.74 (1H, m), 3.02–3.07 (1H, m), 3.27–3.37 (1H, m), 3.37 (3H, s), 3.43 (1H, d, J=2.8Hz), 3.55 (2H, t, J=5.0Hz), 3.62–3.70 (3H, m), 3.82 (1H, d, J=14.0Hz), 4.25 (1H, br t), 4.34 (1H, d, J=2.8Hz), 4.84 (1H, q, J=6.5Hz), 7.13 (2H, s), 7.33–7.36 (3H, m), 7.43 (2H, m), 7.61 (1H, s). MS (ES) m/z 628 (M⁺+1, 100%). |
| 36 | CF₃ | H | —N(CH₂CH₂CH₃)₂ | ¹H NMR (250MHz, CDCl₃) δ 0.85 (6H, t, J=7.25Hz), 1.14–1.38 (9H, m), 1.44 (3H, d, J=6.5Hz), 2.34 (4H, br t), 2.63–2.73 (2H, m), 2.97 (1H, m), 3.34 (1H, d, J=14.0Hz), 3.41–3.47 (3H, m), 3.64 (1H, dd, J=2.0, 11.0Hz), 3.79 (1H, d, J=14.0Hz), 4.26 (1H, br t), 4.35 (1H, d, J=2.8Hz), 4.84 (1H, q, J=6.5Hz), 7.14 (2H, s), 7.32–7.35 (3H, m), 7.43 (2H, m), 7.61 (1H, s). |
| 37 | CF₃ | H | —N[CH(CH₃)₂]₂ | ¹H NMR (250MHz, CDCl₃) δ 1.01 (12H, d, J=7.25Hz), 1.43 (3H, d, J=6.5Hz), 2.68 (1H, dt, J=3.5, 12.5Hz), 2.92–3.02 (3H, m), 3.32 (1H, d, J=14.0Hz), 3.44 (1H, |

TABLE 2-continued

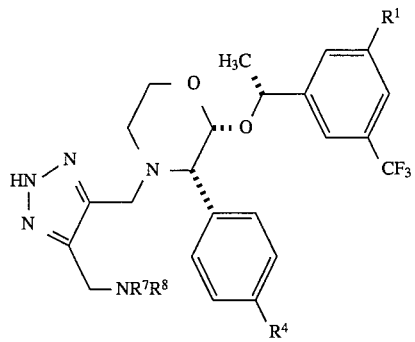

| Ex. No. | R¹ | R⁴ | —NR⁷R⁸ | Data |
|---|---|---|---|---|
| | | | | d, J=2.8Hz), 3.48 (1H, br d), 3.52–3.72 (2H, m), 3.77 (1H, d, J=14.0Hz), 4.24 (1H, br t), 4.36 (1H, d, J=2.8Hz), 4.85 (1H, q, J=6.5Hz), 7.14 (2H, s), 7.32–7.35 (3H, m), 7.45 (2H, m), 7.61 (1H, s). |
| 43 | $CF_3$ | F | pyrrolidine-2-yl-CH₂OCH₃ | $^1$H NMR (250MHz, CDCl₃) δ 1.44 (3H, d, J=6.6Hz), 1.52–1.92 (4H, m), 2.26 (1H, m), 2.61–2.77 (2H, m), 2.93 (2H, m), 3.26 (2H, d, J=14.0Hz), 3.36 (5H, m), 3.61–3.89 (4H, m), 4.23 (1H, m), 4.30 (1H, d, J=2.8Hz), 4.86 (1H, m), 7.06 (2H, t, J=8.8Hz), 7.15 (2H, s), 7.46 (2H, br s), 7.63 (1H, s). MS (ES⁺) m/z 645. |
| 44 | $CF_3$ | F | —N[CH(CH₃)₂]₂ | $^1$H NMR (250MHz, CDCl₃) δ 1.30 (6H, d, J=6.5Hz), 1.31 (6H, d, J=6.5Hz), 1.75 (3H, d, J=6.6Hz), 2.95 (1H, m), 3.20–3.31 (3H, m), 3.57 (1H, d, J=14.1Hz), 3.78 (2H, m), 3.92–4.05 (3H, m), 4.53 (1H, m), 4.62 (1H, d, J=2.80Hz), 5.17 (1H, m), 7.35 (2H, t, J=8.7Hz), 7.46 (2H, s), 7.76 (2H, m), 7.94 (1H, s). MS (ES⁺) m/z 631. |
| 45 | $CF_3$ | F | —N(CH₂CH₂CH₃)CH₂CH₂OH | $^1$H NMR (250MHz, CDCl₃) δ 7.64 (1H, s), 7.49 (2H, br s), 7.17 (2H, s), 7.06 (2H, t, J=8.7Hz), 4.86 (1H, q, J=6.5Hz), 4.31 (1H, d, J=2.7Hz), 4.26 (1H, t, J=9.6Hz), 3.74 (1H, d, J=13.7Hz), 3.60 (5H, m), 3.44 (1H, d, J=2.7Hz), 3.15 (1H, d, J=13.7Hz), 2.96 (1H, d, J=11.7Hz), 2.68–2.49 (5H, m), 1.56–1.42 (5H, m), 0.87 (3H, t, J=7.3Hz). MS m/z 634 (MH⁺). |
| 46 | $CF_3$ | F | pyrrolidine-2-yl-CH₂OH | $^1$H NMR (250MHz, CDCl₃) δ 7.63 (1H, s), 7.57 (2H, br s), 7.15 (2H, s), 7.06 (2H, t, J=8.7Hz), 4.86 (1H, q, J=6.5Hz), 4.30 (2H, m), 3.82 (2H, m), 3.64 (2H, d, J=13.5Hz), 3.44 (1H, d, J=2.6Hz), 3.32 (2H, m), 3.15–3.03 (3H, m), 2.88 (1H, m), 2.66–2.47 (2H, m), 1.87 (1H, m), 1.81–1.64 (3H, m), 1.43 (3H, d, J=6.5Hz). MS m/z 632 (MH⁺). |
| 47 | $CF_3$ | F | pyrrolidine-2-yl-CH₂OH (epimer) | $^1$H NMR (250MHz, CDCl₃) δ 7.63 (1H, s), 7.57 (2H, br s), 7.15 (2H, s), 7.06 (2H, t, J=8.7Hz), 4.86 (1H, q, J=6.5Hz), 4.32 (1H, d, J=2.7Hz), 4.22 (1H, m), 3.88 (1H, d, J=14.1Hz), 3.74 (1H, d, J=14.0Hz), 3.64–3.54 (3H, m), 3.44 (2H, m), 3.20 (1H, d, J=14Hz), 3.00–2.81 (3H, m), 2.55 (1H, m), 2.34 (1H, m), 1.92 (1H, m), 1.71 (3H, m), 1.44 (3H, d, J=6.5Hz). MS m/z 632 (MH⁺). |
| 48 | $CF_3$ | F | —N[CH(CH₃)₂]CH₂CH₂OH | $^1$H NMR (250MHz, CDCl₃) δ 7.64 (1H, s), 7.49 (2H, br s), 7.27 (2H, s), 7.06 (2H, t, J=8.7Hz), 4.86 (1H, q, J=6.5Hz), 4.31 (1H, d, J=2.7Hz), 4.14 (1H, m), 3.76–3.43 (7H, m), 3.17 (1H, d, J=13.8Hz), 3.04–2.89 (2H, m), 2.75–2.53 (3H, m), 1.43 (3H, d, J=6.5Hz), 1.5 (6H, d, J=6.6Hz). M/S m/z 634 (MH⁺). |
| 49 | $CF_3$ | F | —N(CH₃)C(CH₃)₃ | $^1$H NMR (250MHz, CDCl₃) δ 7.63 (1H, s), 7.45 (2H, br s), 7.15 (2H, s), 7.05 (2H, t, J=8.74Hz), 4.87 (1H, q, J=6.58Hz), 4.31 (1H, d, J=2.79Hz), 4.23 (1H, m), 3.75 (1H, d, J=14.16Hz), 3.64 (1H, m), 3.54 (1H, d, J=14.40Hz), 3.48 (1H, d, J=14.40Hz), 3.46 (1H, d, J=2.79Hz), 3.32 (1H, d, J=14.16Hz), 2.94 (1H, d, J=11.73Hz), 2.65 (1H, td, J=10.33, 3.51Hz), 2.09 (3H, s), 1.45 (3H, d, J=6.58Hz), 1.15 (9H, s). M/S (ES⁺) 618. |
| 50 | $CF_3$ | F | 2,5-dimethylpyrrolidino | MS (ES⁺) m/z 629 (MH⁺, 100%) |
| 51 | $CF_3$ | F | —N(CH₂CH₃)₂ | $^1$H NMR (250MHz, CDCl₃) δ 1.00 (6H, t, J=7.2Hz), 1.44 (3H, d, J=6.6Hz), 2.46–2.55 (4H, m), 2.62 (1H, m), 2.91 (1H, d, J=11.7Hz), 3.27 (1H, d, J=14.0Hz), 3.46 (1H, d, J=2.7Hz), 3.56 (2H, s), 3.62 (1H, m), 3.77 (1H, d, J=14.1Hz), 4.24 (1H, m), 4.31 (1H, d, J=2.8Hz), 4.86 (1H, m), 7.05 (2H, t, J=8.7Hz), 7.15 (2H, s), 7.47 (2H, br s), 7.64 (1H, s). MS (ES⁺) m/z 603 |
| 52 | $CF_3$ | H | —N(CH₃)₂ | Analysis Calcd. for $C_{26}H_{29}N_5O_2F_6 \cdot HCl \cdot H_2O$: C, 51.03; H, 5.27; N, 11.44. Found C, 51.21; H, 5.24; N, 11.10%. M.pt. 127–129° C. |

TABLE 2-continued

| Ex. No. | R¹ | R⁴ | —NR⁷R⁸ | Data |
|---|---|---|---|---|
| 53 | CF₃ | H | —N(CH₂CH₃)₂ | ¹H NMR (250MHz, CDCl₃) δ 1.03 (6H, t, J=7.1Hz), 1.44 (3H, d, J=6.6Hz), 2.51–2.70 (5H, m), 2.93 (1H, d, J=11.6Hz), 3.32 (1H, d,J= 14.1Hz), 3.44 (1H, d, J=2.7Hz), 3.57–3.66 (3H, m), 3.80 (1H, d, J=14.1Hz), 4.24 (1H, m), 4.35 (1H, d, J=2.7Hz), 4.85 (1H, m), 7.14 (2H, s), 7.27 (1H, s), 7.34 (3H, m), 7.45 (2H, br s), 7.61 (1H, s). MS (ES⁺) m/z 585. |
| 54 | CF₃ | H | —N(CH₂CH₂CH₃)₂ | ¹H NMR (250MHz, CDCl₃) δ 0.82 (6H, t, J=7.4Hz), 1.35–1.46 (7H, m), 2.36 (4H, m), 2.66 (1H, m), 2.95 (1H, d, J=11.6Hz), 3.35 (1H, d, J= 14.2Hz), 3.44 (1H, d, J=2.78Hz), 3.53 (2H, s), 3.64 (1H, m), 3.78 (1H, d, J= 14.3Hz), 4.26 (1H, m), 4.35 (1H, d, J=2.8Hz), 4.85 (1H, m), 7.14 (2H, s), 7.33 (3H, m), 7.43 (2H, br s), 7.61 (1H, s). MS (ES⁺) m/z 613. |
| 55 | CF₃ | H | piperidinyl | ¹H NMR (250MHz, CDCl₃) δ 1.44–1.56 (9H, m), 2.35 (4H, m), 2.61 (1H, m), 2.92 (1H, d, J=11.7Hz), 3.29 (1H, d, J=14.0Hz), 3.40–3.56 (3H, m), 3.83 (1H, d, J=14.0Hz), 4.24 (1H, m), 4.36 (1H, d, J=2.8Hz), 4.86 (1H, m), 7.15 (2H, s), 7.34 (3H, m), 7.47 (2H, br s), 7.61 (1H, s). MS (ES⁺) m/z 597. |
| 56 | CF₃ | H | 2-(methoxymethyl)pyrrolidinyl | ¹H NMR (250MHz, CDCl₃) δ 1.44 (3H, d, J=6.6Hz), 1.52–1.91 (4H, m), 2.28 (1H, m), 2.66–2.75 (2H, m), 2.93 (2H, m), 3.28–3.43 (7H, m), 3.62 (2H, m), 3.80 (2H, d, J=14.2Hz), 4.22 (1H, m), 4.35 (1H, d, J=2.7Hz), 4.85 (1H, m), 7.14 (2H, s), 7.33 (3H, m), 7.44 (2H, br s), 7.61 (1H, s). MS (ES⁺) m/z 627. |
| 57 | F | F | —N(CH₃)₂ | ¹H NMR (360MHz, CDCl₃) δ 1.40 (3H, d, J=6.5Hz), 2.24 (6H, s), 2.57 (1H, m), 2.89 (1H, d, J=11.8Hz), 3.27 (1H, d, J=14.0Hz), 3.46 (2H, s), 3.52–3.63 (2H, m), 3.82 (1H, d, J=14.1), 4.22 (1H, t, J=10.4Hz), 4.76 (1H, m), 6.37 (1H, d, J=8.9Hz), 6.80 (1H, s), 7.05–7.10 (3H, m), 7.46 (2H, br s). |
| 58 | F | F | —N(CH₂CH₃)₂ | ¹H NMR (360MHz, CDCl₃) δ 1.01 (6H, t, J=7.1Hz), 1.39 (3H, d, J=6.6Hz), 2.48–2.63 (5H, m), 2.91 (1H, d, J=11.8Hz), 3.30 (1H, d, J=14.1Hz), 3.46 (1H, d, J=2.8Hz), 3.57 (2H, s), 3.60–3.63 (1H, m), 3.81 (1H, d, J=14.1Hz), 4.20–4.26 (1H, m), 4.32 (1H, d, J=2.8Hz), 4.76 (1H, m), 6.36 (1H, d, J=8.9Hz), 6.80 (1H, s), 7.04–7.09 (3H, m), 7.46 (2H, br s). |
| 59 | | | 2-(methoxymethyl)pyrrolidinyl | ¹H NMR (250MHz, CDCl₃) δ 7.44 (2H, br s), 7.37 (3H, t, J=3.28Hz), 7.03 (1H, d, J=8.27Hz), 6.81 (1H, s), 6.23 (1H, d, J=9.32Hz), 4.76 (1H, q, J=6.57Hz), 4.34 (1H, d, J=2.80Hz), 4.22 (1H, m), 3.87–3.59 (4H, m), 3.43–3.32 (8H, m), 2.94 (2H, m), 2.72 (2H, m), 2.29 (2H, q, J=8.54Hz), 1.92–1.53 (4H, m), 1.39 (3H, d, J=6.59Hz). |
| 60 | | | —N[CH(CH₃)₂]₂ | ¹H NMR (250MHz, CDCl₃) δ 7.45 (2H, br s), 7.37 (3H, t, J=2.99Hz), 7.03 (1H, d, J=8.29Hz), 6.82 (1H, s), 6.23 (1H, d, J=9.08Hz), 4.76 (1H, q, J= 6.55Hz), 4.35 (1H, d, J=2.83Hz), 4.24 (1H, td, J=1.60Hz, 2.31Hz), 3.82 (1H, d, J=14.20Hz), 3.68 (1H, d, J=13.92Hz), 3.63 (1H, m), 3.50 (1H, d, J=13.92Hz), 3.46 (1H, m), 3.36 (1H, d, J=14.20Hz), 2.97 (3H, m), 2.68 (1H, td, J=12.01Hz, 3.47Hz), 1.39 (3H, d, J=6.55Hz). MS m/z (ES⁺) 564. |
| 61 | | | norbornyl-N | ¹H NMR (250MHz, CDCl₃) δ 7.42 (2H, br s), 7.36 (3H, t, J=3.01Hz), 7.03 (1H, d, J=8.29Hz), 6.81 (1H, s), 6.23 (1H, d, J=9.11Hz), 4.76 (1H, q, J=6.62Hz), 4.33 (1H, d, J=2.79Hz), 4.22 (1H, m), 3.85 (1H, d, J=14.06Hz), 3.62 (1H, m), 3.52 (2H, d, J=2.09Hz), 2.65 (1H, td, J=10.34Hz, 3.54Hz), 1.79 (4H, br m), 1.37 (8H, m). MS m/z (ES⁺) 560. |

TABLE 2-continued

| Ex. No. | R¹ | R⁴ | —NR⁷R⁸ | Data |
|---|---|---|---|---|
| 62 | | | (norbornyl-N) | $^1$H NMR (250MHz, CDCl$_3$) δ 7.61 (1H, s), 7.42 (2H, br s), 7.32 (3H, m), 7.13 (2H, s), 4.84 (1H, q, J=6.5Hz), 4.34 (1H, d, J=2.8Hz), 4.23 (1H, m), 3.81 (1H, d, J=14Hz), 3.63 (1H, dd, J=2.0, 11.2Hz), 3.48 (2H, s), 3.40 (1H, d, J=2.8Hz), 3.25 (1H, d, J=14Hz), 3.22 (2H, t, J=4.2Hz), 2.96 (1H, d, J=11.7Hz), 2.64 (1H, m), 1.76 (4H, m), 1.43 (3H, d, J=6.5Hz), 1.35 (4H, m). MS m/z 610 (MH⁺). |
| 101 | CF$_3$ | F | —N[CH(CH$_3$)$_2$]CH$_2$CH$_3$ | $^1$H NMR (250MHz, CDCl$_3$) δ 0.87–0.95 (9H, m), 1.36 (3H, d, J=6.6Hz), 2.36–2.44 (2H, m), 2.61 (1H, dt, J=12.0Hz, 3.5Hz), 2.83–2.91 (2H, m), 3.28 (1H, d, J=14.1Hz), 3.37–3.45 (3H, m), 3.57 (1H, m), 3.72 (1H, d, J=14.1Hz), 4.17 (1H, dt, J=11.7Hz, 2.4Hz), 4.29 (1H, d, J=2.8Hz), 4.78 (1H, q, J=6.6Hz), 7.07 (2H, s), 7.24–7.29 (3H, m), 7.37 (2H, vbr s), 7.54 (1H, s). MS (ES⁺) m/z 599 (MH⁺, 100%). |
| 102 | F | H | —N(CH$_3$)$_2$ | $^1$H NMR (360MHz, CDCl$_3$) δ 1.39 (3H, d, J=6.6Hz), 2.25 (6H, s), 2.60 (1H, dt, J=11.9, 3.5Hz), 2.91 (1H, d, J=11.5Hz), 3.31 (1H, d, J=14.0Hz), 3.41–3.63 (4H, m), 3.87 (1H, d, J=14.0Hz), 4.23 (1H, br t, J=11.6Hz), 4.35 (1H, d, J=2.8Hz), 4.76 (1H, q, J=6.5Hz), 6.27 (1H, d, J=9.2Hz), 6.83 (1H, s), 7.03 (1H, d, J=8.3Hz), 7.34–7.40 (4H, m), 7.47 (2H, br s). MS (ES⁺) m/z 508 (M+1, 100%). |

TABLE 3

| Ex. No. | R⁴ | —ZNR⁷R⁸ | Data |
|---|---|---|---|
| 64 | H | 2-(CH$_2$)$_2$—N(piperidinyl) | $^1$H NMR (360MHz, d$_6$-DMSO) δ 7.80 (2H, s), 7.54–7.48 (2H, m), 7.42 (2H, s), 7.36–7.28 (3H, m), 4.92–4.98 (1H, q, J=6.5Hz), 4.38 (1H, d, J=2.7Hz), 4.18–4.00 (3H, m), 3.70 (1H, d, J=14.0), 3.61 (1H, d, J=9.9Hz), 3.54 (1H, d, J=2.7Hz), 3.17 (1H, d, J=14.0Hz), 3.80–3.70 (1H, m), 2.58–2.50 (2H, m), 2.20–2.16 (4H, m), 1.37 (3H, d, J=6.5Hz), 1.32–1.28 (6H, m). M/S⁺ 612. |
| 65 | H | 1-(CH$_2$)$_2$—N(piperidinyl) | $^1$H NMR (360MHz, DMSO) δ 8.35 (1H, s), 7.82 (1H, s), 7.46–7.40 (2H, m), 7.36 (2H, s), 7.32–7.22 (3H, m), 4.89–4.93 (1H, (1H, q, J=6.5), 4.34 (1H, d, J=2.8), 4.19 (2H, t, J=6.2), 4.09 (1H, t, J=11.2), 3.60–3.52 (3H, m), 3.09 (1H, d, J=13.6), 2.93 (1H, d, J=11.7), 2.61 (2H, t, J=6.4), 2.50–2.38 (1H, m), 2.36–2.32 (4H, m), 1.44–1.40 (6H, m), 1.34 (3H, d, J=6.5). M/S+1 612. |
| 66 | H | 2-(CH$_2$)$_2$—N(CH$_2$CH$_2$CH$_3$)$_2$ | $^1$H NMR(360MHz, d$_6$-DMSO) δ 7.84(1H, s), 7.83(1H, s), 7.45–7.49 (2H, m), 7.42 (2H, s), 7.32–7.31 (3H, m), 4.92–4.98 (1H, q, J=6.5Hz), 4.38 (1H, d, J=2.7Hz), 4.07–4.11 (1H, m), 3.88–3.95 (2H, m), 3.68 (1H, d, J=14.2Hz), 3.61 (1H, d, J=11.4Hz), 3.53 (1H, d, J=2.7Hz), 3.20 (1H, d, J=14.2Hz), 2.80 (1H, d, J=11.4Hz), 2.65–2.49 (3H, s), 2.17 (4H, t, J=7.1Hz), 1.37 (3H, d, J=6.5Hz), 1.18–1.12 (4H, m), 0.67 (6H, t, J=7.2Hz). MS⁺ 628. |
| 67 | H | 5-CH$_2$—N(CH$_2$CH$_2$CH$_3$)$_2$ | $^1$H NMR (250MHz, CDCl$_3$) δ 7.61 (1H, s), 7.48–7.40 (2H, m), 7.38–7.30 (3H, m), 7.13 (2H, s), 4.88–4.83 (1H, q, J=6.5Hz), 4.36 (1H, d, J=2.8Hz), 4.30(1H, t, J=11.5Hz), 3.83 (1H, d, |

TABLE 3-continued

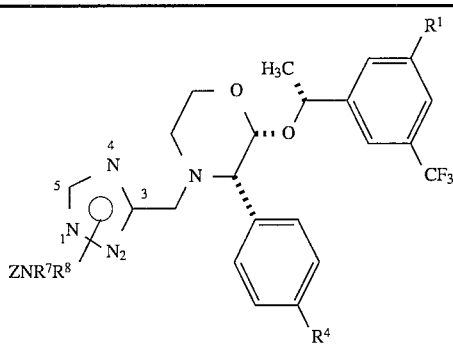

| Ex. No. | R⁴ | —ZNR⁷R⁸ | Data |
|---|---|---|---|
| 68 | H | 1-CH₂CH₂—N(CH₃)₂ | J=14.5Hz), 3.65–3.62 (1H, d, J=11.2Hz), 3.55 (1H, d, J=2.7Hz), 3.53 (1H, d, J=14.4Hz), 3.00 (1H, d, J=11.6Hz), 2.66–2.57 (1H, dxt, J=3.5 and 11.9Hz), 2.43 (4H, t, J=7.42Hz), 1.54–1.40 (9H, m), 0.87 (6H, t, J=7.3Hz). M/S ES⁺ 614. <br> ¹H NMR (250MHz,CDCl₃) δ 8.01 (1H, s), 7.53 (1H, s), 7.41–7.35 (2H, m), 7.29–7.19 (3H, m), 7.06 (2H, s), 4.79–4.75 (1H, q, J=6.5Hz), 4.29 (1H, d, J=2.80Hz), 4.29–4.19 (1H, m), 4.10 (2H, t, J=6.4Hz), 3.76 (1H, d, J=14.1Hz), 3.57–3.52 (2H, m), 3.26 (1H, d, J=14.1Hz), 2.92 (1H, d, J=11.8Hz), 2.63 (2H, t, J=6.3Hz), 2.52 (1H, dt, J=3.5 and 11.9Hz), 2.18 (6H, s), 1.36 (3H, d, J=6.6Hz). M/S ES⁺ 572. |
| 69 | F | 5-CH₂—N⟨piperidine⟩—OH | ¹H NMR (250MHz, CDCl₃) δ 7.34 (1H, s), 7.18–7.08 (2H, m), 6.85 (2H, s), 6.74 (2H, t, J=8.7Hz), 4.60–4.55 (1H, q, J=6.4Hz), 4.03 (1H, d, J=2.8Hz), 4.04–3.94 (1H, m), 3.48 (1H, d, J=14.8Hz), 3.50–3.34 (4H, m), 3.26 (1H, d, J=2.8Hz), 3.03 (1H, d, J=14.7Hz), 2.66 (1H, d, J=11.7Hz), 2.58–2.42 (2H, m), 2.31 (1H, dt, J=3.4 and 11.9Hz), 2.08–1.94 (2H, m), 1.64–1.54 (2H, m), 1.40–1.24 (2H, m), 1.17 (3H, d, J=6.6Hz). M/S ES⁺ 614. |
| 70 | H | 2-(CH₂)₂—N⟨piperidine⟩—OH | ¹H NMR (250MHz, CDCl₃) δ 7.80 (1H, s), 7.61 (1H, s), 7.58–7.42 (2H, m), 7.40–7.36 (3H, m), 7.15 (2H, s), 4.90–4.85 (1H, q, J=6.5Hz), 4.36 (1H, d, J=2.8Hz), 4.27–3.95 (3H, m), 3.82 (1H, d, J=14.0Hz), 3.64–3.60 (2H, m), 3.40 (1H, d, J=2.8Hz), 3.24 (1H, d, J=14.0Hz), 2.89 (1H, d, J=11.9Hz), 2.72–2.61 (5H, m), 2.09 (2H, t, J=9.5Hz), 1.80–1.62 (3H, m), 1.44 (3H, d, J=6.6Hz), 1.43–1.24 (2H, m). M/S ES⁺ 628. |
| 71 | H | 1-(CH₂)₂—N⟨piperidine⟩—OH | ¹H NMR (250MHz, CDCl₃) δ 8.11 (1H, s), 7.60 (1H, s), 7.50–7.44 (2H, m), 7.38–7.30 (3H, m), 7.13 (2H, s), 4.86–4.81 (1H, q, J=6.5Hz), 4.40–4.14 (4H, m), 3.83 (1H, d, J=14.2Hz), 3.78–3.60 (4H, m), 3.36 (1H, d, J=13.9Hz), 3.98 (1H, d, J=11.8Hz), 2.84–2.52 (5H, m), 2.34–2.18 (1H, m), 1.96–1.44 (5H, m), 1.44 (3H, d, J=6.5Hz). M/S ES⁺ 628. |
| 72 | F | 2-CH₂CH₂—N(CH₃)₂ | ¹H NMR (250MHz, CDCl₃) δ 7.80 (1H, s), 7.63 (1H, s), 7.52–7.42 (2H, m), 7.18 (2H, s), 7.07 (2H, t, J=8.7Hz), 4.91–4.86 (1H, q), 4.32 (1H, d, J=2.8Hz), 4.24–4.06 (3H, m), 3.76 (1H, d, J=14.0Hz), 3.64–3.60 (1H, m), 3.44 (1H, d, J=2.8Hz), 3.24 (1H, d, J=13.9Hz), 2.82–2.60 (4H, m), 2.25 (6H, s), 1.62–1.56 (6H, m), 1.46 (3H, d, J=6.6Hz). M/S ES⁺ 660. |
| 73 | F | 1-CH₂CH₂—N(CH₃)₂ | ¹H NMR (250MHz, CDCl₃) δ 8.07 (1H, s), 7.62 (1H, s), 7.50–7.40 (2H, m), 7.15 (2H, s), 7.03 (2H, t, J=8.8Hz), 4.87–4.83 (1H, q, J=6.5Hz), 4.35–4.25 (2H, m), 4.17 (2H, t, J=6.4Hz), 3.77 (1H, d, J=14.1Hz), 3.62–3.58 (2H, m), 3.34 (1H, d, J=14.1Hz), 3.00 (1H, d, J=11.6Hz), 2.70 (2H, t, J=6.4Hz), 2.66–2.52 (2H, m), 2.25 (6H, s), 1.43 (3H, d, J=6.6Hz). M/S ES⁺ 590. |
| 74 | F | 2-(CH₂)₂—N⟨pyrrolidine-CH₂OCH₃⟩ | ¹H NMR (360MHz, CDCl₃) δ 7.81 (1H, s), 7.63 (1H, s), 7.52–7.42 (2H, m), 7.16 (2H, s), 7.06 (2H, t, J=8.7Hz), 4.90–4.86 (1H, q, J=6.6Hz), 4.32 (1H, d, J=2.8Hz), 4.24 (1H, m), 4.10–4.02 (2H, m), 3.74 (1H, d, J=14.0Hz), 3.62–3.58 (1H, m), 3.46 (1H, d, J=2.8Hz), 3.30–3.28 (5H, m), 3.06–3.02 (2H, m), 2.88 (1H, m), 2.80–2.58 (4H, m), 2.22–2.18 (1H, m), 1.82–1.78 (1H, m), 1.70–1.58 (4H, m), 1.46 (3H, d, J=6.6Hz). M/S ES⁺ 590. |

The following examples illustrate pharmaceutical compositions according to the invention.

EXAMPLE 103A Tablets containing 1–25 mg of compound

|  | Amount mg |  |  |
|---|---|---|---|
| Compound of formula (I) | 1.0 | 2.0 | 25.0 |
| Microcrystalline cellulose | 20.0 | 20.0 | 20.0 |
| Modified food corn starch | 20.0 | 20.0 | 20.0 |
| Lactose | 58.5 | 57.5 | 34.5 |
| Magnesium Stearate | 0.5 | 0.5 | 0.5 |

EXAMPLE 103B Tablets containing 26–100 mg of compound

|  | Amount mg |  |  |
|---|---|---|---|
| Compound of formula (I) | 26.0 | 50.0 | 100.0 |
| Microcrystalline cellulose | 80.0 | 80.0 | 80.0 |
| Modified food corn starch | 80.0 | 80.0 | 80.0 |
| Lactose | 213.5 | 189.5 | 139.5 |
| Magnesium Stearate | 0.5 | 0.5 | 0.5 |

The compound of formula (I), cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active compound per tablet.

EXAMPLE 104 Parenteral injection

|  | Amount |
|---|---|
| Compound of formula (I) | 1 to 100 mg |
| Citric Acid Monohydrate | 0.75 mg |
| Sodium Phosphate | 4.5 mg |
| Sodium Chloride | 9 mg |
| Water for injection | to 10 ml |

The sodium phosphate, citric acid monohydrate and sodium chloride are dissolved in a portion of the water. The compound of formula (I) is dissolved or suspended in the solution and made up to volume.

EXAMPLE 105 Topical formulation

|  | Amount |
|---|---|
| Compound of formula (I) | 1–10 g |
| Emulsifying Wax | 30 g |
| Liquid paraffin | 20 g |
| White Soft Paraffin | to 100 g |

The white soft paraffin is heated until molten. The liquid paraffin and emulsifying wax are incorporated and stirred until dissolved. The compound of formula (I) is added and stirring continued until dispersed. The mixture is then cooled until solid.

EXAMPLE 106A—(Surface-Active Agent) Injection Formulation

| Compound of formula (I) | up to 10 mg/kg |
|---|---|
| Tween 80™ | up to 2.5% |
| [in 5% aqueous mannitol (isotonic)] |  |

The compound of formula (I) is dissolved directly in a solution of the commercially available Tween 80™ (polyoxyethylenesorbitan monooleate) and 5% aqueous mannitol (isotonic).

EXAMPLE 106B—(Emulsion) Injection Formulation

| Compound of formula (I) | up to 30 mg/ml |
|---|---|
| Intralipid™ (10–20%) |  |

The compound of formula (I) is dissolved directly in the commercially available Intralipid™ (10 or 20%) to form an emulsion.

EXAMPLE 106C—Alternative (Emulsion) Injectable Formulation

|  | Amount |
|---|---|
| Compound of formula (I) | 0.1–10 mg |
| Soybean oil | 100 mg |
| Egg Phospholipid | 6 mg |
| Glycerol | 22 mg |
| Water for injection | to 1 ml |

All materials are sterilized and pyrogen free. The compound of formula (I) is dissolved in soybean oil. An emulsion is then formed by mixing this solution with the egg phospholipid, glycerol and water. The emulsion is then sealed in sterile vials.

We claim:

1. A compound of the formula (I):

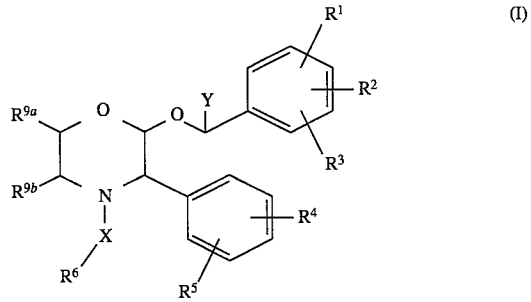

wherein:

$R^1$ is hydrogen, halogen, $C_{1-6}$alkyl, $C_{1-6}$alkoxy, $CF_3$, $NO_2$, $CN$, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, where $R^a$ and $R^b$ each independently represent hydrogen or $C_{1-4}$alkyl;

$R^2$ is hydrogen, halogen, $C_{1-6}$alkyl, $C_{1-6}$alkoxy substituted by $C_{1-4}$alkoxy or $CF_3$;

$R^3$ is hydrogen, halogen or $CF_3$;

$R^4$ is hydrogen, halogen, $C_{1-6}$alkyl, $C_{1-6}$alkoxy, $CF_3$, $NO_2$, $CN$, $SR^a$, $SOR^a$, $SO_2R^a$, $CO_2R^a$, $CONR^aR^b$,

75

$C_{2-6}$alkenyl, $C_{2-6}$alkynyl or $C_{1-4}$alkyl substituted by $C_{1-4}$alkoxy, where $R^a$ and $R^b$ each independently represent hydrogen or $C_{1-4}$alkyl;

$R^5$ is hydrogen, halogen, $C_{1-6}$alkyl, $C_{1-6}$alkoxy substituted by $C_{1-4}$alkoxy or $CF_3$;

$R^6$ is a 5-membered or 6-membered heterocyclic ring containing 2 or 3 nitrogen atoms optionally substituted by =O, =S or a $C_{1-4}$alkyl group, and optionally substituted by a group of the formula $ZNR^7R^8$ where Z is $C_{1-6}$alkylene or $C_{3-6}$cycloalkylene;

$R^7$ is hydrogen, $C_{1-4}$alkyl, $C_{3-7}$cycloalkyl or $C_{3-7}$cycloalkyl$C_{1-4}$alkyl, or $C_{2-4}$alkyl substituted by $C_{1-4}$alkoxy or hydroxyl;

$R^8$ is hydrogen, $C_{1-4}$alkyl, $C_{3-7}$cycloalkyl or $C_{3-7}$cycloalkyl$C_{1-4}$alkyl, or $C_{2-4}$alkyl substituted by one or two substituents selected from $C_{1-4}$alkoxy, hydroxyl or a 4, 5 or 6 membered heteroaliphatic ring containing one or two heteroatoms selected from N, O and S;

or $R^7$, $R^8$ and the nitrogen atom to which they are attached form a heteroaliphatic ring of 4 to 7 ring atoms, optionally substituted by one or two groups selected from hydroxy or $C_{1-4}$alkyl optionally substituted by a $C_{1-4}$alkoxy or hydroxyl group, and optionally containing a double bond, which ring may optionally contain an oxygen or sulphur ring atom, a group S(O) or $S(O)_2$ or a second nitrogen atom which will be part of a NH or $NR^c$ moiety where $R^c$ is $C_{1-4}$alkyl optionally substituted by hydroxy or $C_{1-4}$alkoxy;

or $R^7$, $R^8$ and the nitrogen atom to which they are attached form a non-aromatic azabicyclic ring system of 6 to 12 ring atoms;

or Z, $R^7$ and the nitrogen atom to which they are attached form a heteroaliphatic ring of 4 to 7 ring atoms which may optionally contain an oxygen ring atom;

$R^{9a}$ and $R^{9b}$ are each independently hydrogen or $C_{1-4}$alkyl, or $R^{9a}$ and $R^{9b}$ are joined so, together with the carbon atoms to which they are attached, there is formed a $C_{5-7}$ ring;

X is an alkylene chain of 1 to 4 carbon atoms optionally substituted by oxo; and Y is a $C_{1-4}$alkyl group optionally substituted by a hydroxyl group;

with the proviso that if Y is $C_{1-4}$alkyl, $R^6$ is substituted at least by a group of the formula $ZNR^7R^8$ as defined above;

or a pharmaceutically acceptable salt or prodrug thereof.

2. The compound of claim 1 of the formula (Ia):

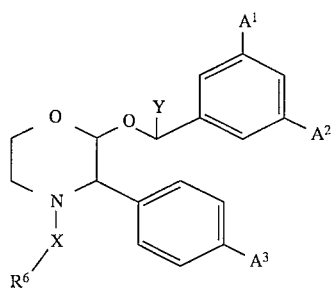
(Ia)

wherein:
$A^1$ is fluorine or $CF_3$;
$A^2$ is fluorine or $CF_3$;
$A^3$ is fluorine or hydrogen;
and X, Y and $R^6$ are as defined in claim 1; or a pharmaceutically acceptable salt or prodrug thereof.

76

3. The compound of claim 1 wherein Y represents a $C_{1-4}$alkyl group substituted by a hydroxy group; or a pharmaceutically acceptable salt or prodrug thereof.

4. The compound of claim 1 wherein Y represents a $C_{1-4}$alkyl group, with the proviso that $R^6$ is substituted at least by a group of the formula $ZNR^7R^8$ as defined in claim 1; or a pharmaceutically acceptable salt thereof.

5. The compound of claim 1 wherein $R^6$ represents a heterocyclic ring selected from:

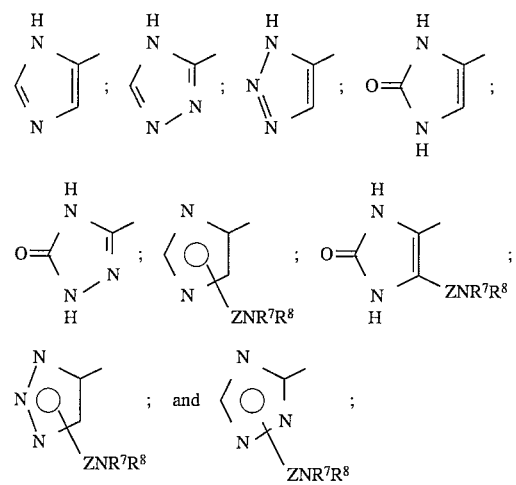

or a pharmaceutically acceptable salt or prodrug thereof.

6. The compound of claim 2 of the formula (Ib):

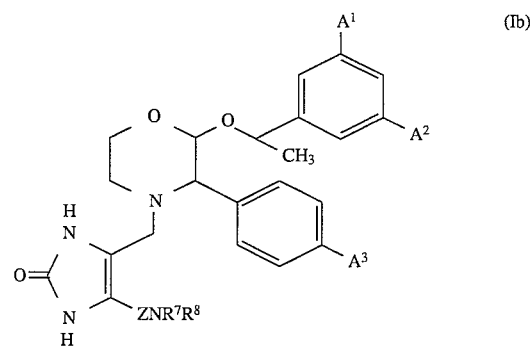
(Ib)

or a pharmaceutically acceptable salt thereof.

7. The compound of claim 2 of the formula (Ic):

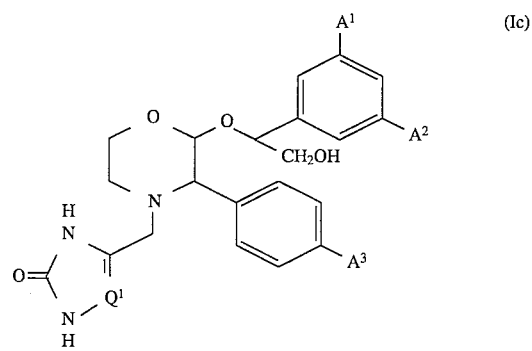
(Ic)

wherein:
$Q^1$ is CH, N or C—$ZNR^7R^8$ or a pharmaceutically acceptable salt or prodrug thereof.

8. The compound of claim 2 of the formula (Id):

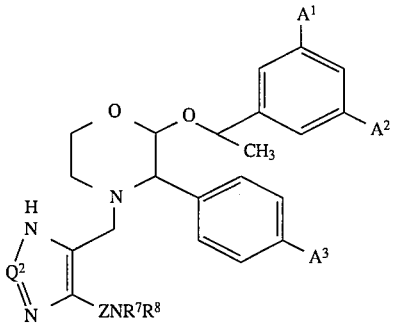

wherein:

Q² is CH or N or a pharmaceutically acceptable salt thereof.

9. A compound which is selected from the group consisting of:

2-(R)-(1-(R)-(3,5-bis(trifluoromethyl)phenyl) ethoxy)-4-(2,3-dihydro-5-(N,N-dimethylamino)methyl-2-oxo-1,3-imidazol-4-yl)methyl-3-(S)-(4-fluorophenyl)morpholine;

4-(2,3-dihydro-5-(N,N-dimethylamino)methyl-2-oxo-1,3-imidazol-4-yl)methyl-3-(S)-(4-fluorophenyl)-2-(R)-(1-(R)-(3-fluoro-5-(trifluoromethyl)phenyl)ethoxy)-morpholine;

3-(S)-(4-fluorophenyl)-2-(R)-(1-(R)-(3-fluoro-5(trifluoromethyl)phenyl) ethoxy)-4-(2,3-dihydro-2-oxo-5-pyrrolidinomethyl-1,3-imidazol-4-yl)methylmorpholine;

2-(R)-(1-(R)-(3,5-bis(trifluoromethyl)phenyl) ethoxy)-3-(S)-(4-fluorophenyl)-4-(2,3-dihydro-2-oxo-5-pyrrolidinomethyl-1,3-imidazol-4-yl)methylmorpholine;

2-(R)-(1-(R)-(3,5-bis(trifluoromethyl)phenyl) ethoxy)-3-(S)-(4-fluorophenyl)-4-(2,3-dihydro-5-(4-hydroxypiperidino)methyl-2-oxo-1,3-imidazol-4-yl)methylmorpholine;

3-(S)-(4-fluorophenyl)-2-(R)-(1-(R)-(3-fluoro-5-(trifluoromethyl)phenyl) ethoxy)-4-(2,3-dihydro-5-morpholinomethyl-2-oxo- 1,3-imidazol-4-yl)methylmorpholine;

2-(R)-(1-(R)-(3,5-bis(trifluoromethyl)phenyl) ethoxy)-3-(S)-(4-fluorophenyl)-4-(2,3-dihydro -5-morpholinomethyl-2-oxo-1,3-imidazol-4-yl)methylmorpholine;

4-(5-azetidinylmethyl-2,3-dihydro-2-oxo-1,3-imidazol-4-yl)methyl-2-(R)-(1-(R)-(3,5-bis(trifluoromethyl)phenyl)ethoxy)-3-(4-fluorophenyl) morpholine;

2-(R)-(1-(R)-(3,5-bis(trifluoromethyl)phenyl) ethoxy)-3-(S)-(4-fluorophenyl)-4-(2,3-dihydro -5-(N-methylpiperazinyl)methyl-2-oxo-1,3-imidazol-4-yl)methylmorpholine;

2-(R)-(1-(R)-(3,5-bis(trifluoromethyl)phenyl) ethoxy)-3-(S)-(4-fluorophenyl)-4-(2,3-dihydro -5-(N-(2-morpholinoethyl)aminomethyl)-2oxo-1,3-imidazol-4-yl)-methylmorpholine;

2-(R)-(1-(R)-(3,5-bis(trifluoromethyl)phenyl) ethoxy)-3-(S)-(4-fluorophenyl)-4-(2,3-dihydro -2-oxo-5-(N-(2-pyrrolidinoethyl)aminomethyl)-1,3 -imidazol-4-yl)methylmorpholine;

2-(R)-(1-(R)-(3,5-bis(trifluoromethyl)phenyl) ethoxy)-4-(5-(dimethylaminomethyl)-1,2,3-triazol-4-yl)methyl-3-(S)-(4-fluorophenyl)morpholine;

2-(R)-(1-(R)-(3,5-bis(trifluoromethyl)phenyl) ethoxy)-3-(S)-(4-fluorophenyl)-4-(N-(N'-methylaminoethyl)-1,2,4-triazol-3-yl)methylmorpholine;

2-(R)-(1-(R)-(3,5-bis(trifluoromethyl)phenyl) ethoxy)-3-(S)-(4-fluorophenyl)-4-(5-(N -methylaminomethyl)-1,2,3-triazol-4-yl)methylmorpholine;

4-(5-aminomethyl)-1,2,3-triazol-4-yl) methyl-2-(R)-(1-(R)-(3,5-bis(trifluoromethyl)phenyl) ethoxy)-3-(S)-(4-fluorophenyl)morpholine;

2-(R)-(1-(R)-(3,5-bis(trifluoromethyl)phenyl) ethoxy)-3-(S)-(4-fluorophenyl)-4-(5-pyrrolidinomethyl)-1,2,3-triazol-4-yl)methylmorpholine;

4-(5-(azetidinylmethyl)-1,2,3-triazol-4-yl)methyl-3-(S)-(4-fluorophenyl)-2-(R)-(1-(R) -(3-fluoro-5-(trifluoromethyl)phenyl)ethoxy)morpholine;

3-(S)-(4-fluorophenyl)-2-(R)-(1-(R)-(3-fluoro-5-(trifluoromethyl)phenyl)ethoxy)-4-(5-(pyrrolidinomethyl)-1,2,3-triazol-4-yl)methylmorpholine;

3-(S)-(4-fluorophenyl)-2-(R)-(1-(R)-(3-fluoro-5-(trifluoromethyl)phenyl)ethoxy)-4-(5-(morpholinomethyl)-1,2,3-triazol-4-yl)methylmorpholine;

4-(5-(N,N-dimethylaminomethyl)-1,2,3-triazol-4-yl)methyl-3-(S)-(4-fluorophenyl)-2-(R)-(1-(R)-(3-(trifluoromethyl)phenyl)ethoxy)morpholine;

2-(R)-(1-(R)-(3,5-bis(trifluoromethyl)phenyl) ethoxy)-3-(S)-(4-fluorophenyl)-4-(5-(N'-methylpiperazinomethyl)-1,2,3-triazol-4-yl) methylmorpholine;

2-(R)-(1-(R)-(3,5-bis(trifluoromethyl)phenyl) ethoxy)-3-(S)-(4-(1-(2-pyrrolidinoethyl)-1,2,3-triazol-4-yl)methylmorpholine;

2-(R)-(1-(R)-(3,5-bis(trifluoromethyl)phenyl) ethoxy)-3-(S)-phenyl-4-(2-(2-pyrrolidinoethyl)-1,2,3-triazol-4-yl)methylmorpholine;

2-(R)-(1-(R)-(3,5-bis(trifluoromethyl)phenyl) ethoxy)-3-(S)-(4-fluorophenyl)-4-(5-(morpholinomethyl)-1,2,3-triazol-4-yl)methylmorpholine;

4-(5-azetidinylmethyl)-1,2,3-triazol-4-yl) methyl-2-(R)-(1-(R)-(3,5-bis(trifluoromethyl)phenyl) ethoxy)-3-(S)-4-fluorophenyl)morpholine;

2-(R)-(1-(R)-(3,5-bis(trifluoromethyl)phenyl) ethoxy)-3-(S)-(4-fluorophenyl)-4-(5-(pyrrolinomethyl)-1,2,3-triazol-4-yl)methylmorpholine;

2-(R)-(1-(R)-(3,5-bis(trifluoromethyl)phenyl) ethoxy)-4-(5-(bis(methoxyethyl)aminomethyl)-1,2,3-triazol-4-yl)-methyl-3-(S)-(4-fluorophenyl) morpholine;

2-(R)-(1-(R)-(3,5-bis(trifluoromethyl)phenyl) ethoxy)-4-(2-chloro-5-morpholinomethyl-1,3-imidazol-4-yl)methyl-3-(S)-(4-fluorophenyl) morpholine;

2-(R)-(1-(R)-(3,5-bis(trifluoromethyl)phenyl) ethoxy)-4-(5-(N,N-dimethylaminomethyl)-1,3-imidazol -4-yl)methyl-3-(S)-(4-fluorophenyl)morpholine;

2-(R)-(1-(R)-(3,5-bis(trifluoromethyl)phenyl) ethoxy)-4-(5-(N,N-dimethylaminomethyl)-1,2,4-triazol -3-yl)methyl-3-(S)-(4-fluorophenyl)morpholine;

2-(R)-(1-(R)-(3,5-bis(trifluoromethyl)phenyl) ethoxy)-4-(5-N-(2,2-dimethoxyethyl)-N -methylaminomethyl)-1,2,3-triazol-4-yl)methyl-3-(S) -phenylmorpholine;

2-(R)-(1-(R)-(3,5-bis(trifluoromethyl)phenyl) ethoxy)-4-(5-(2-methoxyethyl)aminomethyl-1,2,3-triazol-4-yl)-methyl-3-(S)-phenylmorpholine;

2-(R)-(1-(R)-(3,5-bis(trifluoromethyl)phenyl) ethoxy)-4-(5-(N-(2-methoxyethyl)-N-methyl)aminomethyl -1,2,3-triazol-4-yl)methyl-3-(S)-phenylmorpholine;

2-(R)-(1-(R)-(3,5-bis(trifluoromethyl)phenyl) ethoxy)-4-(5-(N-isopropyl-N-(2-methoxyethyl) aminomethyl-1,2,3-triazol-4-yl)methyl-3-(S) -phenylmorpholine;

2-(R)-(1-(R)-(3,5-bis(trifluoromethyl)phenyl) ethoxy)-4-(5-(N-cyclopropyl-N-(2-methoxyethyl) aminomethyl-1,2,3-triazol-4-yl)methyl-3-(S)-phenylmorpholine;

2-(R)-(1-(R)-(3,5-bis(trifluoromethyl)phenyl) ethoxy)-4-(5-N,N-dibutylaminomethyl-1,2,3-triazol-4-yl)methyl-3-(S)-phenylmorpholine;

2-(R)-(1-(R)-(3,5-bis(trifluoromethyl)phenyl) ethoxy)-4-(5-N,N-diisopropylaminomethyl-1,2,3-triazol -4-yl)methyl-3-(S)-phenylmorpholine;

or a pharmaceutically acceptable salt thereof.

10. A compound which is:

2-(R)-(1-(R)-(3,5-bis(trifluoromethyl)phenyl) ethoxy)-4-(5-(dimethylaminomethyl)-1,2,3-triazol-4-yl)methyl-3-(S)-(4-fluorophenyl)morpholine;

or a pharmaceutically acceptable salt.

11. A compound which is selected from the group consisting of:

2-(R)-(1-(S)-(3,5-bis(trifluoromethyl)phenyl)-2-hydroxyethoxy)-3-(S)-(4-fluorophenyl)-4-(2,3-dihydro-3-oxo-1,2,4-triazol-5-yl)methylmorpholine;

2-(R)-(1-(S)-(3,5-bis(trifluoromethyl)phenyl)-2-hydroxyethoxy)-3-(S)-(4-fluorophenyl)-4-(1,2,4-triazol-3-yl) methylmorpholine;

4-(2,3-dihydro-3-oxo-1,2,4-triazol-5-yl)methyl-3-(S)-(4-fluorophenyl)-2-(R)-(1-(S)-(3-fluoro-5-(trifluoromethyl)phenyl) -2-hydroxyethoxy)morpholine;

4-(2,3-dihydro-2-oxo-1,3-imidazol-4-yl)methyl-2-(R)-(1-(S)-(3,5-bis(trifluoromethyl) phenyl)-2-hydroxyethoxy)-3-(S)-(4-fluorophenyl) morpholine;

4-(2,3-dihydro-2-oxo-5-pyrrolidinomethyl-1,3-imidazol-4-yl)methyl-2-(R)-(1-(S)-(3,5-bis(trifluoromethyl)phenyl)-2-hydroxyethoxy)-3-(S)-(4-fluorophenyl)morpholine;

4-(2,3-dihydro-3-oxo-1,2,4-triazol-5-yl)-3-(S)-phenyl-2-(R)-(1-(S)-(3-(trifluoromethyl)phenyl)-2-hydroxyethoxy)morpholine;

4-(2,3-dihydro-3-oxo-1,2,4-triazol-5-yl)methyl-2-(R)-(1-(S)-(3-fluoro-5-(trifluoromethyl)phenyl)-2-hydroxyethoxy)-3-(S)-phenylmorpholine;

2-(R)-(1-(S)-(3,5-bis(trifluoromethyl)phenyl)-2-hydroxyethoxy)-4-(2,3-dihydro-3-oxo-1,2,4-triazol-5-yl)-3-(S)-phenylmethylmorpholine;

3-(S)-phenyl-4-(1,2,4-triazol-3-yl)-2-(R)-(1-(S)-3-(trifluoromethyl)phenyl)-2-hydroxyethoxy)morpholine;

or a pharmaceutically acceptable salt or prodrug thereof.

12. The compound of claim 1 of the formula (Ie):

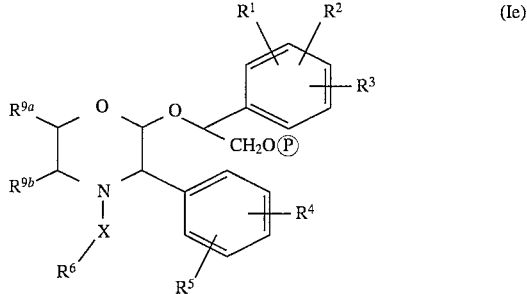

(Ie)

wherein:

P in a circle is PO(OH)O—.M⁺, PO(O—)₂.2M⁺, or PO(O—)₂.D²⁺; wherein M⁺ is a pharmaceutically acceptable monovalent counterion; and D²⁺ is a pharmaceutically acceptable divalent counterion.

13. The compound of claim 2 of the formula (If):

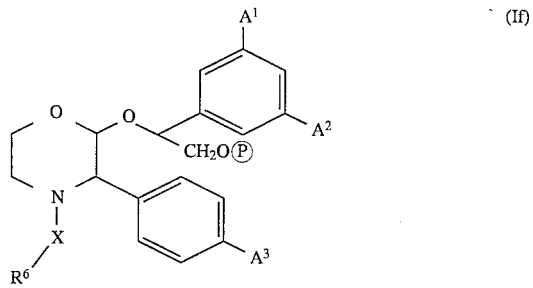

(If)

wherein:

P in a circle is PO(OH)O—.M⁺, PO(O—)₂.2M⁺, or PO(O—)₂.D²⁺; wherein M⁺ is a pharmaceutically acceptable monovalent counterion; and D²⁺ is a pharmaceutically acceptable divalent counterion.

14. The compound of claim 2 of the formula (Ig):

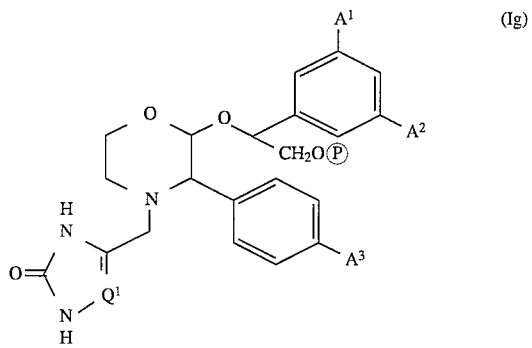

(Ig)

wherein:

Q¹ is CH, N or C—ZNR⁷R⁸ and P in a circle is PO(OH)O—.M⁺, PO(O—)₂.2M⁺, or PO(O—)₂.D²⁺; wherein M⁺ is a pharmaceutically acceptable monovalent counterion; and D²⁺ is a pharmaceutically acceptable divalent counterion.

15. The compound of claim 2 of the formula (Ih) and pharmaceutically acceptable salts thereof:

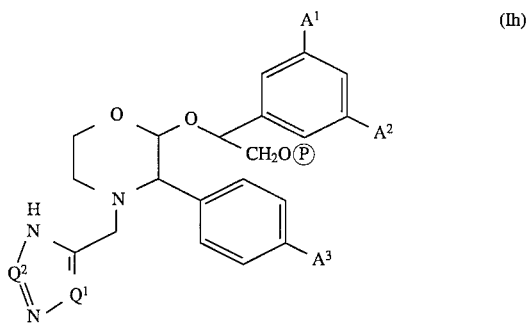

(Ih)

wherein:

Q¹ is CH, N or C—ZNR⁷R⁸, Q² is CH or N; and P in a circle is PO(OH)O—.M⁺, PO(O—)₂.2M⁺, or PO(O—)₂.D²⁺; wherein M⁺ is a pharmaceutically acceptable monovalent counterion; and D²⁺ is a pharmaceutically acceptable divalent counterions.

16. A compound which is selected from the group consisting of:

2-(R)-(1-(S)-(3,5-bis(trifluoromethyl)phenyl)-2-phosphoryloxyethoxy)-3-(S)-(4-fluorophenyl)-4-(2,3-dihydro-3-oxo -1,2,4-triazol-5-yl)methylmorpholine;

2-(R)-(1-(S)-(3,5-bis(trifluoromethyl)phenyl)-2-phosphoryloxyethoxy)-3-(S)-(4-fluorophenyl)-4-(1,2,4-triazol-3-yl)methylmorpholine;

4-(2,3-dihydro-3-oxo-1,2,4-triazol-5-yl)methyl-2-(R)-(1-(S)-3-fluoro-5-(trifluoromethyl)phenyl)-2-phosphoryloxyethoxy)-3-(S)-phenylmorpholine;

2-(R)-(1-(S)-(3,5-bis(trifluoromethyl)phenyl)-2-phosphoryloxyethoxy)-4-(2,3-dihydro-3-oxo-1,2,4-triazol-5-yl)methyl-3-(S)-phenylmorpholine;

or a pharmaceutically acceptable salt thereof.

17. The compound of claim 1 of the formula (Ii):

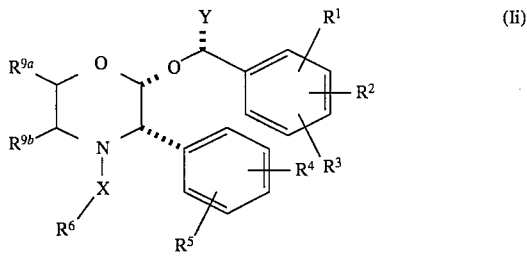

wherein $R^1$, $R^2$, $R^3$, $R^4$, $R^5$, $R^6$, $R^{9a}$, $R^{9b}$, X and Y are as defined in claim 1; or a pharmaceutically acceptable salt or prodrug thereof.

18. A pharmaceutical composition comprising a compound of claim 1 in association with a pharmaceutically acceptable carrier or excipient.

19. A pharmaceutical composition comprising a compound of claim 10 in association with a pharmaceutically acceptable carrier or excipient.

20. A method for the treatment or prevention of physiological disorders associated with an excess of tachykinins, which method comprises administration to a patient in need thereof of an effective amount of a compound of claim 1; or a pharmaceutically acceptable salt or prodrug thereof.

21. The method of claim 20 for the treatment of pain or inflammation.

22. The method of claim 20 for the treatment of migraine.

23. The method of claim 20 for the treatment or prevention of emesis.

24. A process for the preparation of a compound of claim 1, which comprises:

(A) reacting a compound of formula (II):

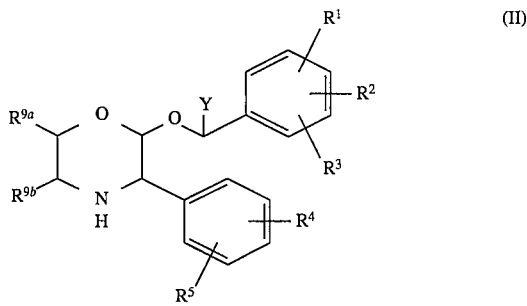

wherein $R^1$, $R^2$, $R^3$, $R^4$, $R^5$ and Y are as defined in relation to formula (I) with a compound of formula (III):

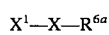

where X is as defined in claim 1, $R^{6a}$ is a group of the formula $R^6$ as defined in claim 1 or a precursor therefor and $X^1$ is a leaving group such as bromine or chlorine; and, if $R^{6a}$ is a precursor group, convening it to a group $R^6$; or (B) wherein $R^6$ represents 1,2,3-triazol-4-yl substituted by $CH_2NR^7R^8$ and X is —$CH_2$—, by reaction of a compound of formula (IV)

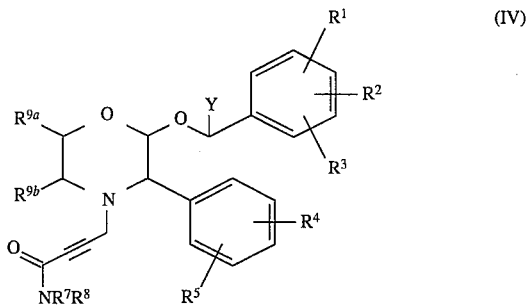

with an azide, followed by reduction of the carbonyl group adjacent to $NR^7R^8$; or (C) wherein $R^6$ represents 1,2,3-triazol-4-yl substituted by $CH_2NR^7R^8$ and X is —$CH_2$—, by reaction of a compound of formula (V)

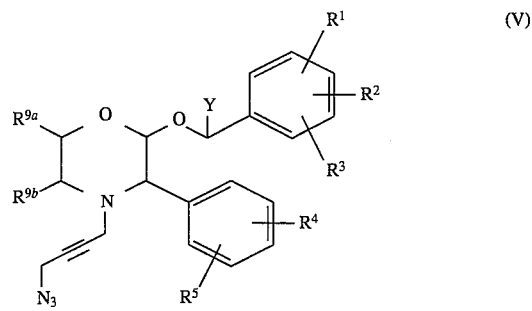

with an amine of formula $NHR^7R^8$; or (D) wherein $R^6$ represents substituted or unsubstituted 1,3,5-triazine, by reaction of compounds of formula (VI):

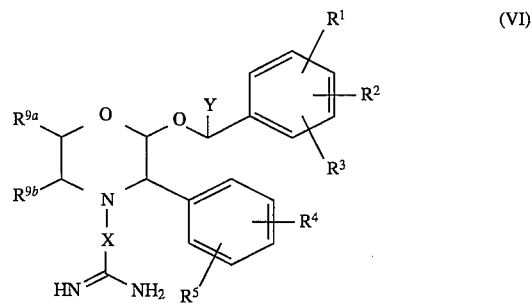

with a substituted or unsubstituted 1,3,5-triazine; or (E) wherein $R^6$ represents substituted or unsubstituted 1,2,4-triazine, by reaction of a compound of formula (VII) with a dicarbonyl compound of formula (VIII):

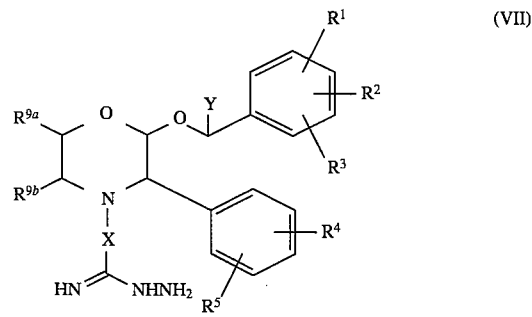

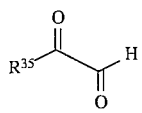

(VIII)

wherein

R³⁵ represents H or a suitable substituent such as ZNR⁷R⁸; or (F) wherein R⁶ represents a substituted 1,2,4-triazolyl group, by reaction of a compound of formula (II) with a compound of formula (IX)

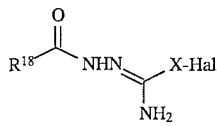

wherein X is as defined in claim 1, Hal is a halogen atom, and R¹⁸ is H, CONH₂ or OCH₃ (which is converted to an oxo substituent under the reaction conditions), in the presence of a base, followed where necessary by conversion to a compound of formula (I); or (G) wherein R⁶ represents thioxotriazolyl, by reaction of a compound of formula (X)

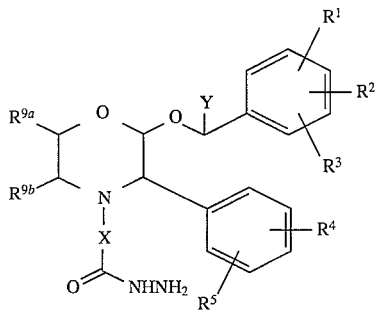

with a compound of formula HNCS, in the presence of a base; or (H) wherein R⁶ is substituted by a group of ZNR⁷R⁸, reacting a compound of formula (II) with a compound of formula (XII):

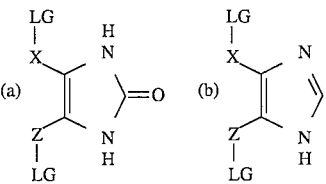

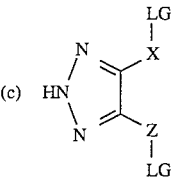

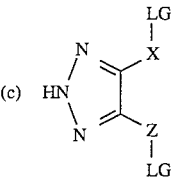

wherein each LG, which may be the same or different, is a leaving group, and X and Z are as defined in claim 1, followed by reaction of the resultant compound with an amine NHR⁷R⁸ to complete the ZNR⁷R⁸ moiety; or (J) by interconversion of a compound of formula (I) into another compound of formula (I);

each process being followed, where necessary, by the removal of any protecting group where present;

and when the compound of formula (I) is obtained as a mixture of enantiomers or diastereoisomers, optionally resolving the mixture to obtain the desired enantiomer; and/or, if desired, converting the resulting compound of formula (I) or a salt thereof, into a pharmaceutically acceptable salt or prodrug thereof.

* * * * *